US006482588B1

(12) United States Patent
Van Doorn et al.

(10) Patent No.: US 6,482,588 B1
(45) Date of Patent: Nov. 19, 2002

(54) DETECTION AND IDENTIFICATION OF HUMAN PAPILLOMAVIRUS BY PCR AND TYPE-SPECIFIC REVERSE HYBRIDIZATION

(75) Inventors: Leen-Jan Van Doorn, Ridderkerk; Wim Quint, Nootdorp; Berhnard Kleter, Delft; Jan TerSchegget, Amsterdam, all of (NL)

(73) Assignee: Innogenetics S.A. (BE)

( * ) Notice: Subject to any disclaimer, the term of this patent is extended or adjusted under 35 U.S.C. 154(b) by 0 days.

(21) Appl. No.: 09/527,030

(22) Filed: Mar. 16, 2000

Related U.S. Application Data

(63) Continuation of application No. PCT/EP98/05829, filed on Sep. 14, 1998.

(30) Foreign Application Priority Data

Sep. 16, 1997  (EP) ............................................. 97870136

(51) Int. Cl.[7] ............................. C12Q 1/70; C12Q 1/68; C12P 19/34; C07H 21/04

(52) U.S. Cl. .............................. 435/5; 435/6; 435/91.1; 536/24.32

(58) Field of Search .............................. 435/6, 5, 91.1; 536/24.32

(56) References Cited

U.S. PATENT DOCUMENTS 5,705,627 A  *  1/1998  Manos et al. ............... 536/24.3

FOREIGN PATENT DOCUMENTS

| WO | 90 02821 | 3/1990 |
| WO | 91 10675 | 7/1991 |

OTHER PUBLICATIONS

Baay, Marc F.D. et al., *J. of Clinical Microbio.*, vol. 34, No. 3 (1996) pp. 745–747.
Chan, Shih–yen et al., *J. of Virology*, vol. 69, (1995) pp. 3074–3083.
Claas, Eric C.J. et al., *Am. J. of Pathology*, vol. 135, No. 4 (1989) pp. 703–709.
Cornelissen, Marion T.E. et al., *J. Gen. Virol.*, vol. 70 (1989) pp. 2555–2562.
Cox, J. Thomas MD et al., *Am. J. Obstet Gynecol.*, vol. 172, No. 3 (1995) pp. 946–954.
Falcinelli, Cristina et al., *J. of Med. Virology*, vol. 37 (1992) pp. 93–98.
Manos, M. M. et al., *Cancer Cells 7/Molecular Diagnostics of Human Cancer* (1989) pp. 209–214.
Remmink, Ans J. et al., *Int. J. Cancer*, vol. 61 (1995) pp. 306–311.
Tieben, Linda M. et al., *J. of Virological Methods*, vol. 42 (1993) pp. 265–280.
Van Den Brule, Adriaan, J.C. et al., *Int. J. Cancer*, vol. 45 (1990) pp. 644–649.

(List continued on next page.)

*Primary Examiner*—Kenneth R. Horlick
*Assistant Examiner*—Teresa Strzelecka
(74) *Attorney, Agent, or Firm*—Bierman, Muserlian and Lucas

(57) ABSTRACT

The present invention relates to a method for detection and/or identification of HPV present on a biological sample, comprising the steps of amplification of HPV polynucleic acids and of hybridization of said amplified ploynucleic acids to a number of probes. By means of PCR, a short fragment of the L1 gene of HPV is amplified. The amplimers are then contacted with probes that specifically hybridize to said short fragment of the L1 gene of either one or more than one HPV type. A preferred format is the reverse hybridization technique, more particularly the LiPA technique. The invention also relates to primers and probes to be used in a method of detection and/or identification of HPV and to a diagnostic kit to perform said method.

25 Claims, 14 Drawing Sheets

OTHER PUBLICATIONS

Figure 1A:
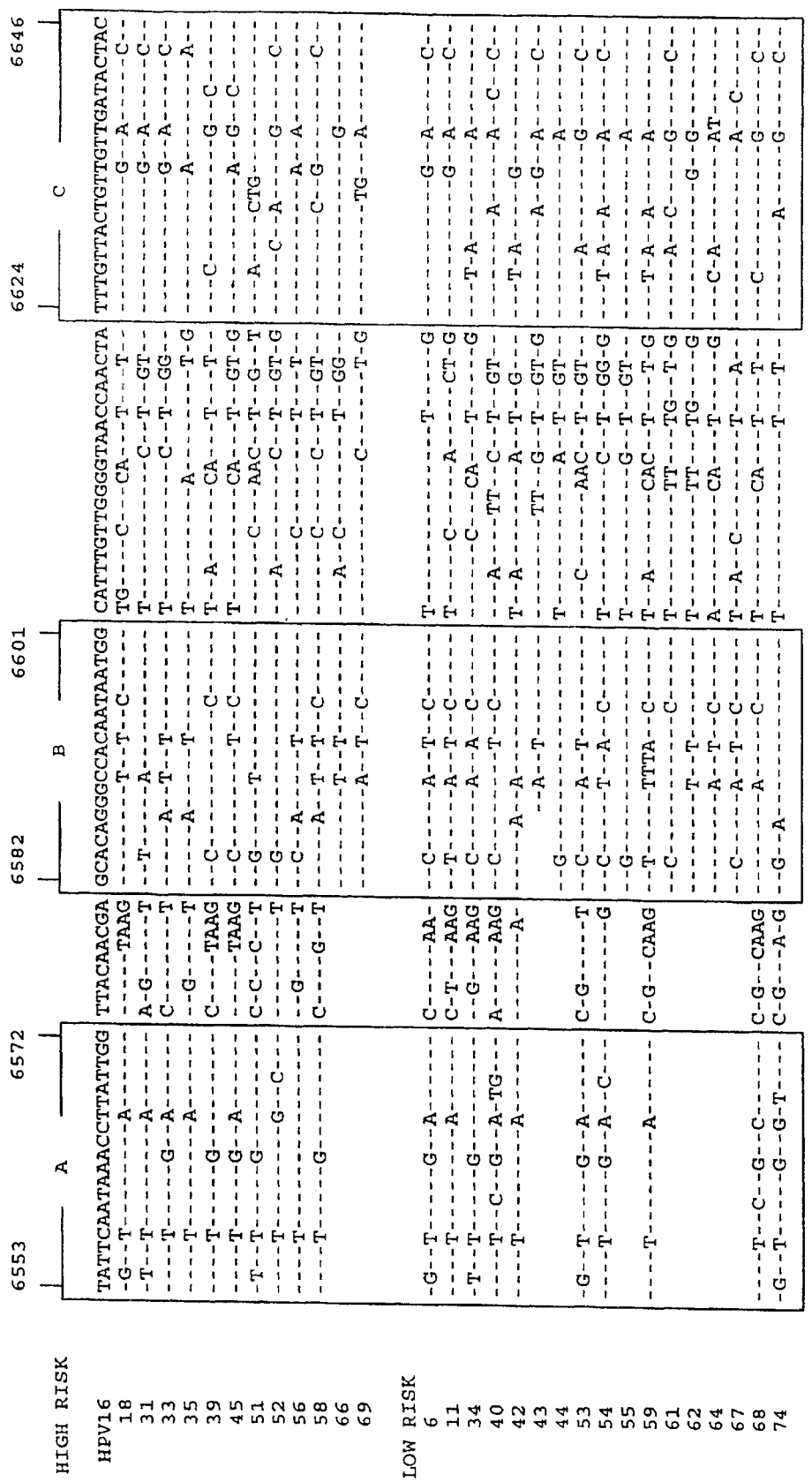

Young, L.S. et al., *Br. Med. J.*, vol. 298 (1989) pp. 14–18.
Woodworth, C.D. et al., *Cancer Research*, vol. 50 (1990) pp. 3709–3715.
Paper T. et al: Gene, vol. 103, No. 2, Jan. 1, 1991, pp. 155–161, XP000272760.
Icenogle J.P. et al.,: Virology, vol. 184, Sep. 1, 1991 pp. 101–107 XP002073057.
Seedorf K. et al: Virology, vol. 145, No. 1, Aug. 1985, pp. 181–185, XP002059799.

Goldsborough M.D. et al.,: Virology, vol. 171, Jul. 1989 pp. 306–311, XP002073058.

Samiotak M. et al: Analytical Biochemistry, vol. 253, No. 2, Nov. 15, 1997, pp. 156–161, XP00721248.

Kleter B. et al.,: Amer. J. Pathology, vol. 153, No. 6, Dec. 1998 pp. 1731–1739, XP0–02100812.

* cited by examiner

Phylogenetic tree of HPV sequences in the My11/09 region

Phylogenetic tree of HPV sequences between the B and C regions

Phylogenetic tree of HPV sequences between the A and C regions

Outline of a HPV LiPA

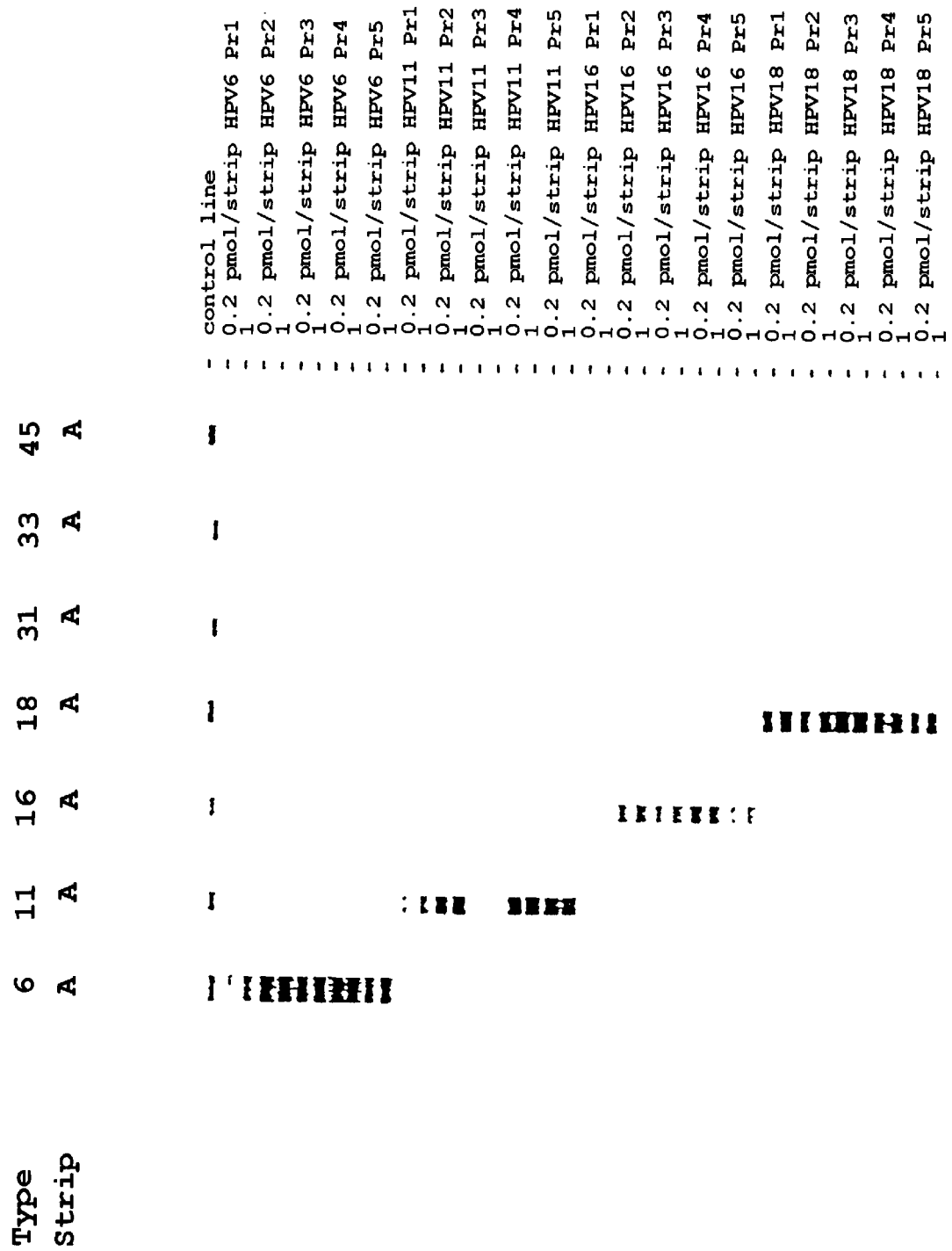

FIG. 8A

| Type | Strip | control line | 0.2 pmol/strip HPV6 Pr1 | 0.2 pmol/strip HPV6 Pr2 | 0.2 pmol/strip HPV6 Pr3 | 0.2 pmol/strip HPV6 Pr4 | 0.2 pmol/strip HPV6 Pr5 | 0.2 pmol/strip HPV11 Pr1 | 0.2 pmol/strip HPV11 Pr2 | 0.2 pmol/strip HPV11 Pr3 | 0.2 pmol/strip HPV11 Pr4 | 0.2 pmol/strip HPV11 Pr5 | 0.2 pmol/strip HPV16 Pr1 | 0.2 pmol/strip HPV16 Pr2 | 0.2 pmol/strip HPV16 Pr3 | 0.2 pmol/strip HPV16 Pr4 | 0.2 pmol/strip HPV16 Pr5 | 0.2 pmol/strip HPV18 Pr1 | 0.2 pmol/strip HPV18 Pr2 | 0.2 pmol/strip HPV18 Pr3 | 0.2 pmol/strip HPV18 Pr4 | 0.2 pmol/strip HPV18 Pr5 |
|---|---|---|---|---|---|---|---|---|---|---|---|---|---|---|---|---|---|---|---|---|---|---|
| 6 | A | — | ▪▪▪▪▪ | | | | | | | | | | | | | | | | | | | |
| 16 | A | — | | | | | | | | | | | | | | ▪▪▪ | | | | | | |
| 31 | A | — | | | | | | | | | | | | | | | | | | | | |
| 33 | A | — | | | | | | | | | | | | | | | | | | | | |
| 45 | A | — | | | | | | | | | | | | | | | | | | | | |

Nucleotide sequence alignments of 39 HPV genotypes

| | 6582　　　　　6601　B | 6624　　　　　6646　C |
|---|---|---|
| HPV16 | GCACAGGGCCACAATAATGG | CATTTGTTGGGGTAACCAACTA | TTTGTTACTGTTGTTGATACTAC |
| 6 | --C-----A--T--C----- | T--------------T-----G | ----------G--A-----C-- |
| 11 | --T-----A--T--C----- | T-----C-----A-----CT-G | ----------G--A-----C-- |
| 13 | --C-----A----------- | T--A--------C--T--CT-G | ----------A----------- |
| 18 | --------T--T--C----- | TG----C---CA---T---T-- | ----------G--A-----C-- |
| 26 | --------T--T-------- | T--C--------C--T---T-G | --------CTG--------C-- |
| 30 | --------A---------- | -----------C-----GG-- | ----------G--C--C-- |
| 31 | --T-----A---------- | T-----------C--T--GT-- | ----------G--A-----C-- |
| 33 | ------A--T--T-------- | T-----------C--T--GG-- | ----------G--A-----C-- |
| 34 | --C-----A--A--C----- | -------C---CA---T-----G | ---T-A---------A-------- |
| 35 | ------A-----T-------- | T----------A--------T-G | ----------A--------A-- |
| 39 | --C----------C----- | T--A------CA---T---T-- | ---C----------G--C--C-- |
| 40 | --C--------T--C----- | ---A----TT--C--T--GT-- | ----------A-----A--C--C-- |
| 42 | ------A--A---------- | T--A--------A--T--G--- | ---T-A-----G---------- |
| 43 | --------A--T-------- | ---------TT--G--T--GT-G | ----------A--G--A-----C-- |
| 44 | --G----------------- | T-----------A--T--GT-- | ----------A--------- |
| 45 | --C--------T--C----- | T----------CA---T--GT-G | ----------A--G--C----- |
| 51 | --G-----T---------- | -------C---AAC--T--G--T | ---A-----CTG------------ |
| 52 | --G----------------- | ---A--------C--T--GT-G | -----C--A-----G-----C-- |
| 53 | --C-----A--T-------- | ---C------AAC--T--GT-- | ----------A-----G-----C-- |
| 54 | --C-----T--A--C----- | T-----------C--T--GG-G | ---T-A--A-----A-----C-- |
| 55 | --G----------------- | T-----------G--T--GT-- | ----------A--------- |
| 56 | --C--A-----T-------- | -------C---------T---T-- | ----------A--A-------- |
| 58 | ------A--T--T--C----- | -------C-----C--T--GT-- | ----------C--G--------C-- |
| 59 | --T-----TTTA--C----- | T--A------CAC--T---T-G | ---T-A--A-----A-------- |
| 61 | --C----------C----- | T---------TT---TG--T-G | -----A--C-----G-----C-- |
| 62 | --------T--T-------- | T---------TT---TG----G | ----------G--G-------- |
| 64 | --------A--T--C----- | A---------CA---T-----G | ---C-A--------AT------- |
| 66 | --------T--T-------- | ---A--C---------T--GG-- | ----------G--------- |
| 67 | --C-----A--T--C----- | T--A--C---------T---A-- | ----------A--C----- |
| 68 | --------A-----C----- | T----------CA---T---T-- | ---C----------G-----C-- |
| 69 | --------A--T--C----- | -------------C------T-G | ---------TG---A-------- |
| 70 | --C-----AACT-------- | ----------CA------GT-G | ---A--------G--G--C----- |
| 72 | --C-----T--T-------- | ---C------TT---TG-G--T | -----G--A-----A-------- |
| 73 | --------T--T-------- | T---------CA---T---T-- | ---T-A---------A-------- |
| 74 | --G--A-------------- | T--,----------T---T-- | --------A-----G-----C-- |
| MM4 | ---------A--T-------- | -------C---AA---T--G--T | ---A-----TG------C----- |
| MM7 | --C-----A--T-------- | ----------TT---TG-GT-- | ---------A-----A-------- |
| MM8 | --G-G---T--T--C----- | T--A--C--TT---T----T-G | -----C--G--G-----C----- |

FIG. 9

Outline HPV-LiPA for identification of 25 types

US 6,482,588 B1

DETECTION AND IDENTIFICATION OF HUMAN PAPILLOMAVIRUS BY PCR AND TYPE-SPECIFIC REVERSE HYBRIDIZATION

This application is a Continuation of PCT International Application No. PCT/EP98/05829 filed on Sep. 14, 1998, which designated the United States, and on which priority is claimed under 35 U.S.C. §120, the entire contents of which are hereby incorporated by reference.

FIELD OF THE INVENTION

The present invention relates to the field of detection and identification of Human Papillomavirus (HPV) infections in clinical samples.

BACKGROUND OF THE INVENTION

Cervical cancer is the second most common malignancy in women, following breast cancer. Carcinoma of the cervix is unique in that it is the first major solid tumor in which HPV DNA is found in virtually all cases and in precursor lesions worldwide.

Nowadays, 74 HPV genotypes have been characterized and are numbered in chronological order of isolation. HPV is epitheliotropic and infects only the skin (cutaneous types) or the mucosa of the respiratory and anogenital tract (mucosal types). Thirty-six of the 74 HPV types are known to infect the uterine cervix. Based on the induced benign, premalignant or malignant lesions, HPV is divided into low-risk (e.g., HPV types 6, 11, 42, 43 and 44) and high-risk types (e.g., types 16, 18, 31, 33 and 45), respectively. The high-risk types account for more than 80% of all invasive cervical cancers. Consequently, detection and identification of HPV types is very important. The high-risk types are more consistently found in high grade SIL (Squamous Intraepithelial Lesion) and carcinoma in-situ than low-risk types which are mainly found in low grade SIL. This epidemiological observation is supported by molecular findings. For instance, the E6 and E7 proteins from low-risk types 6 and 11 bind p53 and pRB too weakly to immortalize keratinocytes in vitro or to induce malignant transformation in vivo (Woodworth et al., 1990). The circular ds-DNA genome of low-risk HPV types remains episomal whereas the genome of high-risk HPV types is able to integrate into the human genome.

Screening for malignant and premalignant disorders of the cervix is usually performed according to the Papanicoloau (PAP) system. The cervical smears are examined by light microscopy and the specimens containing morphologically abnormal cells are classified into PAP I to V, at a scale of increasing severity of the lesion. This cytomorphological method is an indirect method and measures the possible outcome of an HPV infection. Therefore, HPV DNA detection and typing is of importance in secondary screening in order to select patients for monitoring (follow-up) and treatment. This means that cervical smears classified as PAP II (atypical squamous metaplasia) or higher classes should be analyzed for low-risk and high-risk HPV types. Follow-up studies have shown that only high-risk HPV types are involved in the progression from cytologically normal cervix cells to high grade SIL (Remminck et al., 1995). These results indicate that the presence of high-risk HPV types is a prognostic marker for development and detection of cervical cancer.

Detection of HPV Infections

Diagnosis of HPV by culture is not possible. Also diagnosis by detection of HPV anti-bodies appears to be hampered by insufficient sensitivity and specificity. Direct methods to diagnose an HPV infection are mainly based on detection of the viral DNA genome by different formats of DNA/DNA hybridization with or without prior amplification of HPV DNA. The polymerase chain reaction (PCR) is a method that is highly efficient for amplification of minute amounts of target DNA. Nowadays, mainly three different primer pairs are used for universal amplification of HPV DNA. Two of these primer pairs, MY11/MY09 and GP5/GP6, are directed to conserved regions among diffent HPV types in the L1 region (Manos et al., 1989; Van den Brule et al., 1990). The other primer pair, CPI/CPIIg, is directed to conserved regions in the El region (Tieben et al., 1993).

Typing of HPV Isolates

There are several methods to identify the various HPV types.

1. HPV DNA can be typed by PCR primers that recognize only one specific type. This method is known as type-specific PCR. Such methods have been described for HPV types 6, 11, 16, 18, 31 and 33 (Claas et al., 1989; Cornelissen et al., 1989; Falcinelli et al., 1992; Van den Brule et al., 1990; Young et al., 1989). The primers are aimed at the E5, L1, E6, L1, E2 and E1 regions of the HPV genome for types 6, 11, 16, 18, 31 and 33, respectively (Baay et al., 1996). The synthesized amplimer sizes vary from 217 bp to 514 bp.

2. Another method is general amplification of a genomic part from all HPV types followed by hybridization with two cocktails of type-specific probes differentiating between the oncogenic and non-oncogenic groups, respectively. A similar typing method has been described without prior amplification of HPV DNA. In the Hybrid capture assay (Hybrid Capture Sharp Assay; Digene, Silver Springs, Md.), each sample is tested for a group of "high-risk" HPV types (16, 18, 31, 33, 35, 45, 51, 52 and 56) and for another group of "low-risk" HPV types (6, 11, 42, 43 and 44) (Cox et al., 1995).

At present, classification of human papillomaviruses can be performed for instance by sequence analysis of a 450 bp PCR fragment synthesized by the primers MY11/MY09 in the L1 region (Chan et al., 1995) or by the primers CPI and CPIIg in the E1 region (Tieben et al., 1993). Phylogenetic analysis of these sequences allows classification of the different HPV types. By definition, if the sequence differences between two HPV isolates is higher than 10% they are classified as different types. Consequently, if the sequence differs more than 10% from any known HPV type it is classified as a novel HPV genotype. HPV isolates that differ between 2–10% are classified as different subtypes. Finally, if the sequence variation is below 2%, the 2 isolates are classified within the same subtype as different variants.

Aims of the Invention

It is an aim of the present invention to provide a rapid and reliable method for detection and/or identification of HPV, possibly present in a biological sample.

It is more particularly an aim of the present invention to provide a method for detection and/or identification of HPV comprising amplification of a polynucleic acid fragment of HPV and subsequent hybridization of this fragment to suitable probes.

It is also an aim of the present invention to provide a number of oligonucleotide primers and probes enabling said method of detection and/or amplification of HPV.

It is also an aim of the present invention to provide new HPV sequences.

It is furthermore an aim of the present invention to provide protocols according to which said amplification and hybridization steps can be performed. One format for the hybridization step is, for instance, the reverse hybridization format, and more particularly the LiPA technique.

It is also an aim of the present invention to compose diagnostic kits comprising said primers and probes, permitting the rapid and reliable detection and/or identification of HPV possibly present in a biological sample.

All the aims of the present invention are met by the following specific embodiments.

DETAILED DESCRIPTION OF THE INVENTION

The present invention provides a method for detection and/or identification of HPV, possibly present in a biological sample, comprising the following steps:
(i) amplification of a polynucleic acid fragment of HPV by use of:
  a 5'-primer specifically hybridizing to the A region or B region of the genome of at least one HPV type, said A region and B region being indicated in FIG. 1, and
  a 3'-primer specifically hybridizing to the C region of the genome of at least one HPV type, said C region being indicated in FIG. 1;
(ii) hybridizing the amplified fragments from step (i) with at least one probe capable of specific hybridization with the D region of at least one HPV type, said D region being indicated in FIG. 1.

According to one preferred embodiment of the present invention, said probe mentioned in step (ii) is capable of specific hybridization with the D region of the genome of only one HPV type, and thus enables specific identification of this HPV type, when this type is present in a biological sample.

According to another preferred embodiment of the present invention, said probe mentioned in step (ii) is capable of specific hybridization with the D region of more than one HPV type, and thus enables detection of any of said more than one HPV type, when any of said types is present in a biological sample.

According to another preferred embodiment of the present invention, the 3'-end of said 5'-primer specifically hybridizing to the A region of the genome of at least one HPV type, is situated at position 6572 of the genome of HPV 16, or at the corresponding position of any other HPV genome, as indicated in FIG. 1.

According to another preferred embodiment of the present invention, the 3'-end of said 5'-primer specifically hybridizing to the B region of the genome of at least one HPV type, is situated at position 6601 of the genome of HPV 16, or at the corresponding position of any other HPV genome, as indicated in FIG. 1.

According to another preferred embodiment of the present invention, the 3'-end of said 3'-primer specifically hybridizing to the C region of the genome of at least one HPV type, is situated at position 6624 of the genome of HPV 16, or at the corresponding position of any other HPV genome, as indicated in FIG. 1.

According to another preferred embodiment of the present invention, said probe capable of specific hybridization with the D region of the genome of only one HPV type, more particularly specifically hybridizes to the E region, with said E region being a subregion of the D region, as indicated in FIG. 1.

According to another preferred embodiment of the present invention, said probe capable of specific hybridization with the D region of the genome of only one HPV type, more particularly specifically hybridizes to the 22 bp region situated between the B region and the C region, as indicated in FIG. 1.

According to another preferred embodiment, said 5'-primer specifically hybridizing to the A region of the genome of at least one HPV type, is chosen from the following list:
  SGP3, SGP3A, SGP3B, SGP3C, SGP3D, SGP3E, SGP3F, SGP3G.

The sequences of said primers are shown in table 1 and in table 4.

According to another preferred embodiment, said 5'-primer specifically hybridizing to the B region of the genome of at least one HPV type, is chosen from the following list:
  SGP1, SGP1A, SGP1B, SGP1C, SGP1D.

The sequences of said primers are shown in table 1, in table 4 and in table 11.

According to another preferred embodiment, said 3'-primer specifically hybridizing to the C region of the genome of at least one HPV type, is chosen from the following list:
  SGP2, SGP2A, SGP2B, SGP2C, SGP2D, SGP2E, SGP2F, SGP2H, SGP2I, SGP2J, SGP2K, SGP2L, SGP2M, SGP2N, SGP2P.

The sequences of said primers are shown in table 1, in table 4 and in table 11.

According to another preferred embodiment, said probe capable of specific hybridization with the aforementioned 22bp region of only one HPV type, is chosen from the following list:
  HPV6 Pr1, HPV6 Pr2, HPV6 Pr3, HPV6 Pr4, HPV6 Pr5, HPV11 Pr1, HPV11 Pr2, HPV11 Pr3, HPV11 Pr4, HPV11 Pr5, HPV16 Pr1, HPV16 Pr2, HPV16 Pr3, HPV16 Pr4, HPV16 Pr5, HPV18 Pr1, HPV18 Pr2, HPV18 Pr3, HPV18 Pr4, HPV18 Pr5, HPV31 Pr1, HPV31 Pr2, HPV31 Pr3, HPV31 Pr4, HPV31 Pr5, HPV31 Pr21, HPV31 Pr22, HPV31 Pr23, HPV31 Pr24, HPV31 Pr25, HPV31 Pr26, HPV31 Pr31, HPV31 Pr32, HPV33 Pr1, HPV33 Pr2, HPV33 Pr3, HPV33 Pr4, HPV33 Pr5, HPV33 Pr21, HPV33 Pr22, HPV33 Pr23, HPV33 Pr24, HPV33 Pr25, HPV33 Pr26, HPV40 Pr1, HPV45 Pr1 (=SGPP68), HPV45 Pr2, HPV45 Pr3, HPV45 Pr4, HPV45 Pr5, HPV45 Pr11, HPV45 Pr12, HPV45 Pr13, HPV52 Pr1, HPV52 Pr2, HPV52 Pr3, HPV52 Pr4, HPV52 Pr5, HPV52 Pr6, HPV56 Pr1, HPV56 Pr2, HPV56 Pr3, HPV56 Pr11, HPV56 Pr12, HPV58 Pr1, HPV58 Pr2, HPV58 Pr3, HPV58 Pr4, SGPP35, SGPP39, SGPP51 (=HPV51 Pr1), SGPP54, SGPP59, SGPP66, SGPP70 (=HPV70 Pr11), SGPP13, SGPP34, SGPP42, SGPP43, SGPP44, SGPP53, SGPP55, SGPP69, SGPP61, SGPP62, SGPP64, SGPP67, SGPP74 (=HPV74 Pr13), MM4 (=HPV4 Pr11), MM7, MM8, HPV18b Pr1, HPV18b Pr2, HPV31 Vs40-1, HPV31 Vs40-2, HPV31 Vs40-3, HPV34 Pr1, HPV35 Pr1, HPV35 Pr2, HPV35 Pr3, HPV39 Pr1, HPV42 Pr1, HPV42 Pr2, HPV43 Pr1, HPV43 Pr2, HPV43 Pr3, HPV44 Pr1, HPV44 Pr2, HPV44 Pr3, HPV44 Pr4, HPV45 Pr5, HPV51 Pr2, HPV53 Pr1, HPV54 Pr1, HPV54 Pr11, HPV54 Pr11as, HPV54 Pr12, 11HPV55 Pr1, HPV55 Pr11, HPV55 Pr12, HPV55 Pr13, HPV56 Vs74-1, HPV59 Pr1, HPV59 Pr11, HPV59 Pr12, HPV59 Pr13, HPV66 Pr1, HPV67 Pr1, HPV 67Pr11, HPV67 Pr12, HPV67 Pr13, HPV67 Pr21, HPV67 Pr22, HPV67 Pr23, HPV68 Pr1, HPV68 Pr2,HPV68 Pr3, HPV68 Vs45-1, HPV68 Vs45-2, HPV70 Pr1, HPV70 Pr12, HPV70 Pr13, HPV74 Pr1, HPV74 Pr11, HPV74 Pr12, HPV74 Pr2, HPV74 Pr3, HPVM4 Pr1, HPVM4 Pr12, HPVM4 Pr21, HPVM4 Pr22.

The sequences of said probes are shown in table 7 and table 12.

It is to be understood that combinations of the aforementioned embodiments are also preferred embodiments, for instance a method characterized in that said 5'-primer specifically hybridizing to the A region is chosen from the aforementioned respective list and that said 3'-primer specifically hybridizing to the C region is chosen from the aforementioned respective list.

It is an important feature of the present invention that the amplified polynucleic acid fragments of HPV fall within a short region of the L1 gene, a region that presents a high degree of sequence variability. Said region is denoted D region and for any HPV type consists of the region corresponding in a sequence alignment to the region from position 6553 to position 6646 of the genome of HPV 16, with the numbering being according to isolate PPH16, with Genbank accession number K02718. The advantage of amplifying a short fragment is that higher sensitivity can be obtained, i.e. a lower number of copies of HPV polynucleic acids can be detected and/or identified. The aforementioned primers may be used to amplify a fragment of approximately 65 bp (by use of 5'-primers specifically hybridizing to the B region and 3'-primers specifically hybridizing to the C region) or a fragment of approximately 94 bp (by use of 5'-primers specifically hybridizing to the A region and 3'-primers specifically hybridizing to the C region). However, it is obvious to one skilled in the art that other primers may be used in order to amplify other fragments within or overlapping with said D region. Preferred primers are shown in table 1 and in table 4. These primers permit amplification of polynucleic acid fragments of a large group of HPV types, but it may be desirable for some purposes to chose primers that selectively amplify a smaller group of HPV types.

The different types of HPV in a sample can be identified by hybridization of polynucleic acids of said types of HPV to at least one, preferably at least two, more preferably at least three, even more preferably at least four and most preferably at least five oligonucleotide probes. These probes may be designed to specifically hybridize to the D region of only one HPV genome, said D region being indicated in FIG. 1. Tables 7 and 12 contain a list of preferred probes specifically hybridizing to the 22 bp region within said D region, situated between the B region and the C region. These probes may be used together under the same conditions of hybridization and washing, for instance in a LiPA format (see below). Probes that have been optimized to work together in a LiPA format are. for instance the combination of HPV6 Pr1, HPV11 Pr1, HPV16 Pr1, HPV18 Pr1, HPV31 Pr25, HPV31 Pr31, HPV31 Pr32, HPV33 Pr21, HPV33 Pr25, HPV40 Pr1, HPV45 Pr11, HPV45 Pr12, HPV45 Pr13, HPV52 Pr5, HPV52 Pr6, HPV56 Pr11, HPV56 Pr12, HPV58 Pr2, HPV58 Pr3 and HPV58 Pr4 (see example 4), the combination of HPV6 Pr1, HPV11 Pr5, HPV16 Pr1, HPV18 Pr1, HPV18b Pr2, HPV31 Pr31, c31-3, HPV33 Pr21, HPV34 Pr1, HPV35 Pr1, HPV39 Pr1, HPV40 Pr1, HPV42 Pr1, HPV43 Pr3, HPV44 Pr1, HPV45 Pr11, HPV51 Pr2, HPV52 Pr5, HPV53 Pr1, HPV56 Pr12, c56-1, HPV58 Pr2, HPV59 Pr12, HPV66 Pr1, HPV68 Pr1, c68-1, HPV70 Pr12 and HPV74 Pr1, or the combination outlined in example 7. Probes specifically hybridizing to said 22 bp region should permit discrimination of all genital low-risk types including HPV types 6, 11, 34, 40, 42–44, 53, 54, 55, 59, 61, 62, 64, 67, 68, 71 and 74 as well as all genital high-risk types including HPV types 16, 18, 31, 33, 35, 39, 45, 51, 52, 56–58, 66 and 69 (zur Hausen, 1996). It should be clear to one skilled in the art that other probes than those listed in table 7 or 12 may be chosen within said region D, provided that they specifically hybridize to only one HPV-type. It should also be clear that in some cases probes may be chosen that overlap with the primers used in the amplification step. In this case, however, the region of overlap between primer and probe should not be as long as to allow by itself duplex formation under the experimental conditions used. It should furthermore be clear that, if presently unknown types are detected that differ in the D region from all presently known types, the methods of this invention will also enable detection and/or identification of said presently unknown HPV types. The present invention furthermore discloses novel sequences in said 22 bp region, as shown in example 5 and in FIG. 1 (SEQ ID NO 135–153). Probes or primers that are designed to specifically hybridize to these sequences, may be used in a method to detect and/or to identify HPV polynucleic acids comprising any of these sequences, when these polynucleic acids are present in a biological sample.

According to another preferred embodiment of the present invention, probes are used that specifically hybridize to the D region, or more particularly to the E region of more than one HPV type. Examples of such probes are given in table 9 and in table 10. The probes in table 9 have been designed for hybridization in a microtiter plate, e.g. according to the DEIA technique (see below), whereas the probes in table 10 are more suitable for the LiPA technique (see below). These probes hybridize to the E region of more than one HPV type, and hence may be used to detect the presence in a biological sample of any of the types to which they hybridize. It should be clear to one skilled in the art that, according to this embodiment, other probes than those listed in table 9 and table 10 may be chosen within the D region, provided that they hybridize to one or more than one HPV type.

According to another preferred embodiment of the present invention, the aforementioned methods of detection and/or identification of HPV are characterized further in that the hybridization step involves a reverse hybridization format. This format implies that the probes are immobilized to certain locations on a solid support and that the amplified HPV polynucleic acids are labelled in order to enable the detection of the hybrids formed. According to this embodiment, at least one probe, or a set of a least 2, preferably at least 3, more preferably at least 4 and most preferably at least 5 probes is used. When at least 2 probes are used, said probes are meticulously designed in such a way that they specifically hybridize to their target sequences under the same hybridization and wash conditions.

According to an even more preferred embodiment of the present invention, the aforementioned hybridization step is performed according to the LiPA technique. Said technique involves a reverse hybridization assay, characterized in that the oligonucleotide probes are immobilized on a solid support as parallel lines (Stuyver et al., 1993; international application WO 94/12670). The reverse hybridization format and particularly the LiPA format have many practical advantages as compared to other DNA techniques or hybridization formats, especially when the use of a combination of probes is preferable or unavoidable to obtain the relevant information sought.

Alternatively, detection of HPV polynucleic acids in a biological sample may be performed by use of the DNA Enzyme Immuno Assay (DEIA). This method is used for rapid and specific detection of PCR products. PCR products are generated by a primer set, of which either the forward or the reverse primer contain biotin at the 5' end. This allows binding of the biotinylated amplimers to streptavidin-coated microtiter wells. PCR products are denatured by sodium hydroxide, which allows removal of the non-biotinylated strand. Specific labelled oligonucleotide probes (e.g. with digoxigenin) are hybridized to the single-stranded immobilized PCR product and hybrids are detected by enzyme-labelled conjugate and calorimetric methods.

The present invention also relates to sets of oligonucleotides, said sets comprising at least one primer and/or at least one probe that may be used to perform the methods for detection and/or identification of HPV as described above. Preferred primers according to the present invention can for instance be chosen from table 1, table 4 and table 11. Preferred probes are shown in tables 7, 9, 10 and 12. These probes can be optimized to be used together in a given format, e.g. a LiPA format, under the same hybridization and washing conditions. Evidently, when other hybridization conditions would be preferred, all probes should be adapted accordingly by adding or deleting one or more nucleotides at their extremities. It should be understood that these concomitant adaptations should give rise to the same result, namely that the probes still hybridize specifically to their respective type-specific target sequences. Such adaptations may also be necessary if the amplified material is RNA and not DNA as is the case in the NASBA system.

The present invention also relates to diagnostic kits for detection and/or identification of HPV, possibly present in a biological sample, comprising the following components:
(i) at least one suitable primer or at least one suitable primer pair;
(ii) at least one suitable probe, preferably at least 2, more preferably at least 3, even more preferably at least 4 and most preferably at least 5 suitable probes, possibly fixed to a solid support;
(iii) a hybridization buffer, or components necessary for the production of said buffer, or instructions to prepare said buffer;
(iv) a wash solution, or components necessary for the production of said solution, or instructions to prepare said solution;
(v) optionally a means for detection of the hybrids formed;
(vi) optionally a means for attaching the probe(s) to a known location on a solid support.

The following definitions and explanations will permit a better understanding of the present invention.

HPV isolates that display a sequence difference of more than 10% to any previously known type in the combined nucleotide sequences of E6, E7 and L1 genes (Chan et al., 1995, de Villiers, 1994) are classified as different HPV "genotypes". HPV isolates that differ between 2 and 10% are classified as different "subtypes". If the sequence variation is below 2%, the isolates are classified within the same subtype as different "variants". The term "type" when applied to HPV refers to any of the three categories defined above.

The target material in the samples to be analyzed may either be DNA or RNA, e.g. genomic DNA, messenger RNA, viral RNA or amplified versions thereof. These molecules are in this application also termed "polynucleic acids".

Well-known extraction and purification procedures are available for the isolation of RNA or DNA from a sample (e.g. in Sambrook et al.,1989).

The term "probe" according to the present invention refers to a single-stranded oligonucleotide which is designed to specifically hybridize to HPV polynucleic acids.

The term "primer" refers to a single stranded oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5–50 nucleotides long. Specific length and sequence will depend on the complexity of the required DNA or RNA targets, as well as on the conditions at which the primer is used, such as temperature and ionic strength.

The expression "suitable primer pair" in this invention refers to a pair of primers allowing the amplification of part or all of the HPV polynucleic acid fragment for which probes are immobilized.

The term "target sequence" of a probe or a primer according to the present invention is a sequence within the HPV polynucleic acids to which the probe or the primer is completely complementary or partially complementary (i.e. with some degree of mismatch). It is to be understood that the complement of said target sequence is also a suitable target sequence in some cases. Probes of the present invention should be complementary to at least the central part of their target sequence. In most cases the probes are completely complementary to their target sequence. The term "type-specific target sequence" refers to a target sequence within the polynucleic acids of a given HPV type that contains at least one nucleotide difference as compared to any other HPV-type.

"Specific hybridization" of a probe to a region of the HPV polynucleic acids means that, after the amplification step, said probe forms a duplex with part of this region or with the entire region under the experimental conditions used, and that under those conditions said probe does not form a duplex with other regions of the polynucleic acids present in the sample to be analysed. It should be understood that probes that are designed for specific hybridization to a region of HPV polynucleic acids, may fall within said region or may to a large extent overlap with said region (i.e. form a duplex with nucleotides outside as well as within said region). For instance, some of the probes that are shown in table 7 and that are designed for specific hybridization to the 22 bp region between the B and the C regions (FIG. 1), extend up to 5 nucleotides beyond the 3'-end of said 22 bp region and other probes of table 7 extend up to 3 nucleotides beyond the 5'-end of said 22 bp region.

"Specific hybridization" of a primer to a region of the HPV polynucleic acids means that, during the amplification step, said primer forms a duplex with part of this region or with the entire region under the experimental conditions used, and that under those conditions said primer does not form a duplex with other regions of the polynucleic acids present in the sample to be analysed. It should be understood that primers that are designed for specific hybridization to a region of HPV polynucleic acids, may fall within said region or may to a large extent overlap with said region (i.e. form a duplex with nucleotides outside as well as within said region).

Since the current application requires the detection of single base pair mismatches, stringent conditions for hybridization of probes are required, allowing only hybridization of exactly complementary sequences. However, it should be noted that, since the central part of the probe is essential for its hybridization characteristics, possible deviations of the probe sequence versus the target sequence may be allowable towards the extremities of the probe when longer probe sequences are used. Variations are possible in the length of the probes. Said deviations and variations, which may be conceived from the common knowledge in the art, should however always be evaluated experimentally, in order to check if they result in equivalent hybridization characteristics as the exactly complementary probes.

Preferably, the probes of the invention are about 5 to 50 nucleotides long, more preferably from about 10 to 25 nucleotides. Particularly preferred lengths of probes include 10, 11, 12, 13, 14, 15, 16, 17, 18, 19, 20, 21, 22, 23, 24 or 25 nucleotides. The nucleotides as used in the present invention may be ribonucleotides, deoxyribonucleotides and modified nucleotides such as inosine or nucleotides containing modified groups which do not essentially alter their hybridization characteristics.

Probe sequences are represented throughout the specification as single stranded DNA oligonucleotides from the 5' to the 3' end. It is obvious to the man skilled in the art that any of the below-specified probes can be used as such, or in their complementary form, or in their RNA form (wherein T is replaced by U).

The probes according to the invention can be prepared by cloning of recombinant plasmids containing inserts including the corresponding nucleotide sequences, if need be by excision of the latter from the cloned plasmids by use of the adequate nucleases and recovering them, e.g. by fractionation according to molecular weight. The probes according to the present invention can also be synthesized chemically, for instance by the conventional phospho-triester method.

The fact that amplification primers do not have to match exactly with the corresponding target sequence in the template to warrant proper amplification is amply documented in the literature (Kwok et al., 1990). However, when the primers are not completely complementary to their target sequence, it should be taken into account that the amplified fragments will have the sequence of the primers and not of the target sequence. Primers may be labelled with a label of choice (e.g. biotine). The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules known in the art.

The oligonucleotides used as primers or probes may also comprise nucleotide analogues such as phosphorothiates (Matsukura et al., 1987), alkylphosphorothiates (Miller et al., 1979) or peptide nucleic acids (Nielsen et al., 1991; Nielsen et al., 1993) or may contain intercalating agents (Asseline et al., 1984). As most other variations or modifications introduced into the original DNA sequences of the invention these variations will necessitate adaptions with respect to the conditions under which the oligonucleotide should be used to obtain the required specificity and sensitivity. However the eventual results of hybridization will be essentially the same as those obtained with the unmodified oligonucleotides. The introduction of these modifications may be advantageous in order to positively influence characteristics such as hybridization kinetics, reversibility of the hybrid-formation, biological stability of the oligonucleotide molecules, etc.

The term "solid support" can refer to any substrate to which an oligonucleotide probe can be coupled, provided that it retains its hybridization characteristics and provided that the background level of hybridization remains low.

Usually the solid substrate will be a microtiter plate (e.g. in the DEIA technique), a membrane (e.g. nylon or nitrocellulose) or a microsphere (bead) or a chip. Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin, haptens or proteins.

The term "labelled" refers to the use of labelled nucleic acids. Labelling may be carried out by the use of labelled nucleotides incorporated during the polymerase step of the amplification such as illustrated by Saiki et al. (1988) or Bej et al. (1990) or labelled primers, or by any other method known to the person skilled in the art. The nature of the label may be isotopic ($^{32}P$, $^{35}S$, etc.) or non-isotopic (biotin, digoxigenin, etc.).

The "sample" may be any biological material taken either directly from the infected human being (or animal), or after culturing (enrichment). Biological material may be e.g. is scrapes or biopsies from the urogenital tract or any part of the human or animal body.

The sets of probes of the present invention will include at least 1, 2, 3, 4, 5, 6, 7, 8, 9, 10, 11, 12,13,14,15,16, 17,18, 19, 20, 21, 22, 23, 24, 25, 26, 27, 28, 29, 30 or more probes. Said probes may be applied in two or more (possibly as many as there are probes) distinct and known positions on a solid substrate. Often it is preferable to apply two or more probes together in one and the same position of said solid support.

For designing probes with desired characteristics, the following useful guidelines known to the person skilled in the art can be applied.

Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions are explained fisher herein.

**The stability of the [probe:target] nucleic acid hybrid should be chosen to be compatible with the assay conditions. This may be accomplished by avoiding long AT-rich sequences, by terminating the hybrids with G:C base pairs, and by designing the probe with an appropriate Tm. The beginning and end points of the probe should be chosen so that the length and % GC result in a Tm about 2–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be more stable at higher temperatures.

**Conditions such as ionic strength and incubation temperature under which a probe will be used should also be taken into account when designing a probe. It is known that the degree of hybridization will increase as the ionic strength of the reaction mixture increases, and that the thermal stability of the hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

\*\*It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. The degree of stringency is chosen such as to maximize the difference in stability between the hybrid formed with the target and the nontarget nucleic acid. In the present case, single base pair changes need to be detected, which requires conditions of very high stringency.

\*\*The length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly complementary base sequence will normally primarily determine hybrid stability. While oligonucleotide probes of different lengths and base composition may be used, preferred oligonucleotide probes of this invention are between about 5 to 50 (more particularly 10–25) bases in length and have a sufficient stretch in the sequence which is perfectly complementary to the target nucleic acid sequence.

\*\*Regions in the target DNA or RNA which are known to form strong internal structures inhibitory to hybridization are less preferred. Likewise, probes with extensive self-complementarity should be avoided. As explained above, hybridization is the association of two single strands of complementary nucleic acids to form a hydrogen bonded double strand. It is implicit that if one of the two strands is wholly or partially involved in a hybrid that it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization may be greatly increased. Computer programs are available to search for this type of interaction. However, in certain instances, it may not be possible to avoid this type of interaction.

\*\*Standard hybridization and wash conditions are disclosed in the Materials & Methods section of the Examples. Other conditions are for instance 3×SSC (Sodium Saline Citrate), 20% deionized FA (Formamide) at 50° C. Other solutions (SSPE (Sodium saline phosphate EDTA), TMAC (Tetramethyl ammonium Chloride), etc.) and temperatures can also be used provided that the specificity and sensitivity of the probes is maintained. When needed, slight modifications of the probes in length or in sequence have to be carried out to maintain the specificity and sensitivity required under the given circumstances.

In order to identify different HPV types with the selected set of oligonucleotide probes, any hybridization method known in the art can be used (conventional dot-blot, Southern blot, sandwich, etc.). However, in order to obtain fast and easy results if a multitude of probes are involved, a reverse hybridization format may be most convenient. In a preferred embodiment the selected probes are immobilized to a solid support in known distinct locations (dots, lines or other figures). In another preferred embodiment the selected set of probes are immobilized to a membrane strip in a line fashion. Said probes may be immobilized individually or as mixtures to delineated locations on the solid support. A specific and very user-friendly embodiment of the above-mentioned preferential method is the LiPA above-mentioned set of probes is immobilized in parallel lines on a membrane, as further described in Example 4. The HPV polynucleic acids can be labelled with biotine, and the hybrid can then, via a biotine-streptavidine coupling. be detected with a non-radioactive colour developing system.

The term "hybridization buffer" means a buffer allowing a hybridization reaction between the probes and the polynucleic acids present in the sample, or the amplified products, under the appropriate stringency conditions.

The term "wash solution" means a solution enabling washing of the hybrids formed under the appropriate stringency conditions.

Throughout this specification and the claims which follow, unless the context requires otherwise, the word "comprise", and variations such as "comprises" and "comprising", will be understood to imply the inclusion of a stated integer or step or group of stated integers or steps but not to the exclusion of any other integer or step or group of integers or steps.

FIGURE AND TABLE LEGENDS

Figure 1B:
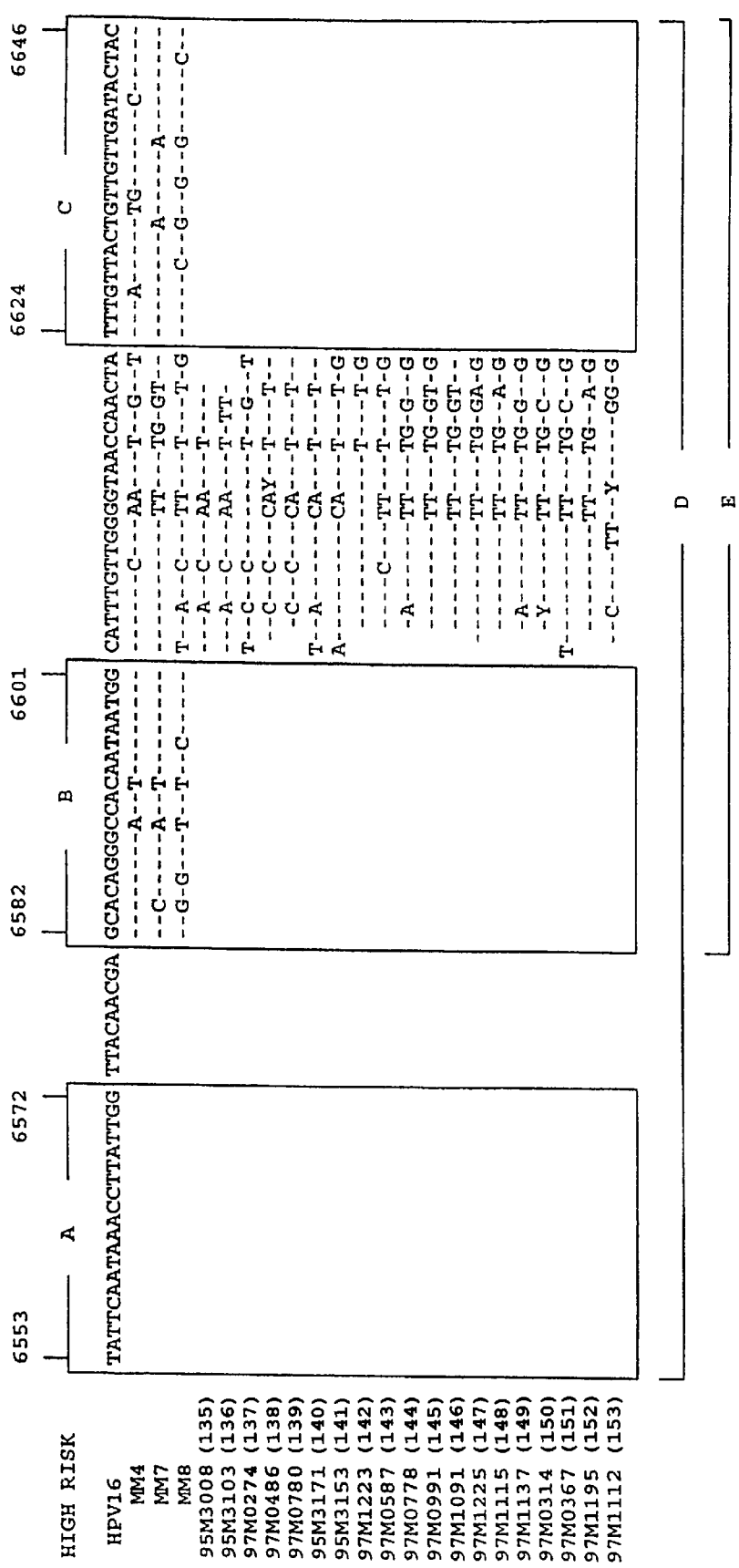

FIGS. 1A and 1B. Alignment of HPV sequences

Alignment of sequences of genital HPV types and previously unknown sequences within the region from position 6553 to position 6646 (numbered according to HPV 16, Genbank locus name PPH16. accession number K02718), denoted region D. Hyphens indicate the presence of identical nucleotides as in HPV 16. The primer target regions A, B and C are boxed. 1) The sequences identified as 95M or 97M followed by a number are novel sequences disclosed by the present invention. The SEQ ID NO of the novel sequences is shown between brackets (HPV16 SEQ ID NO: 312; HPV18 SEQ ID NO: 252; HPV31 SEQ ID NO: 256; HPV33 SEQ ID NO: 258; HPV35 SEQ ID NO: 262; HPV39 SEQ ID NO: 264; HPV45 SEQ ID NO: 274; HPV51 SEQ ID NO: 276; HPV52 SEQ ID NO: 278; HPV56 SEQ ID NO: 286; HPV58 SEQ ID NO: 288; HPV66 SEQ ID NO: 298; HPV69 SEQ ID NO: 304; HPV6 SEQ ID NO: 306; HPV11 SEQ ID NO: 249; HPV34 SEQ ID NO: 260; HPV40 SEQ ID NO: 266; HPV42 SEQ ID NO: 268; HPV43 SEQ ID NO: 270; HPV44 SEQ ID NO: 272; HPV53 SEQ ID NO: 280; HPV54 SEQ ID NO: 282; HPV55 SEQ ID NO: 284; HPV59 SEQ ID NO: 290; HPV61 SEQ ID NO: 292; HPV62 SEQ ID NO: 294; HPV64 SEQ ID NO: 296; HPV67 SEQ ID NO: 300; HPV68 SEQ ID NO: 302; HPV74 SEQ ID NO: 310; HPVMM4 SEQ ID NO: 315; HPVMM7 SEQ ID NO: 317; HPVMM8 SEQ ID 319;).

Figure 2:
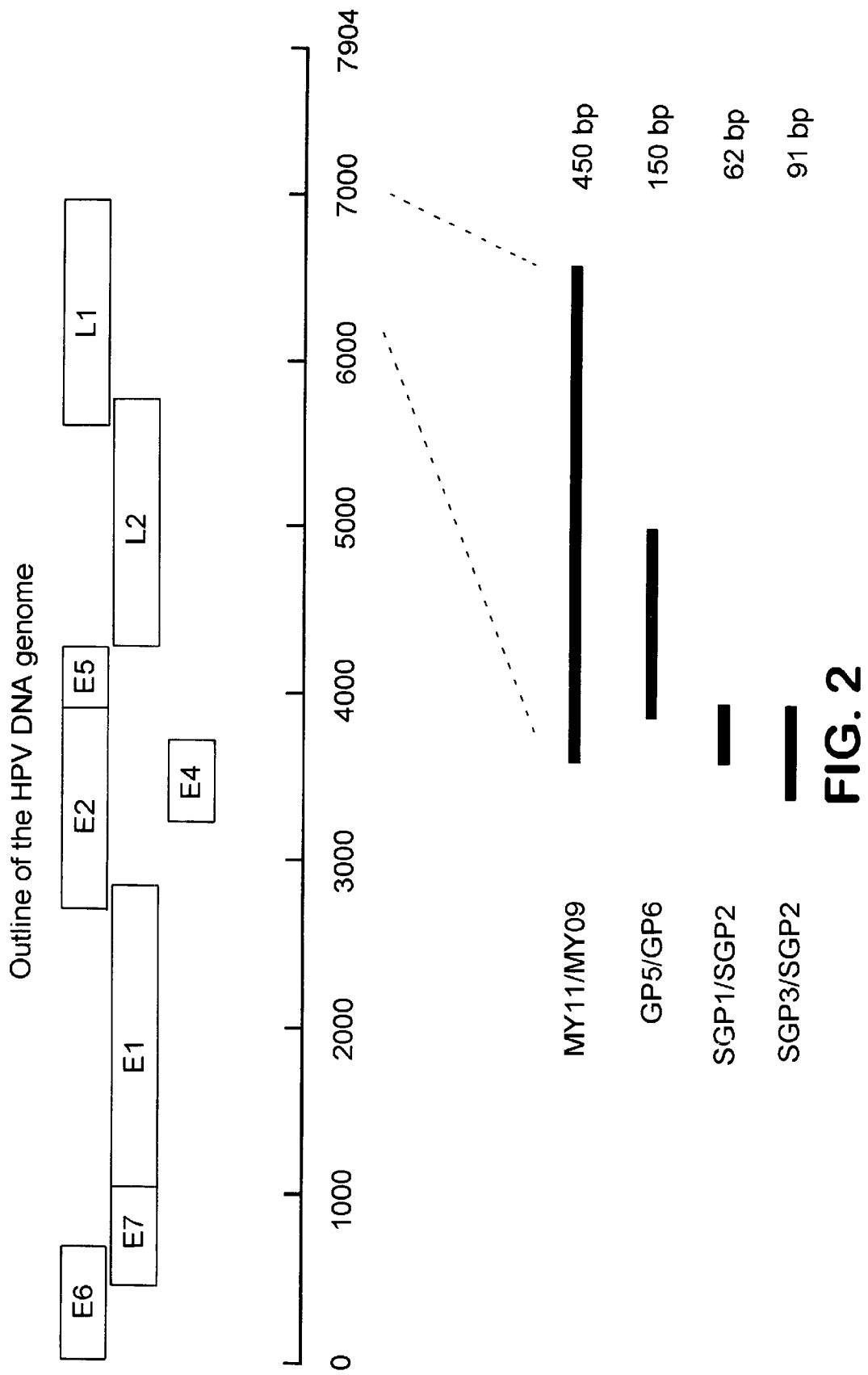

FIG. 2. Outline of the HPV DNA genome

Schematic outline of the HPV genome. The Early (E) and Late (L) antigens are boxed. T he length of the amplimers that can be synthesized by the different general primer sets in the L1 region is shown by a horizontal bar (bp stands for base pairs).

(1)

Region A spans from nucleotide sequence number 6553 to 6572 of HPV 16 (SEQ ID NO: 321), HPV 18 (SEQ ID NO: 322), HPV 31 (SEQ ID NO: 323), HPV 33 (SEQ ID NO: 324), HPV 35 (SEQ ID NO: 325), HPV 39 (SEQ ID NO: 326), HPV 45 (SEQ ID NO: 327), HPV 51 (SEQ ID NO: 328), HPV 52 (SEQ ID NO: 329), HPV 56 (SEQ ID NO: 330), HPV 58 (SEQ ID NO: 331), HPV 6 (SEQ ID NO: 332), HPV 11 (SEQ ID NO: 333), HPV 34 (SEQ ID NO: 334), HPV 40 (SEQ ID NO: 335), HPV 42 (SEQ ID NO: 336), HPV 53 (SEQ ID NO: 337), HPV 54 (SEQ ID NO: 338), HPV 59 (SEQ ID NO: 339), HPV 68 (SEQ ID NO: 340) and HPV 74 (SEQ ID NO: 341).

Region B spans from nucleotide sequence number 6582 to 6601 of HPV 16 (SEQ ID NO: 342), HPV 18 (SEQ ID NO: 343), HPV 31 (SEQ ID NO: 344), HPV 33 (SEQ ID NO: 345), HPV 35 (SEQ ID NO: 346), HPV 39 (SEQ ID NO: 347), HPV 45 (SEQ ID NO: 348), HPV 51 (SEQ ID NO: 349), HPV 52 (SEQ ID NO: 350), HPV 56 (SEQ ID NO: 351), HPV 58 (SEQ ID NO: 352), HPV 66 (SEQ ID NO: 353), HPV 69 (SEQ ID NO: 354), HPV 6 (SEQ ID NO: 355), HPV 11 (SEQ ID NO: 356), HPV 34 (SEQ ID NO: 357), HPV 40 (SEQ ID NO: 358), HPV 42 (SEQ ID NO: 359), HPV 43 (SEQ ID NO: 360), HPV 44 (SEQ ID NO: 361), HPV 53 (SEQ ID NO: 362), HPV 54 (SEQ ID NO: 363), HPV 55 (SEQ ID NO: 364), HPV 59 (SEQ ID NO: 365), HPV 61 (SEQ ID NO: 366), HPV 62 (SEQ ID NO: 367), HPV 64 (SEQ ID NO: 368), HPV 67 (SEQ ID NO: 369), HPV 68 (SEQ ID NO: 370), HPV 74 (SEQ ID NO: 371), HPV MM4 (SEQ ID NO: 372), HPV MM7 (SEQ ID NO: 373) and HPV MM8 (SEQ ID NO: 374).

Region C spans from nucleotide sequence number 6624 to 6646 of HPV 16 (SEQ ID NO: 375), HPV 18 (SEQ ID NO: 376), HPV 31 (SEQ ID NO: 377), HPV 33 (SEQ ID NO: 378), HPV 35 (SEQ ID NO: 379), HPV 39 (SEQ ID NO: 380), HPV 45 (SEQ ID NO: 381), HPV 51 (SEQ ID NO: 382), HPV 52 (SEQ ID NO: 383), HPV 56 (SEQ ID NO: 384), HPV 58 (SEQ ID NO: 385), HPV 66 (SEQ ID NO: 386), HPV 69 (SEQ ID NO: 387), HPV 6 (SEQ ID NO: 388), HPV 11 (SEQ ID NO: 389), HPV 34 (SEQ ID NO: 390), HPV 40 (SEQ ID NO: 391), HPV 42 (SEQ ID NO: 392), HPV 43 (SEQ ID NO: 393), HPV 44 (SEQ ID NO: 394), HPV 53 (SEQ ID NO: 395), HPV 54 (SEQ ID NO: 396), HPV 55 (SEQ ID NO: 397), HPV 59 (SEQ ID NO: 398), HPV 61 (SEQ ID NO: 399), HPV 62 (SEQ ID NO: 400), HPV 64 (SEQ ID NO: 401), HPV 67 (SEQ ID NO: 402), HPV 68 (SEQ ID NO: 403), HPV 74 (SEQ ID NO: 404), HPV MM4 (SEQ ID NO: 405), HPV MM7 (SEQ ID NO: 406) and HPV MM8 (SEQ ID NO: 407).

The region between region B and region C spans from nucleotide sequence number 6602 to 6623 of HPV 16 (SEQ ID NO: 408), HPV 18 (SEQ ID NO: 409), HPV 31 (SEQ ID NO: 410), HPV 33 (SEQ ID NO: 411), HPV 35 (SEQ ID NO: 412), HPV 39 (SEQ ID NO: 413), HPV 45 (SEQ ID NO: 414), HPV 51 (SEQ ID NO: 415), HPV 52 (SEQ ID NO: 416), HPV 56 (SEQ ID NO: 417), HPV 58 (SEQ ID NO: 418), HPV 66 (SEQ ID NO: 419), HPV 69 (SEQ ID NO: 420), HPV 6 (SEQ ID NO: 421), HPV 11 (SEQ ID NO: 422), HPV 34 (SEQ ID NO: 423), HPV 40 (SEQ ID NO: 424), HPV 42 (SEQ ID NO: 425), HPV 43 (SEQ ID NO: 426), HPV 44 (SEQ ID NO: 427), HPV 53 (SEQ ID NO: 428), HPV 54 (SEQ ID NO: 429), HPV 55 (SEQ ID NO: 430), HPV 59 (SEQ ID NO: 431), HPV 61 (SEQ ID NO: 432), HPV 62 (SEQ ID NO: 433), HPV 64 (SEQ ID NO: 434), HPV 67 (SEQ ID NO: 435), HPV 68 (SEQ ID NO: 436), HPV 74 (SEQ ID NO: 437), HPV MM4 (SEQ ID NO: 438), HPV MM7 (SEQ ID NO: 439) and HPV MM8 (SEQ ID NO: 440).

Region E spans from nucleotide sequence number 6582 to 6646 of HPV 16 (SEQ ID NO: 441), HPV 18 (SEQ ID NO: 442), HPV 31 (SEQ ID NO: 443), HPV 33 (SEQ ID NO: 444), HPV 35 (SEQ ID NO: 445), HPV 39 (SEQ ID NO: 446), HPV 45 (SEQ ID NO: 447), HPV 51 (SEQ ID NO: 448), HPV 52 (SEQ ID NO: 449), HPV 56 (SEQ ID NO: 450), HPV 58 (SEQ ID NO: 451), HPV 66 (SEQ ID NO: 452), HPV 69 (SEQ ID NO: 453), HPV 6 (SEQ ID NO: 454), HPV11 (SEQ ID NO: 455), HPV 34 (SEQ ID NO: 456), HPV 40 (SEQ ID NO: 457), HPV 42 (SEQ ID NO: 458), HPV 43 (SEQ ID NO: 459), HPV 44 (SEQ ID NO: 460), HPV 53 (SEQ ID NO: 461), HPV 54 (SEQ ID NO: 462), HPV 55 (SEQ ID NO: 463), HPV 59 (SEQ ID NO: 464), HPV 61 (SEQ ID NO: 465), HPV 62 (SEQ ID NO: 466), HPV 64 (SEQ ID NO: 467), HPV 67 (SEQ ID NO: 468), HPV 68 (SEQ ID NO: 469), HPV 74 (SEQ ID NO: 470), HPV MM4 (SEQ ID NO: 471), HPV MM7 (SEQ ID NO: 472) and HPV MM8 (SEQ ID NO: 473).

Figure 3:
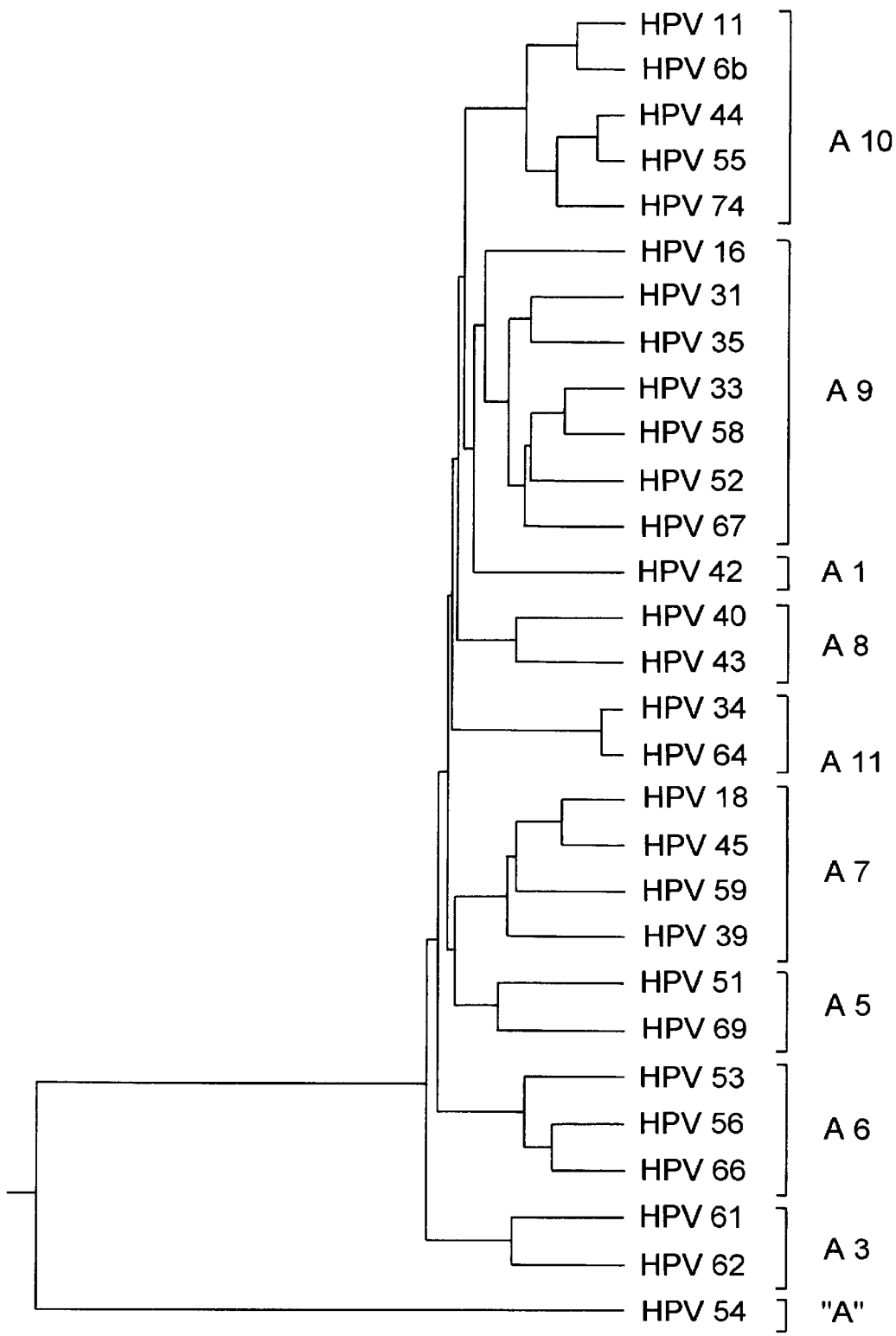

FIG. 3. Phylogenetic tree of HPV sequences in the MY11/MY09 region

Phylogenetic analyses were performed with the Phylip 3.5c software (Felsenstein, 1995). The numbers correspond to the different HPV types; the HPV groups are also indicated.

Figure 4:
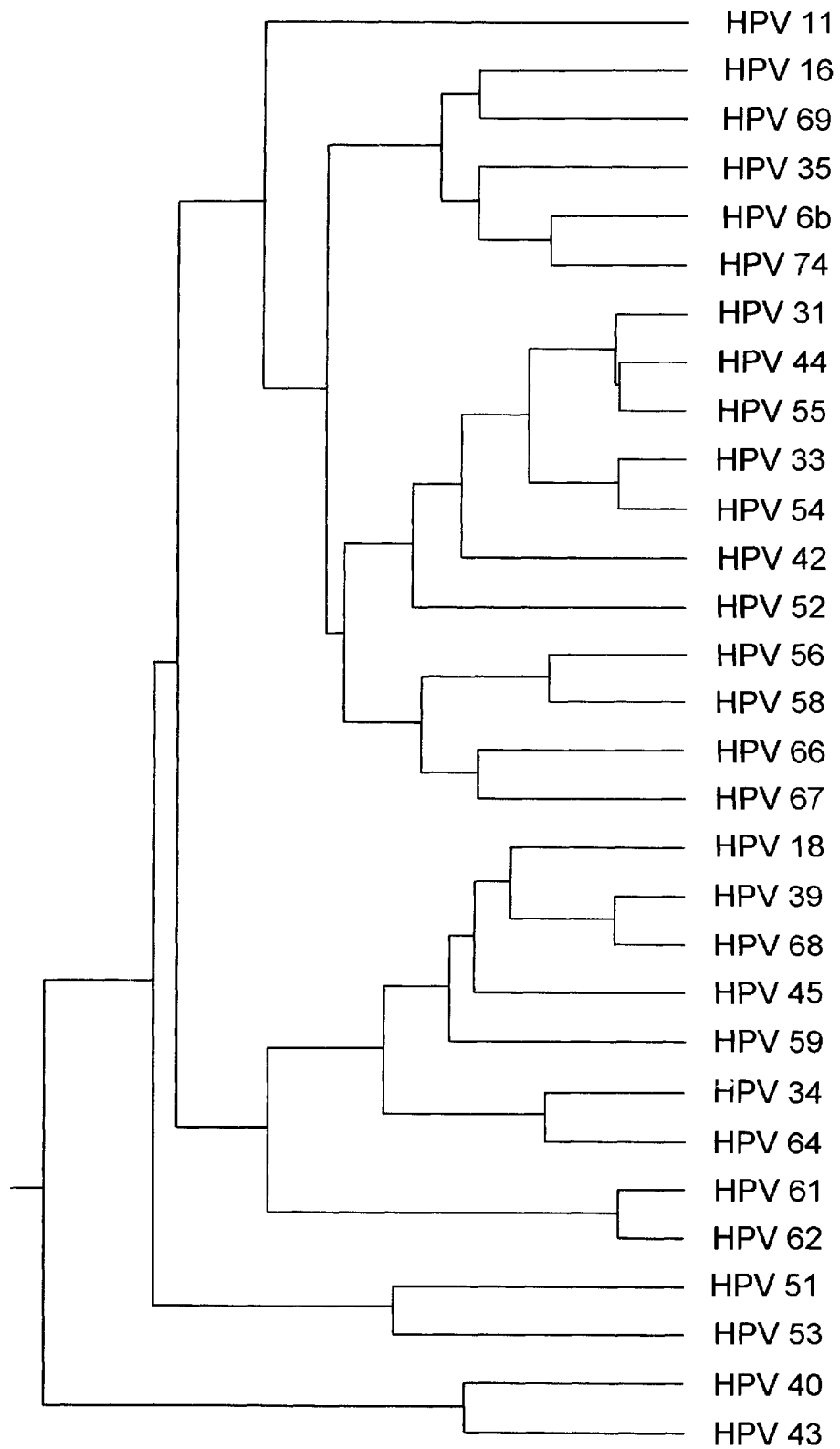

FIG. 4. Phylogenetic tree of HPV sequences between regions B and C.

Phylogenetic analyses of the region between B and C (corresponding to position 6602 to 6623 of HPV 16) were performed with the Phylip 3.5c software (Felsenstein, 1995). The numbers correspond to the HPV types.

Figure 5:
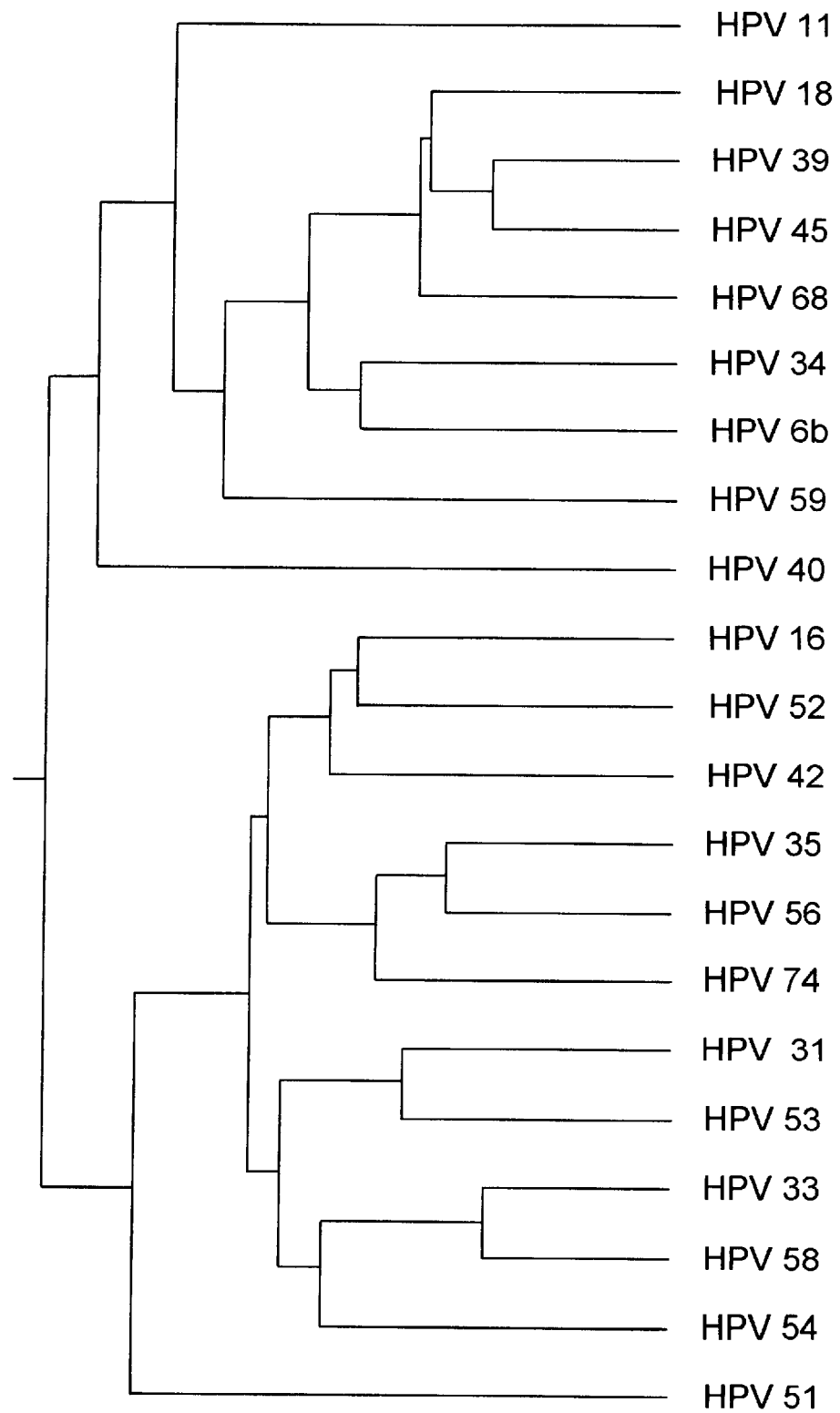

FIG. 5. Phylogenetic tree of HPV sequences between regions A and C.

Phylogenetic analyses of the region between A and C (corresponding to position 6573 to 6623 of HPV 16) were performed with the Phylip 3.5c software (Felsenstein, 1995). The numbers correspond to the HPV types.

Figure 6:
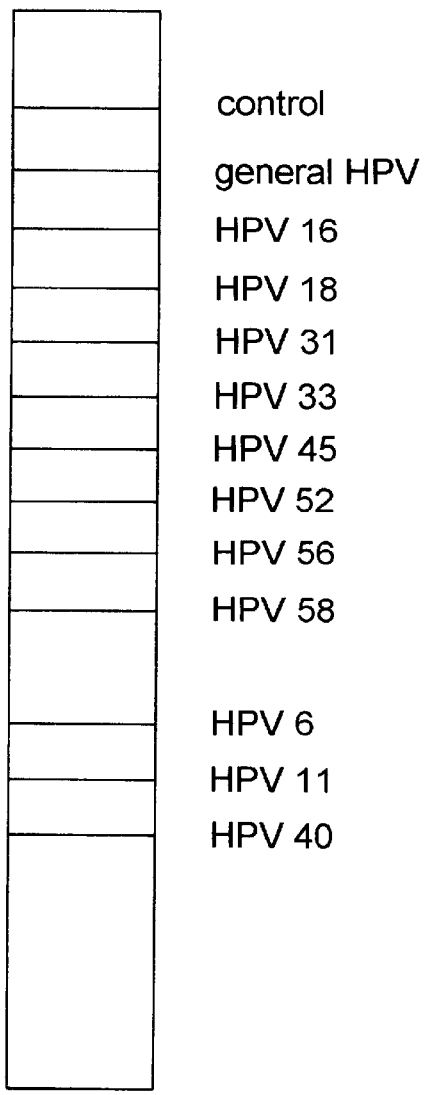

FIG. 6. Outline of a HPV LiPA

The bottom panel shows a possible configuration of a LiPA strip enabling detection and identification of HPV types 16, 18, 31, 33, 45, 6 and 11 (Also, 52,56,58,40). The lines correspond to the positions of type-specific probes. "Control" indicates the position of biotinylated DNA that is used as a control for the conjugate and substrate reaction. "General HPV" indicates the position of probes that enable detection of almost all HPV types. For the amplification step, primers SGP1 and SGP2 can be used; the position of these primers is indicated in the top panel.

Figure 7B:

FIGS. 7A and 7B LiPA experiment

Plasmids containing complete genomic sequences from the HPV types 6, 11, 16, 18, 31, 33 and 45 were subjected to PCR with primer set SGP1-bio/SGP2-bio. Subsequently, the amplimers were analysed in a LiPA assay containing type-specific probes for recognition of the HPV types 6, 11, 16, 18, 31, 33 and 45. The strips A and B contained 5 probes for each of these types, as indicated. Of each probe, two amounts (0.2 and 1 pmol) were present on the strip. The probes for recognition of types 6, 11, 16 and 18 were applied to strip A and those for types 31, 33 and 45 were applied to strip B.

Figure 8B:
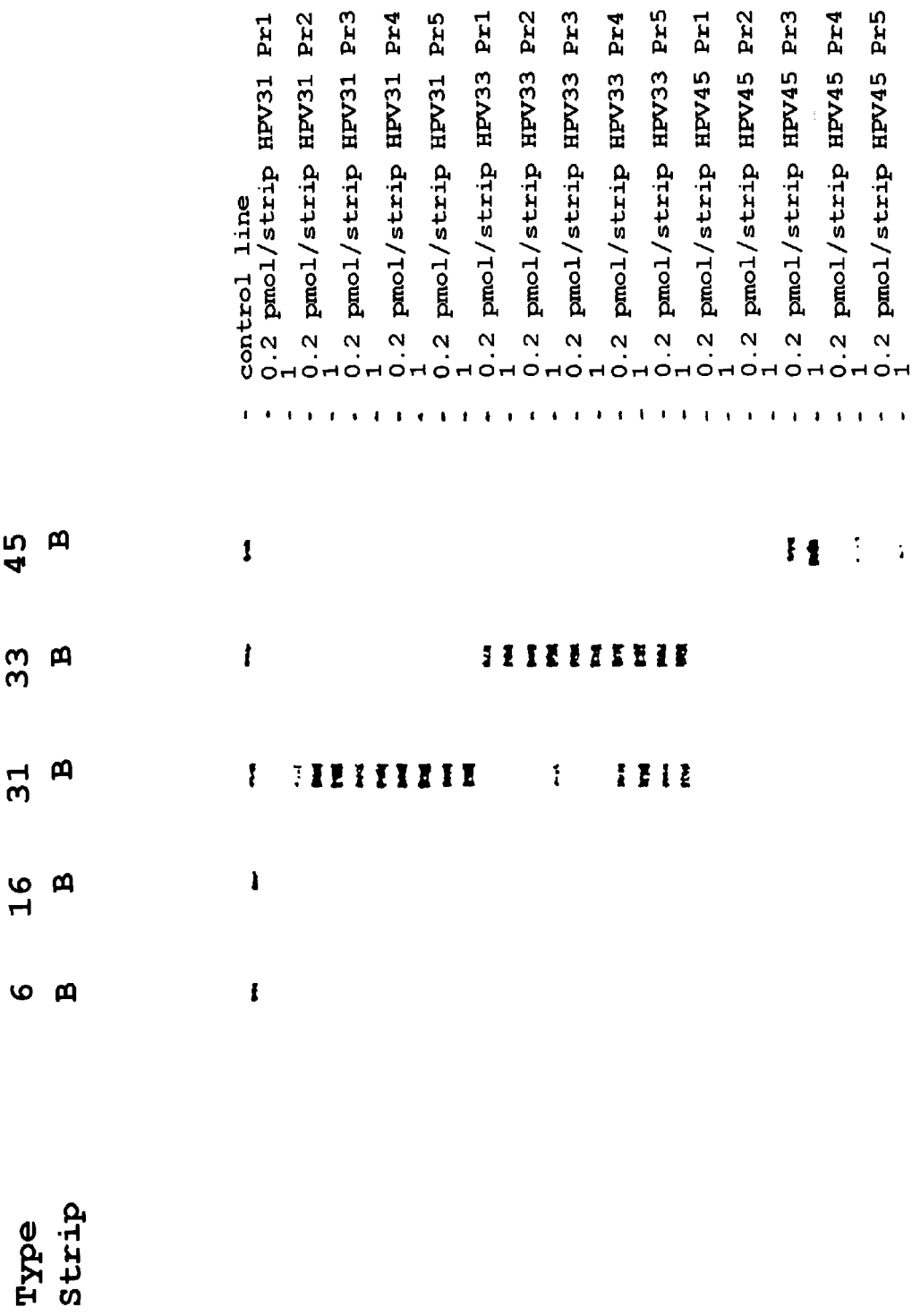

FIGS. 8A & 8B. LiPA experiment

Amplimers synthesized by use of primer set SGP1-bio/MY09-bio from HPV types 6, 16, 31, 33 and 45 were analysed by means of a LiPA experiment. The strip contained 5 probes for each of the types; of each probe two amounts were present. Strip A contains the probes for recognition of types 6, 11, 16 and 18, whereas strip B contains the probes for types 31, 33 and 45.

FIG. 9. Nucleotide Sequence alignments of 39 HPV genotypes

Alignment of HPV sequences within the region from position 6582 to position 6646 (numbered according to HPV 16, GenBank locus name PPH16. accession number K02718). Hyphens indicate the presence of identical nucleotides as in HPV 16. The primer target regions B and C are boxed.

(2) (HPV16 SEQ ID NO: 313; HPV 6 SEQ ID NO: 248; HPV11 SEQ ID NO: 250; HPV13 SEQ ID NO: 251; HPV18 SEQ ID NO: 253; HPV26 SEQ ID NO: 254; HPV30 SEQ ID NO: 255; HPV31 SEQ ID NO: 257; HPV33 SEQ ID NO: 259; HPV34 SEQ ID NO: 261; HPV35 SEQ ID NO: 263; HPV39 SEQ ID NO: 265; HPV40 SEQ ID NO: 267; HPV42 SEQ ID NO: 269; HPV43 SEQ ID NO: 271; HPV44 SEQ ID NO: 273; HPV45 SEQ ID NO: 275; HPV51 SEQ ID NO: 277; HPV52 SEQ ID NO: 279; HPV53 SEQ ID NO: 281; HPV54 SEQ ID NO: 283; HPV55 SEQ ID NO: 285; HPV56 SEQ ID NO: 287; HPV58 SEQ ID NO: 289; HPV59 SEQ ID NO: 291; HPV61 SEQ ID NO: 293; HPV62 SEQ ID NO: 295; HPV64 SEQ ID NO: 297; HPV66 SEQ ID NO: 299; HPV67 SEQ ID NO: 301; HPV68 SEQ ID NO: 303; HPV69 SEQ ID NO: 305; HPV70 SEQ ID NO: 307; HPV72 SEQ ID NO: 308; HPV73 SEQ ID NO: 309; HPV74 SEQ ID NO: 311; HPVMM4 SEQ ID NO: 316; HPVMM7 SEQ ID NO: 318; HPVMM8 SEQ ID NO: 320)

Figure 10:
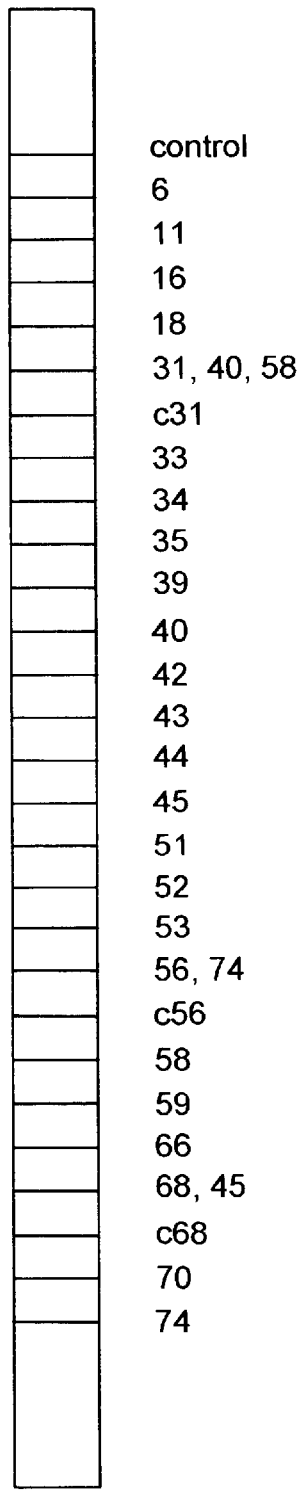

FIG. 10. Outline HPV-LiPA for identification of 25 types

The LiPA strip shows a possible configuration enabling detection and identification of HPV types 6, 11, 16, 18, 31, 33, 34, 35, 39, 40, 42, 43, 44, 45, 51, 52, 53, 54, 56, 58, 59, 66, 68, 70 and 74. The lines correspond to the positions of type-specific probes. "Control" indicates the position of biotinylated DNA that is used as a control for the conjugate and substrate reaction.

Figure 11:
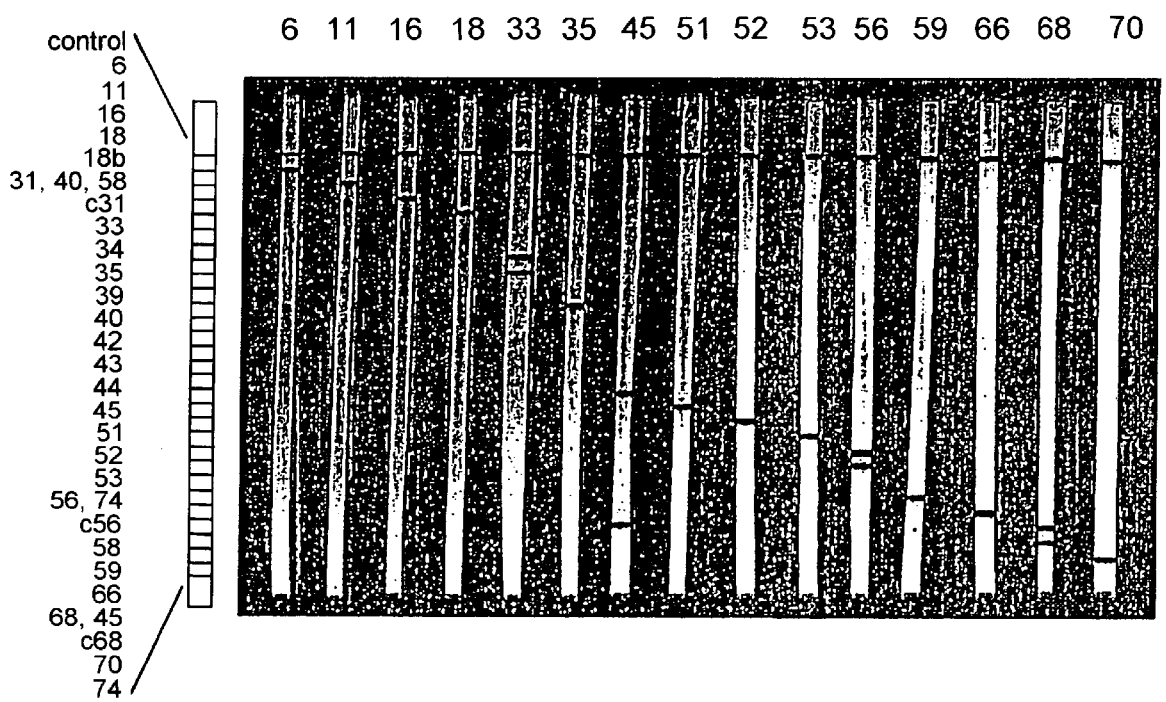

FIG. 11. Typical HPV-LiPA patterns

Plasmids containing genomic sequences of HPV genotypes 6, 11, 16, 18, 33, 35, 45, 51, 52, (2)

Region B spans from nucleotide sequence number 6582 to 6601 of HPV 13 (SEQ ID NO: 474), HPV 26 (SEQ ID NO: 475), HPV 30 (SEQ ID NO: 476), HPV 70 (SEQ ID NO: 477), HPV 72 (SEQ ID NO: 478) and HPV 73 (SEQ ID NO: 479).

Region C spans from nucleotide sequence number 6624 to 6646 of HPV 13 (SEQ ID NO: 480), HPV 26 (SEQ ID NO: 481), HPV 30 (SEQ ID NO: 482), HPV 70 (SEQ ID NO: 483), HPV 72 (SEQ ID NO: 484) and HPV 73 (SEQ ID NO: 485).

The region between region B and region C spans from nucleotide sequence number 6602 to 6623 of HPV 13 (SEQ ID NO: 486), HPV 26 (SEQ ID NO: 487), HPV 30 (SEQ ID NO: 488), HPV 70 (SEQ ID NO: 489), HPV 72 (SEQ ID NO: 490) and HPV 73 (SEQ ID NO: 491).

Region E spans from nucleotide sequence number 6582 to 6646 of HPV 13 (SEQ ID NO: 492), HPV 26 (SEQ ID NO: 493), HPV 30 (SEQ ID NO: 494), HPV 70 (SEQ ID NO: 495), HPV 72 (SEQ ID NO: 496) and HPV 73 (SEQ ID NO: 497). 53, 56, 59, 66, 68, and 70 were subjected to PCR using primers directed to the B and C region in FIG. 9. Subsequently, the amplimers were analysed in a LiPA experiment containing type-specific probes for identification of 25 HPV genotypes. The colored bands indicate hybridization of the amplimer to the type-specific probe.

Table 1 HPV L1 Primers for the A, B and C Regions

Selection of preferred primers specifically hybridizing to the A, B or C regions. HPV16, MY16s and SGP16as represent the corresponding sequence of HPV type 16. MY11 was described by Manos et al. (1989). A + sign indicates that the primer is a sense (forward) primer; a − sign refers to an antisense (reverse) primer.

Table 2 HPV DNA Detection by the Novel General Primers SGP 1/SGP2

Plasmids containing HPV polynucleic acids were subjected to PCR with primer sets SGP1/SGP2 and SGP3/GP6. + indicates that an amplimer was obtained. − indicates that no amplimer was obtained. n.d. indicates that this HPV plasmid was not subjected to PCR with the SGP3/GP6 primer set. An amplimer was obtained for all HPV plasmids with the SGP1/SGP2 primer set, although the amount of PCR-product was different. Sequence analysis revealed that the PCR-product was obtained from the corresponding HPV plasmid and matched the published sequence. Primer set SGP3/GP6 was used to confirm proper isolation of the HPV plasmids.

Table 3 HPV DNA detection by Type-specific Primers and General Primer Sets

To evaluate the efficacy of the novel primers SGP1 and SGP2 in biological samples, 92 formalin-fixed, paraffin-embedded cervical cancer biopsies were tested. A total of 61 out of the 92 biopsies were positive by type-specific PCR. Of these 61 biopsies, 54 contained HPV type 16 and 7 contained HPV type 18. The remaining 31 biopsies were assayed by HPV 31 and HPV 33 type-specific primers and remained negative. These 31 samples, negative by type-specific PCR, were also analyzed by two general primer sets described previously. By using the MY11/MY09 and GP5/GP6 primer sets only 1/31 and 3/31 biopsies were found positive, respectively. All 92 biopsies were found positive by the newly developed SGP 1/SGP2 primerset.

Table 4 HPV L1 Primers for the A, B and C Regions

Selection of preferred primers specifically hybridizing to the A, B or C regions.

Table 5 PCR Amplification with Primers in the B and in the C Region

The specificity of the primers listed in table 4 for the regions B and C was tested on plasmids containing polynucleic acids of HPV types 6, 11, 16, 18, 31, 33, 45, 35, 39, 58, 57 and 59. PCR was performed by all 20 possible primer combinations for the regions B and C. The results are indicated as follows: ±=poor amplification; +=good; ++=very good; blank=no amplification.

Table 6 HPV Genotyping of 77 Isolates by Type-specific PCR and Sequence Analysis of the SGP1/SGP2 Amplimer 77 HPV isolates positive with specific primers for type 16 or 18, were studied for sequence variability in the SGP1/SGP2 amplimer. Samples identified as type 16 by type-specific PCR were all identically typed by sequence analysis of the SGP1/SGP2 amplimer. There was no intratypic sequence variation in the small SGP1/SGP2 amplimer. Identical results were obtained for HPV 18.

Table 7 Type-specific HPV Probes

Selection of preferred probes specifically hybridizing to the 22 bp region between regions B and C. "+" indicates that the probe is a sense probe; "−" refers to an antisense probe. The underlined G or C residues represent non-specific nucleotides that were added to facilitate tailing of the probes.

Table 8 HPV Primers for the Synthesis of Biotinylated PCR Products

SGP1-bio and SGP2-bio are the biotinylated versions of SGP1 and SGP2, shown in table 1. MY09-bio is the biotinylated version of MY09, the sequence of which was disclosed in Manos et al.(1989).

Table 9 Probes for General HPV Detection

Selection of preferred probes that enable detection of more than one HPV type. The types detected by each probe are listed next to the probe.

Table 10 Probes for General HPV Detection
Selection of preferred probes that enable detection of more than one HPV type.

Table 11 PCR Primers
Selection of preferred primers specifically hybridizing to the B or C regions.

Table 12 HPV Type-specific Probes
Selection of preferred probes specifically hybridizing to the region between position 6582–6646 (numbers according to HPV 16, GenBank locus name PPH16, accession number K02718). "+" indicates that the probe is a sense probe; "−" refers to an antisense probe. The underlined residues represent non HPV type-specific nucleotides.

Tables

TABLE 1

HPV L1 primers in the A, B and C regions

| Name | polarity | 5'-sequence-3' | SEQ ID NO/ reference |
|---|---|---|---|
| *A region* | | | |
| HPV16 | + | TATTCAATAAACCTTATTGG | 1 |
| SGP3 | + | -D--T-----R--W------ | 2 |
| SGP3A | + | ----T--------A------ | 3 |
| SGP3B | + | ----T-----G--A------ | 4 |
| *B region* | | | |
| MY16s | + | GCACAGGGCCACAATAATGG | 5 |
| MY11 | + | --M-----W--T--Y----- | Manos et al., 1989 (SEQ ID NO:314) |
| SGP1 | + | --M-----H--T--Y----- | 6 |
| *C region* | | | |
| SGP16as | − | GTATCAACAACAGTAACAAA | 7 |
| SGP2A | − | -----T--C----------- | 8 |
| SGP2 | − | -----H--H----------- | 9 |

D = G, A or T; R = A or G; W = A or T; M = A or C; Y = C or T; H = A, C or T.

TABLE 2

HPV DNA detection by the novel general primers SGP1/SGP2

| HPV plasmid | SGP1/SGP2 | SGP3/GP6[a] | reference[b] |
|---|---|---|---|
| 3 | + | + | Ostrow |
| 4 | + | − | de Villiers |
| 5 | + | + | Ostrow |
| 5/48 | + | − | de Villiers |
| 6 | + | n.d. | de Villiers |
| 7/4 | + | + | de Villiers |
| 7/5 | + | + | de Villiers |
| 8 | + | − | de Villiers |
| 11 | + | + | de Villiers |
| 13 | + | + | de Villiers |
| 16 | + | + | de Villiers |
| 18 | + | + | de Villiers |
| 26 | + | + | Ostrow |
| 27 | + | + | Ostrow |
| 30 | + | + | Orth |
| 31 | + | + | Lörincz |
| 33 | + | n.d. | Orth |
| 35s | + | + | Lörincz |
| 35l | + | + | Lörincz |
| 37 | + | + | de Villiers |
| 39 | + | n.d. | Orth |
| 43s | + | + | Lörincz |
| 43l | + | + | Lörincz |
| 45 | + | + | de Villiers |
| 51 | + | + | de Villiers |
| 52 | + | n.d. | Orth |
| 53 | + | + | de Villiers |
| 56 | + | + | Lörincz |

TABLE 2-continued

HPV DNA detection by the novel general primers SGP1/SGP2

| HPV plasmid | SGP1/SGP2 | SGP3/GP6[a] | reference[b] |
|---|---|---|---|
| 57 | + | + | de Villiers |
| 58 | + | + | Matsukura |
| 59 | + | + | Matsukura |
| 62.2 | + | + | Matsukura |
| 64 | + | + | Matsukura |
| 65 | + | + | de Villiers |
| 67 | + | + | Matsukura |

[a]General primer GP6 (van den Brule et al., 1990)
[b]The HPV plasmids were kindly provided by the Dr's: Lörincz, de Villiers, Matsukura, Ostrow, ter Schegget and Orth.

TABLE 3

HPV DNA detection by type-specific primers and general primer sets

| HPV primer set | number | HPV pos. | HPV neg. | amplimer |
|---|---|---|---|---|
| 16 | 92 | 54 | 38 | 96 bp |
| 18 | 92 | 7 | 85 | 115 bp |
| 31 | 31[a] | 0 | 31 | 110 bp |
| 33 | 31[a] | 0 | 31 | 114 bp |
| MY11/MY09 | 31[b] | 1 | 30 | ±450 bp |
| GP5/GP6 | 31[b] | 3 | 28 | ±142 bp |
| SGP1/SGP2 | 92 | 92 | 0 | 62 bp |

[a]Samples negative by type-specific primers for HPV 16 and 18
[b]Samples negative by type-specific primers for HPV 16, 18, 31 and 33

TABLE 4

HPV L1 primers for the A, B and C regions

| Name | 5'-sequence-3' | SEQ ID NO |
|---|---|---|
| Forward primers region A | | |
| SGP3A | TATTTAATAAACCATATTGG | 3 |
| SGP3B | TATTTAATAAGCCATATTGG | 4 |
| SGP3C | TATTTAATAAGCCTTATTGG | 10 |
| SGP3D | TATTCAATAAACCTTATTGG | 11 |
| SGP3E | TATTTAATAAACCTTACTGG | 12 |
| SGP3F | TATTTAATAAICCITATTGG | 13 |
| SGP3G | TATTTAATAAICCITACTGG | 14 |
| Forward primers region B | | |
| SGP1A | GCICAGGGICACAATAATGG | 15 |
| SGP1B | GCICAGGGICATAACAATGG | 16 |
| SGP1C | GCICAGGGICATAATAATGG | 17 |
| SGP1D | GCICAAGGICATAATAATGG | 18 |
| Reverse primers region C | | |
| SGP2B-bio | bio-GTIGTATCIACAACAGTAACAAA | 19 |
| SGP2C-bio | bio-GTIGTATCTACCACAGTAACAAA | 20 |
| SGP2D-bio | bio-GTIGTATCIACTACAGTAACAAA | 21 |
| SGP2E-bio | bio-GTIGTATCIACGACAGTIACAAA | 22 |
| SGP2F-bio | bio-GTIGTATCIACAACAGTIAIAAA | 23 |

I stands for inosine
"bio-" indicates that the primer is biotinylated

TABLE 5

PCR amplification with primers in the B and in the C region

| Primerset HPV | SGP1C SGP2C-bio | SGP1C SGP2D-bio | SGP1C SGP2E-bio | SGP1C SGP2F-bio | SGP1D SGP2B-bio | SGR1D SGP2C-bio | SGP1D SGP2D-bio | SGP1D SGP2E-bio | SGP1D SGP2F-bio |
|---|---|---|---|---|---|---|---|---|---|
| 6 | ++ | ++ | | ± | + | | ++ | ± | |
| 11 | ++ | ++ | ++ | + | ++ | ± | ++ | + | |
| 16 | | ++ | ++ | ± | ± | | + | | |
| 18 | ++ | ++ | ++ | + | ++ | + | ++ | ++ | |
| 31 | ++ | ++ | ++ | + | ++ | + | ++ | + | |
| 33 | ++ | ++ | ++ | + | ++ | ++ | ++ | ++ | + |
| 45 | ± | + | ± | | + | | ± | | |
| 35 | ± | ++ | ++ | | ++ | ++ | ++ | ++ | + |
| 39 | | ++ | + | | ++ | | ++ | ++ | |
| 58 | ± | + | + | ± | ++ | ++ | ++ | + | |
| 57 | | + | ++ | | + | | + | ++ | |
| 59 | | + | ++ | ± | + | | + | ± | |

| Primerset HPV | SGP1tot SGP2tot-bio | MY11Q SGP2-bio | SGP1AB SGP2BD-bio | SGP1A SGP2B-bio | SGP1A SGP2C-bio | SGP1A SGP2D-bio | SGP1A SGP2E-bio | SGP1A SGP2F-bio | SGP1B SGP2B-bio |
|---|---|---|---|---|---|---|---|---|---|
| 6 | ++ | ++ | ++ | + | | + | + | | ++ |
| 11 | ++ | ± | ++ | ++ | | ++ | + | | ++ |
| 16 | ++ | ++ | ++ | ++ | | ++ | ++ | + | ++ |
| 18 | ++ | ++ | ++ | ++ | + | ++ | ++ | ± | ++ |
| 31 | ++ | ++ | ++ | ++ | ++ | ++ | ++ | + | ++ |
| 33 | ++ | ++ | ++ | ++ | + | ++ | ++ | | ++ |
| 45 | ++ | ++ | ++ | | | | | | ++ |
| 35 | ++ | ± | ++ | + | | ++ | ± | | ± |
| 39 | ++ | ± | ++ | | | + | | + | ± |
| 58 | ++ | ++ | ++ | | | | ± | | ++ |
| 57 | ++ | + | ++ | | | + | | | ++ |
| 59 | ++ | ++ | ++ | ± | | + | ± | | ± |

| Primerset HPV | SGP1B SGP2C-bio | SGP1B SGP2D-bio | SGP1B SGP2E-bio | SGP1B SGP2F-bio | SGP1C SGP2B-bio |
|---|---|---|---|---|---|
| 6 | ++ | ++ | ++ | + | ++ |
| 11 | ++ | ++ | ++ | + | ++ |
| 16 | | + | + | | ++ |
| 18 | ++ | ++ | ++ | + | ++ |
| 31 | + | ++ | ++ | | ++ |
| 33 | + | ++ | ++ | | ++ |
| 45 | | ++ | | | + |
| 35 | | ++ | + | | ++ |
| 39 | | + | + | | + |
| 58 | + | ++ | + | | + |
| 57 | | + | ++ | | + |
| 59 | + | ++ | ++ | ± | + |

TABLE 6

HPV genotyping of 77 isolates by type-specific PCR and sequence analysis of the SGP1/SGP2 amplimer

| HPV-type | type-specific PCR | SGP1/SGP2 |
|---|---|---|
| 16 | 70 | 70 |
| 18 | 7 | 7 |

TABLE 7

Type-specific HPV probes

| Name | 5'-sequence-3' | polarity | SEQ ID NO |
|---|---|---|---|
| HPV6 Pr1 | TTGGGGTAATCAACTGTGG | + | 24 |
| HPV6 Pr2 | GTTGGGGTAATCAACTGTGG | + | 25 |
| HPV6 Pr3 | TTGGGGTSSTCSSCTGTTG | + | 26 |
| HPV6 Pr4 | GTTGGGGTAATCAACTGTTG | + | 27 |
| HPV6 Pr5 | TTGGGGTAATCAACTGTTT | + | 28 |
| HPV11 Pr1 | TGCTGGGGAAACCACTG | + | 29 |
| HPV11 Pr2 | TGCTGGGGAAACCACTTAGG | + | 30 |
| HPV11 Pr3 | TTGTTGGGGAAACCACTG | + | 31 |
| HPV11 Pr4 | TTGCTGGGGAAACCACTTAGG | + | 32 |
| HPV11 Pr5 | TGCTGGGGAAACCACTTGGG | + | 33 |
| HPV16 Pr1 | TTGGGGTAACCAACTATGG | + | 34 |
| HPV16 Pr2 | GTTGGGGTAACCAACTATGG | + | 35 |
| HPV16 Pr3 | TTGGGGTAACCAACTATTG | + | 36 |
| HPV16 Pr4 | GTTGGGGTAACCAACTATTG | + | 37 |
| HPV16 Pr5 | TTGGGGTAACCAACTATTT | + | 38 |
| HPV18 Pr1 | GTGTTTGCTGGCATAAT | + | 39 |
| HPV18 Pr2 | GGTGTTTGCTGGCATAAG | + | 40 |
| HPV18 Pr3 | GTGTTTGCTGGCATAATC | + | 41 |
| HPV18 Pr4 | TGGTGTTTGCTGGCATAAG | + | 42 |
| HPV18 Pr5 | GGTGTTTGCTGGCATAAT | + | 43 |
| HPV31 Pr1 | TTGGGGCAATCAGTTATGG | + | 44 |
| HPV31 Pr2 | GTTGGGGCAATCAGTTATGG | + | 45 |
| HPV31 Pr3 | TTGGGGCAATCAGTTATTG | + | 46 |
| HPV31 Pr4 | GTTGGGGCAATCAGTTATTG | + | 47 |
| HPV31 Pr5 | GTTGGGGCAATCAGTTATTT | + | 48 |

TABLE 7-continued

Type-specific HPV probes

| Name | 5'-sequence-3' | polarity | SEQ ID NO |
|---|---|---|---|
| HPV31 Pr21 | GGGCAATCAGTTATTG | + | 49 |
| HPV31 Pr22 | AATAACTGATTGCCC | – | 50 |
| HPV31 Pr23 | GGCAATCAGTTATTTCC | + | 51 |
| HPV31 Pr24 | AAATAACTGATTGCC | – | 52 |
| HPV31 Pr25 | GCAATCAGTTATTTGG | + | 53 |
| HPV31 Pr26 | CAAATAACTGATTGC | – | 54 |
| HPV31 Pr31 | GGCAATCAGTTATTTGG | + | 55 |
| HPV31 Pr32 | GCAATCAGTTATTGTG | + | 56 |
| HPV33 Pr1 | TTGGGGCAATCAGGTATGG | + | 57 |
| HPV33 Pr2 | GTTGGGGCAATCAGGTATGG | + | 58 |
| HPV33 Pr3 | TTGGGGCAATCAGGTATTG | + | 59 |
| HPV33 Pr4 | GTTGGGGCAATCAGGTATTG | + | 60 |
| HPV33 Pr5 | GTTGGGGCAATCAGGTATTT | + | 61 |
| HPV33 Pr21 | GGGCAATCAGGTATTG | + | 62 |
| HPV33 Pr22 | AATACCTGATTGCCC | – | 63 |
| HPV33 Pr23 | GGCAATCAGGTATTTCC | + | 64 |
| HPV33 Pr24 | AAATAGGTGATTGCCC | – | 65 |
| HPV33 Pr25 | GCAATCAGGTATTTGG | + | 66 |
| HPV33 Pr26 | CAAATACCTGATTGC | – | 67 |
| HPV40 Pr1 | CATATGTTTTGGCAATC | – | 68 |
| HPV45 Pr = SGPP68 | GTATTTGTTGGCATAAT | – | 69 |
| HPV45 Pr2 | GGTATTTGTTGGCATAAG | + | 70 |
| HPV45 Pr3 | GTATTTGTTGGCATAATC | + | 71 |
| HPV45 Pr4 | TGGTATTTGTTGGCATAAG | + | 72 |
| HPV45 Pr5 | GGTATTTGTTGGCATAAT | + | 73 |
| HPV45 Pr11 | TGGCATAATCAGTTGGG | + | 74 |
| HPV45 Pr12 | GGCATAATCAGTTGTG | + | 75 |
| HPV45 Pr13 | GCATAATCAGTTGTTT | + | 76 |
| HPV52 Pr1 | GCAATCAGTTGTTTGC | + | 77 |
| HPV52 Pr2 | CAATCAGTTGTTTGTC | + | 78 |
| HPV52 Pr3 | ATGGCATATGTTGGG | + | 79 |
| HPV52 Pr4 | TGGCATATGTTGGGGG | + | 80 |
| HPV52 Pr5 | GGCATATGTTGGGGC | + | 81 |
| HPV52 Pr6 | GCATATGTTGGGGCA | + | 82 |
| HPV56 Pr1 | GGGGTAATCAATTATC | + | 83 |
| HPV56 Pr2 | GGGGTAATCAATTATTC | + | 84 |
| HPV56 Pr3 | GGGGTAATCAATTATTT | + | 85 |
| HPV56 Pr11 | TGGGGTAATCAATTATTT | + | 86 |
| HPV56 Pr12 | GGGGTAATCAATTATTTGG | + | 87 |
| HPV58 Pr1 | CATTTGCTGGGGCAAG | + | 88 |
| HPV58 Pr2 | ATTTGCTGGGGCAAT | + | 89 |
| HPV58 Pr3 | TTTGCTGGGGCAATC | + | 90 |
| HPV58 Pr4 | TTGCTGGGGCAATCC | + | 91 |
| SGPP35 | GTTGGAGTAACCAATTG | + | 92 |
| SGPP39 | GTATATGTTGGCATAAT | + | 93 |
| SGPP51 = HPV45 Pr1 | GCATTGCTGGAACAAT | + | 94 |
| SGPP54 | GGGGCAATCAGGTGTTT | + | 95 |
| SGPP59 | GGTATATGTTGGCACAA | + | 96 |
| SGPP66 | GCATATGCTGGGGTA | + | 97 |
| SGPP68 = HPV45 Pr1 | GTATTTGTTGGCATAAT | + | 69 |
| SGPP70 = HPV70 Pr11 | CATTTGTTGGCATAACC | + | 99 |
| SGPP13 | TGGGGCAATCACTTG | + | 100 |
| SGPP34 | GCATTTGCTGGCATA | + | 101 |
| SGPP42 | TGGGGAAATCAGCTATT | + | 102 |
| SGPP43 | GGCATTTGTTTTGGGAA | + | 103 |
| SGPP44 | TTGGGGAAATCAGTTATT | + | 104 |
| SGPP53 | GCATCTGTTGGAACAA | + | 105 |
| SGPP55 | GTTGGGGGAATCAGT | + | 106 |
| SGPP69 | GTTGGGGCAACCAATTG | + | 107 |
| SGPP61 | TGGTTTAATGAATTGTTT | + | 108 |
| SGPP62 | GGTTTAATGAACTGTTT | + | 109 |
| SGPP64 | AATGGAATTTGTTGGCA | + | 110 |
| SGPP67 | GTATATGCTGGGGTAAT | + | 111 |
| SGPP74 = HPV74 Pr13 | ATTTGTTGGGGTAATCA | + | 112 |
| MM4 = HPVM4Pr11 | TGCTGGAATAATCAGCT | + | 113 |
| MM7 | TGGTTTAATGAGTTATTT | + | 114 |
| MM | ATATGCTGGTTTAATCA | + | 115 |

TABLE 8

HPV primers for synthesis of biotinylated PCR products.

| Name | polarity | 5'-sequence-3' | SEQ ID NO/reference |
|---|---|---|---|
| SGP1-bio | + | bio-GCMCAGGGHCATAAYAATGG | 6 |
| SGP2-bio | – | bio-GTATCHACHACAHTAACAAA | 9 |
| MY09-bio | – | bio-CGTCCMARRGGAWACTGATC | Manos et al., 1989 |

M = A or C; H = A, C or T; Y = C or T; R = A or G; W = A or T

TABLE 9

Probes for general HPV detection

| Name | 5'-sequence-3'[1] | position[2] | HPV types recognized | SEQ ID NO |
|---|---|---|---|---|
| HPVuni1 | AATAATGGCATITGTTGG | 6594–6611 | 16,30,52,53, 70/MM7,72,43 | 116 |
| HPVuni2 | AATAATGGTATITGTTGG | 6594–661 | 31,33,26,35, 13,42,44,55, 62,73 | 117 |
| HPVuni3 | AACAATGGTATITGTTGG | 6594–6611 | 45,6,59,68, 54.61,39 | 118 |
| HPVuni4 | AACAATGGTATITGCTGG | 6594–6611 | 11,67,MM | 119 |
| HPVuni5 | AACAATGGTGTTTGCTGG | 6594–6611 | 18 | 120 |
| HPVuni6 | AATAATGGCATITGCTGG | 6594–6611 | 51,56,66,MM4 | 121 |
| HPVuni7 | AACAATGGTATITGCTGG | 6594–6611 | 34,57,58 | 122 |
| HPVuni1A | CAIAATAATGGCATITGTTGGC | 6591–6612 | 16,30,52,53, 70,MM7,72,43 | 220 |

TABLE 9-continued

Probes for general HPV detection

| Name | 5'-sequence-3'[1] | position[2] | HPV types recognized | SEQ ID NO |
|---|---|---|---|---|
| HPVuni1B | CAIAACAATGGCATITGTTGGC | 6591–6612 | 16,30,40,52,53,69,70,MM7 72,43 | 221 |
| HPVuni1C | CACAATAATGGCATTTGTTGGGG | 6591–6613 | 16,30,52,53, 70,MM7,72,43 | 222 |
| HPVuni2A | CAIAATAATGGTATITGTTGGG | 6591–6612 | 31,33,26,35, 13,42,44,55, 62,73 | 223 |
| HPVuni3A | CAIAACAATGGTATITGTTGGC | 6591–6612 | 45,6,59,68, 54,61,39 | 224 |

[1] I = inosine
[2] Sequence positions according to HPV genotype 16 sequence PPH16, Genbank accession number K02718
HPV type 64 is theoretically not recognised.

TABLE 10

Probes for general HPV detection

| Name | 5'-sequence-3' | polarity | SEQ ID NO |
|---|---|---|---|
| HPVuni2L2 | CAIAATAATGGTATITGTTGG | + | 123 |
| HPVuni2L3 | AIAATAATGGTATITGTTGG | + | 124 |
| HPVuni2L4 | CAIAATAATGGTATTTGTTGG | + | 125 |
| HPVuni2L5 | AIAATAATGGTATTTGTTGG | + | 126 |
| HPVuni2L6 | CACAATAATGGTATTTGTTGG | + | 127 |
| HPVuni2L7 | ACAATAATGGTATTTGTTGG | + | 128 |
| HPVuni4L1 | CAIAACAATGGTATITGTTGG | + | 129 |
| HPVuni4L2 | AIAACAATGGTATITGTTGG | + | 130 |
| HPVuni4L3 | CAIAACAATGGTATTTGTTGG | + | 131 |
| HPVuni4L4 | AIAACAATGGTATTTGTTGG | + | 132 |
| HPVuni4L5 | ATAACAATGGTATTTGTTGG | + | 133 |
| HPVuni4L6 | ATAACAATGGTATTTGTTGG | + | 134 |
| HPV G1 | AATGGCATTTGTTGGGTAACCAACTATTT | + | 225 |
| HPV G1A1 | TTGTTGGGGTAACCAACTATG | + | 226 |
| HPV G1A2 | ATTTGTTGGGGTAACCAACTATTG | + | 227 |
| HPV G1A3 | GCATTTGTTGGGGTAACCAACTA | + | 228 |
| HPV G1A4 | TGGCATTTGTTGGGGTAACCAACTA | + | 229 |
| HPV G2 | AATGGTATTTTGTTGGGGCAATCAGTTATTT | + | 230 |
| HPV G3 | AATGGTATTTGTTGGCATAATCAGTTGTTT | + | 231 |
| HPV G4 | AATGGTATTTGTTGGTTTAATGAATTGTTT | + | 232 |
| HPV G5 | AATGGCATTTGCTGGAACAATCAGCTTTTT | + | 233 |
| HPV G6 | AATGGTATATGTTGGGGCAATCACTTGTTT | + | 234 |
| HPV R1 | AATGGCATTTGTTGGGC | + | 235 |
| HPV R10 | AATGGCATATGCTGGAATAATC | + | 236 |
| HPV R11 | AATGGTATATGTTGGGCAATC | + | 237 |
| HPV R2 | AATGGTATTTGTTGGGC | + | 238 |
| HPV R3 | AATGGAATTTGTTGGCATAATC | + | 239 |
| HPV R4 | GGTATCTGCTGGCATAAT | + | 240 |
| HPV R5 | AATGGCATTTGTTGGTTTAATG | + | 241 |
| HPV R6 | AATGGTATTTGTTGGTTTAATG | + | 242 |
| HPV R7 | AATGGCATCTGTTGGTTTAATG | + | 243 |
| HPV R8 | TGTTGGTTTAATGAGCTGTG | + | 244 |
| HPV R9 | TGCTGGTTTAATCAATTGTTG | + | 245 |

Underlined sequences are not complementary to HPV.

TABLE 11

PCR primers

| Primer designation | 5'-sequence-3'[1] | position[2] | SEQ ID NO |
|---|---|---|---|
| SGP1A | GCICAGGGICACAATAATGG | 6582–6601 | 15 |
| SGP1B | GCICAGGGICATAACAATGG | 6582–6601 | 16 |
| SGP1C | GCICAGGGICATAATAATGG | 6582–6601 | 17 |
| SGP1D | GCICAAGGICATAATAATGG | 6582–6601 | 18 |
| SGP2B-bio | GTIGTATCIACAACAGTAACAAA | 6624–6646 | 19 |
| SGP2D-bio | GTIGTATCIACTACAGTAACAAA | 6624–6646 | 21 |
| SGP2H-bio | GTIGTATCIACAACTGTAACAAA | 6624–6646 | 98 |
| SGP2I-bio | GTIGTATCIACAACTGTAACAAA | 6624–6646 | 154 |
| SGP2J-bio | GTGGTATCCACAACIGTGACAAA | 6624–6646 | 155 |
| SGP2K-bio | GTAGTITCCACAACAGTAAGAAA | 6624–6646 | 156 |
| SGP2L-bio | GTAGTATCIACAACCACAGTTAAAAA | 6624–6646 | 157 |
| SGP2M-bio | GTIGTATCTACAACIGTTAAAAA | 6624–6646 | 158 |
| SGP2N-bio | GTAGTATCTACAACAAGTAACAAA | 6624–6646 | 159 |
| SGP2P-bio | GTAGTATCAACACAGGTAATAAA | 6624–6646 | 160 |

[3] I = inosine
[2] Sequence positions according to HPV genotype 16 sequence PPH16, Genbank accession number K02718.

TABLE 12

HPV type-specific probes

| HPV PROBE | 5'-sequence-3' | polarity | SEQ ID NO |
|---|---|---|---|
| HPV18b Pr1 | GGTATCTGCTGGCATAAG | + | 161 |
| HPV18b Pr2 | TGGTATCTGCTGGCATA | + | 162 |
| HPV31 Vs40-1 | TATTTGTTGGGGCAATC | + | 163 |
| HPV31 Vs40-2 | ATTTGTTGGGGCAATC | + | 164 |
| HPV31 Vs40-3 | TATTTGTTGGGGCAAT | + | 165 |
| HPV34 Pr1 | GGCATTTGCTGGCATA | + | 166 |
| HPV35 Pr1 | GTTGGAGTAACCAATTGGG | + | 167 |
| HPV35 Pr2 | TGTTGGAGTAACCAATTCC | + | 168 |
| HPV35 Pr3 | TTGTTGGAGTAACCAATG | + | 169 |
| HPV39 Pr1 | GGTATATGTTGGGCATAAT | + | 170 |
| HPV42 Pr1 | GGGGAAATCAGCTATTG | + | 171 |
| HPV42 Pr2 | GGGGAAATCAGCTATTT | + | 172 |
| HPV43 Pr1 | GGCATTTGTTTTGGGAAG | + | 173 |
| HPV43 Pr2 | GCATTTGTTTTGGGAAT | + | 174 |
| HPV43 Pr3 | CATTTGTTTTGGGAATC | + | 175 |
| HPV44 Pr1 | GGGGAAATCAGTTATTG | + | 176 |
| HPV44 Pr2 | GGGGAAATCAGTTATTT | + | 177 |
| HPV44 Pr3 | GGGAAATCAGTTATTT | + | 178 |
| HPV44 Pr4 | TGGGGAAATCAGTTATG | + | 179 |
| HPV45 Pr5 | GGTATTTGTTGGCATAAT | + | 73 |

TABLE 12-continued

HPV type-specific probes

| HPV PROBE | 5'-sequence-3' | polarity | SEQ ID NO |
|---|---|---|---|
| HPV51 Pr1 = SGPP51 | GCATTTGCTGGAACAAT | + | 94 |
| HPV51 Pr2 | CATTTGCTGGAACAATC | + | 180 |
| HPV53 Pr1 | GGCATCTGTTGGAACAA | + | 181 |
| HPV54 Pr1 | GGCAATCAGGTGTTTC | + | 182 |
| HPV54 Pr11 | GGGCAATCAGGTGTTTC | + | 183 |
| HPV54 Pr11as | AAACACCTGATTGCCC | + | 184 |
| HPV54 Pr12 | GGCAATCAGGTGTTTTG | + | 185 |
| HPV55 Pr1 | GGGGGAATCAGTTATTG | + | 186 |
| HPV55 Pr11 | GGGGGAATCAGTTATG | + | 187 |
| HPV55 Pr12 | TGGGGGAATCAGTTATG | + | 188 |
| HPV55 Pr13 | TGGGGGAATCAGTTAG | + | 189 |
| HPV56 Vs74-1 | CATTTGCTGGGGTAAT | + | 190 |
| HPV59 Pr1 | TGGTATATGTTGGCACAA | + | 191 |
| HPV59 Pr11 | GGTATATGTTGGCACAAT | + | 192 |
| HPV59 Pr12 | GTATATGTTGGCACAATC | + | 193 |
| HPV59 Pr13 | TATATGTTGGCACAATC | + | 194 |
| HPV66 Pr1 | GGCATATGCTGGGGTA | + | 195 |
| HPV67 Pr1 | GGTATATGCTGGGGTAAT | + | 196 |
| HPV67 Pr11 | GGTATATGCTGGGGTA | + | 197 |
| HPV67 Pr12 | TGGTATATGCTGGGGT | + | 198 |
| HPV67 Pr13 | ATGGTATATGCTGGGGG | + | 199 |
| HPV67 Pr21 | GGTATATGCTGGGGT | + | 200 |
| HPV67 Pr22 | TGGTATATGCTGGGGG | + | 201 |
| HPV67 Pr23 | AATGGTATATGCTGGG | + | 202 |
| HPV68 Pr1 | TGGTATTTGTTGGCATA | + | 203 |
| HPV68 Pr2 | ATGGTATTTGTTGGCATA | + | 204 |
| HPV68 Pr3 | ATGGTATTTGTTGGCAT | + | 205 |
| HPV68 Vs45-1 | TTGGCATAATCAATTATTT | + | 206 |
| HPV68 Vs45-2 | TTGGCATAATCAATTATTTCG | + | 207 |
| HPV70 Pr1 | GCATTTGTTGGCATAACC | + | 208 |
| HPV70 Pr11 = SGPP70 | CATTTGTTGGCATAACC | + | 99 |
| HPV70 Pr12 | GCATTTGTTGGCATAAC | + | 209 |
| HPV70 Pr13 | CATTTGTTGGCATAAC | + | 210 |
| HPV74 Pr1 | TATTTGTTGGGGTAAT | + | 211 |
| HPV74 Pr11 | ATTTGTTGGGGTAATC | + | 212 |
| HPV74 Pr12 | TTTGTTGGGGTAATCA | + | 213 |
| HPV74 Pr13 = SGPP74 | ATTTGTTGGGGTAATCA | + | 112 |
| HPV74 Pr2 | GTATTTGTTGGGGTAAT | + | 214 |
| HPV74 Pr3 | TATTTGTTGGGGTAATC | + | 215 |
| HPVM4 Pr1 | TTGCTGGAATAATCAGCT | + | 216 |
| HPVM4 Pr11 = MM4 | TGCTGGAATAATCAGCT | + | 113 |
| HPVM4 Pr12 | TGCTGGAATAATCAGC | + | 217 |
| HPVM4 Pr21 | TGCTGGAATAATCAGCTG | + | 218 |
| HPVM4 Pr22 | TGCTGGAATAATCAGCG | + | 219 |

Undelined sequences are not complemetary to HPV.

EXAMPLES

The following examples only serve to illustrate the present invention. These examples are in no way intended to limit the scope of the present invention.

Example 1

Development of Novel General HPV PCR Primers

Introduction

The aim of the present example was to deduce PCR primers that allow general PCR amplification of sequences from multiple HPV types.

Materials and Methods

Design of Primers

HPV sequences were obtained from the GenBank database. Alignment of all available L1 sequences revealed that there are several regions that show a high degree of conservation among the different HPV genotypes. These regions are indicated in FIG. 1 and are designated A,B and C, respectively.

In order to obtain universal amplification of all HPV sequences, several primers were selected in these three regions. The locations and sequences of the different primers are a represented in FIG. 2 and table 1, respectively. Primer combinations from the A (SGP3) and C (SGP2) region and those from the B (SGP1) and C (SGP2) region will yield an expected amplimer of 91 basepairs (bp) or 62 bp, respectively. Type-specific primers for HPV types 16, 18, 31 and 33 were described in Baay et al.(1996). The MY11-MY09 primer set was described in Manos et al. (1989). The GP5/GP6 primer set was described in van den Brule et al. (1990).

DNA Isolation

DNA was isolated from the 92 formalin fixed and paraffin-embedded cervical cancer biopsies by a modified version of the method described by Claas et al (1989). A 10 μm section was collected in a 1.5 ml tube and deparaffinized by 500 μl Xylol. After gently shaking for 2 minutes and centrifugation for 5 minutes the pellet was again treated with 500 μl Xylol. The pellet was washed twice with 500 μl alcohol 96% and once with 500 μl acetone. Subsequently, the pellet was air-dried and treated with a 200 μl proteinase K solution (1 mg/ml) overnight at 37° C.

PCR

The PCR was performed essentially as described by Saiki (1988). Briefly, the final volume of 100 μl contained 10 μl of the isolated DNA, B10 mM Tris-HCl pH 9.0, 50 mM KCl, 2.5 mM $MgCl_2$, 0.1% Triton X-100, 0.01% gelatin, 200 μM of each deoxynucleoside triphosphate, 50 pmol of forward and reverse primer, and 0.25U of SuperTaq (Sphaero Q, Cambridge, United Kingdom). For the MY11/MY09 primerset (Manos et al., 1989) 0.5U SuperTaq was used. PCR conditions were a preheating step for 1 min 94° C. followed by 40 cycles of 1 min 94° C., 1 min 52° C. and 1 min 72° C. For the primerset SGP3/SGP2 the 40 cycles of amplification consisted of 1 min 94° C., 1 min 40° C. and 1 min 72° C. For the primerset GP5/GP6 (van den Brule et al., 1990) the 40 cycles of amplification consisted of and 1 min 94° C., 2 min 40° C. and 1.5 min 72° C. As a control for successful DNA isolation PCR was performed using β-globin primers described by Saiki (1986).

Southern Blot Analysis

The Southern blot hybridization experiments were performed according to standard procedures (Sambrook et al., 1989). Briefly, 20 μl of the PCR-product was electrophoresed on a 2% agarose gel. Amplimers produced by the primer sets SGP1/SGP2 and SGP3/SGP2 were applied on a 3% agarose gel. Subsequently, amplimers were transferred to a nylon membrane (Hybond N+, Amersham, Little Chalfont, United Kingdom) by vacuum blotting in the presence of 0.4N NaOH. The Southern blots were hybridized with a $^{32}P$ 5'-end labeled probe(s) for 16 hours at 42° C. in a solution containing 5×SSC (1×SSC: 15 mM Na-citrate and 150 mM NaCl, pH 7.0), 5×Denhardt's (1×Denhardt: 0.02% bovine serum albumin, 0.02% polyvinyl pyrolidone and 0.02% ficoll), 0.5% SDS, 75 mM EDTA and 0.1 mg/ml herring sperm DNA. Subsequently, the blots were washed twice in 2×SSC/0.1% SDS at 42° C. for 15 minutes. Autoradiography was performed for 3.5 hours using the Kodak X-Omat AR film.

Samples that were negative by type-specific primers were also analyzed by the L1 directed general primer sets MY11/MY09 and GP5/GP6.

Sequence Analysis

PCR products were analyzed by direct sequencing, using a cycle-sequencing kit (Perkin Elmer). Sequences were analyzed by the PC-Gene software (Intelligenetics, USA)

Results

In order to develop a general set of PCR primers that would allow universal amplification of HPV sequences, we aimed at the L1 region. Primers SGP1 and SGP2 were tested on a number of plasmids, containing partial or complete genomic sequences from various HPV types. The results are summarized in table 2. An amplimer was obtained for all HPV plasmids by the SGP1/SGP2 primer set, although the amount of PCR-product was different. Sequence analysis revealed that the PCR-product was obtained from the corresponding HPV plasmid and matched the published sequence. Primer set SGP3/GP6 was used to confirm proper isolation of the HPV plasmids.

To evaluate the efficacy of the novel primers SGP1 and SGP2 in biological samples, 92 formalin-fixed, paraffin-embedded cervical cancer biopsies were tested. DNA isolated from these biopsies was subjected to different PCR assays: 13-globin primers PCO3 and PCO4 (Saiki et al., 1988), SGP1/SGP2, and type-specific PCR for HPV types 16, US 18, 31, and 33. The results are summarized in table 3.
1. All biopsies contained amplifiable DNA as determined with PCR directed to the B-globin gene.
2. A total of 61 (66%) of the 92 biopsies were positive by type-specific PCR. Of these 61 biopsies, 54 contained HPV type 16 and 7 contained HPV type 18. Subsequently, the remaining 31 biopsies were assayed by HPV 31 and HPV 33 type-specific primers and remained negative.
3. The 31 samples, negative by type-specific PCR were also analyzed by two general primer sets described previously (Manos et al., 1989; van den Brule et al., 1990). By using the MY11/MY09 and GP5/GP6 primersets only 1/31 and 3/31 biopsies were found positive, respectively.
4. All 92 biopsies were found positive by the newly developed SGP1/SGP2 primerset.

Discussion

In general, amplification of a small genomic fragment is likely to increase the sensitivity of the PCR. This is of particular importance when using biological samples that contain a very low copy number of HPV. Furthermore, cervical biopsies that have been formalin-fixed and paraffin-embedded are a poor source of amplifiable DNA.

In this high-risk group for HPV, the novel primer combination SGP1/SGP2 was more sensitive than the type-specific PCR and the general PCRs that were also directed to the L1 region of HPV.

In conclusion the newly developed primer sets are highly sensitive for detection of HPV DNA.

Example 2

Optimization of PCR Primers from the A, B and C Region

Introduction

Example 1 describes the selection of semi-conserved regions in the L1 gene of the HPV genome, that permitted the development of a general PCR system. Degenerated primers were used for universal amplification of HPV sequences from different genotypes.

The present example describes the optimization of the primers aimed at these regions. Instead of degenerated primers, this study aimed at the development of several distinct and defined forward and reverse primers.

Materials and Methods

Alignments of L1 sequences were used to deduce PCR primers from the three regions A, B and C (FIG. 1). Primers were tested by PCR in different combinations on plasmids, containing partial or complete genomic inserts from the genital HPV types 6, 11, 16, 18, 31, 33, 35, 39, 43, 45, 51, 52, 53, 56, 57, 58, 59, 62, 64 and 67 as listed in table 2.

HPV DNA amplification was performed according to the following protocol. The final PCR volume of 100 µl contained 10 µl of HPV plasmid DNA, 75 mM Tris-HCl pH 9.0, 20 mM $(NH_4)_2SO_4$, 2,5 mM $MgCl_2$, 0.1% (w/v) Tween 20, 200 µM of each deoxynucleoside triphosphate, 100 pmol of forward and reverse primer, and 3U of Taq-DNA polymerase (Pharmacia, Uppsala, Sweden). After a preheating step for 1 min 94° C. amplification was performed by I min 94° C., 1 min 52° C. and 1 min 72° C. for 40 cycles. Subsequently, PCR products were analyzed on a 3% agarose gel.

Results

Based on the alignments of the L1 sequences as shown in FIG. 1, primers were selected, as shown in table 4. The specificity of the primers in the regions B and C was tested on the plasmids HPV 6, 11, 16, 18, 31, 33, 45, 35, 39, 58, 57 and 59. PCR was performed by all 20 possible primer combinations for the regions B and C and results are summarized in table 5. Poor results were only obtained when using the primer SGP2F-bio that contains an inosine residu at four positions. Although some primer sets had mismatches with the target HPV sequences, amplimers were synthesized for all tested HPV plasmids. From the tested nine primers in the regions B and C, four of them (SGP1A, SGP1B, SGP2B-bio and SGP2D-bio) could be used for efficient HPV amplification. PCR performance of the primer set containing the four primers SGP1A, SGP1B, SGP2B and SGP2D revealed amplification from all tested HPV plasmids: 6, 11, 16, 18, 31, 33, 45, 35, 39, 58, 57 and 59.

Sequence analysis of the amplimers revealed the expected sequence for each plasmid. This result indicates that the four primers are able to detect the various HPV types. The mismatches with especially type 57 and 59 apparently did not hamper amplification.

Discussion

Despite the presence of mismatches between primer and target sequence, successful amplification by PCR may occur if there are no mismatches at the 3' end of the primer. The PCR and sequence data obtained in this study indicate that the primers SGP1A, SGP1B, SGP2B-bio and SGP2D-bio are able to detect efficiently the various HPV genotypes. Therefore, these four primers can be used for universal amplification of HPV.

Example 3

Identification of Different HPV Types by Analysis of a Small PCR Fragment Derived from the L1 Region Introduction Identification of the different HPV genotypes may have great clinical and epidemiological importance. Current classification methods are for instance based on either type-specific PCR or sequence analysis of larger DNA fragments. Therefore, there is a clear need for a simple, rapid and reliable genotyping assay for the different HPV genotypes.

This assay should preferably be combined with the detection of HPV DNA, aiming at the same genomic region. Therefore, we aimed at the development of a screening assay to detect the presence of HPV DNA in clinical samples, and (in case of a positive screening result) the subsequent use of the same amplimer in a genotyping assay. The theoretical requirements for such an assay would be as follows:
1. The amplimer should be small, to allow highly sensitive detection and to permit amplification from formalin-fixed, paraffin-embedded materials. The development of such a PCR assay has been described in examples 1 and 2.

2. The amplified fragment should contain sufficient sequence variation to permit specific detection of the different genotypes. The present study describes: (i) the relationship between sequences from the various HPV types by phylogenetic analyses of the regions MY11/MY09, the sequence between region A and C (51 bp) and between B and C (22 bp); (ii) the analysis of the small amplimer of 62 bp generated by primers from the region B and C; (iii) The development of HPV type-specific probes from this region.

Materials and Methods

1. Sequences from the different HPV genotypes were obtained from the GenBank database.
2. Phylogenetic analyses were performed with the Phylip 3.5c software (Felsenstein 1995).
3. Type-specific HPV PCR and general HPV amplification by SGP1/SGP2 were performed according to the protocol as described in examples 1 and 2.
4. Sequence analysis of the PCR-products was performed by manual sequencing, using the cycle-sequencing kit (Perkin Elmer). Sequences were analyzed by the PC-Gene software (Intelligenetics, USA)

Results

Phylogenetic Analyses

In order to study the relationships between the HPV-derived sequences, several phylogenetic trees were constructed.

1. Sequences between primers MY11 and MY09 were selected from all available HPV sequences. The phylogenetic tree is shown in FIG. 3. Sequence variation in this ±410 bp region permits discrimination between most, if not all HPV genotypes. The different groups of HPV (indicated with an A followed by a number) are indicated in the figure (Chan et al., 1995).
2. Sequences between the regions A and C and those between B and C were also subjected to phylogenetic analysis, and both trees are shown in the FIG. 4 and FIG. 5, respectively. Sequence variation enclosed by the primers in regions B and C (22bp) allows discrimination between the genital HPV types. HPV68 (a genital type) and HPV73 (an oral type) show an identical sequence in this region. However these two types can be recognized in the region flanked by primers in the regions A and C, for instance by use of probes HPV 68 (SEQ ID NO: 246) (CAGGGACACAACAATG) and HPV 73 (SEQ ID NO: 247) (C AGGGTCATAACAATGG).

Intratypic Variation

Since the aim of this study is to determine whether the intratypic sequence variation in the small PCR product is sufficient to identify the different HPV genotypes, the intratypic variation should also be investigated. Therefore, 77 HPV isolates positive with specific primers for type 16 or 18, were studied for sequence variability in the SGP1/SGP2 amplimer. Samples identified as type 16 by type-specific PCR were all identically typed by sequence analysis of the SGP1/SGP2 amplimer (table 6). There was no intratypic sequence variation in the small SGP1/SGP2 amplimer. Identical results were obtained for HPV 18. Sequence analysis of the SGP1/SGP2 amplimers in the group of 31 samples negative by HPV type-specific PCR, as described in example I, revealed different HPV sequences. The obtained sequences were identical to HPV types 16 (n=9), 18 (n=4), 31 (n=2), 35 (n=1), 45 (n=5), 52 (n=2), 56 (n=3) and 58 (n=2). This indicates that PCR with SGP1/SGP2 is more sensitive than HPV type-specific PCRs. Aberrant sequences, not matching any known HPV type, were found in three cases. It was not possible to amplify these isolates by other previously described general primer sets (MY11/MY09, GP5/GP6 and CPI/CPIIg). For these samples the HPV specificity was confirmed by performing a semi-nested PCR with the primer sets SGP3/SGP2 and SGP1/SGP2.

Discussion

Phylogenetic analyses of the various HPV types revealed heterogeneity in the region between primers SGP1 and SGP2. Sequence variation was found to be sufficient for consistent discrimination between all genital HPV types. In order to investigate the reproducibility of this region for HPV genotyping, 77 samples were typed by type-specific PCR and sequence analysis of the SGP1/SGP2 amplimer. No intratypic variation was observed in the SGP1/SGP2 amplimers.

From these results and that of already reported sequences, in particular HPV type 16 variants, it might be suggested that intratypic variability in the 22 bp between the SGP1 and SGP2 primers is very limited. This observation supports the use of sequence variation in the SGP1/SGP2 amplimer for HPV genotyping.

Example 4

Development of the HPV INNO-LiPA Genotyping Assay

Introduction

An aim of the invention was to develop a simple and reliable system for detection as well as identification of HPV genotypes. A possible format of such a system could comprise a single PCR using universal primers, that amplify a small genomic fragment with very high sensitivity. Subsequently, the same PCR product can be used to discriminate between the HPV genotypes. For analysis of the PCR products, sequence analysis is a very accurate method, but it is not very convenient. Therefore we aimed at the development of type-specific probes, that would permit positive recognition of the different HPV genotypes.

Materials and Methods

Selection of Probes

Based on the 22 bp sequences located between the regions B and C (FIG. 1), a number of type-specific probes were proposed. These probes are listed in table 7.

HPV Plasmids and Clinical Isolates

The selected probes were analysed for analytical and clinical specificity. First, plasmids, containing complete genomic sequences of different HPV types, were used as target for PCR amplification with primers SGP1-bio and SGP2-bio, and with primers SGP1-bio and a MY09-bio.

PCR Reactions

PCR was performed using the primer sets SGP1-bio/SGP2-bio and SGP1-bio/MY09-bio. All primers contained a biotic moiety at the 5' end (table 8). The PCR conditions were similar to those described in example 1. The final volume of 100 µl contained 10 µl of plasmid DNA, 75 mM Tris-HCl pH 9.0, 20 mM $(NH_4)_2SO_4$ 2,5 mM $MgCl_2$ 0.1% (w/v) Tween 20, 200 µM of each deoxynucleoside triphosphate, 100 pmol of forward and reverse primer, and 3U of Taq-DNA polymerase (Pharmacia, Uppsala, Sweden). After a preheating step for 1 min 94° C. amplification was performed by 1 min 94° C., 1 min 52° C. and 1 min 72° C. for 40 cycles.

Development of a Reverse Hybridization Format

In order to permit analysis of multiple probes in a single hybridization step, a reverse hybridization assay was developed. This requires the selection of type-specific probes that have very similar hybridization characteristics. For this experiment probes were chosen for HPV types 6, 11, 16, 18, 31, 33 and 45.

Oligonucleotide probes were provided with a poly-(dT) tail at the 3' end. Twenty pmol primer was incubated in 25µl buffer containing 3.2 mM dTTP, 25 mM Tris-HCl (pH 7.5), 0.1 M sodium cacodylate, 1 mM $CoCl_2$, 0.1 mM dithiothreitol and 60 U terminal desoxynucleotidyl transferase for 1 h at 37° C. The reaction was stopped by adding 2.5 µl 0.5 M EDTA (pH 8.0) and diluted with 20×SSC (Sambrook et al., 1989), until a final concentration of 6×SSC and 2.5 pmol oligonucleotide/µl was reached. The tailed probes were immobilized on a nitrocellulose strip as parallel lines. As a control for the conjugate, biotinylated DNA was also applied. A possible outline of the strip is shown in FIG. 6.

Ten µl of the PCR amplification product, containing biotin at the 5' end of each 5 primer, was mixed with 10 µl of denaturation solution (400 mM NaOH, 10 mM EDTA) and incubated at room temperature for 10 minutes. After denaturation of the DNA, 1 ml of preheated hybridization buffer, 3×SSC, 0.1% SDS, (1×SSC: 15 mM Na-citrate and 150 mM NaCl) was added. The hybridization was performed at 50° C. in a shaking waterbath for 1 h. The strips were washed once with hybridization buffer at 50° C. for 30 minutes. The strips were then washed by rinse solution (phosphate buffer containing NaCl, Triton and 0.5% $NaN_3$). Alkaline phosphatase labelled streptavidin was added in conjugate diluent (phosphate buffer containing NaCl, Triton, protein stabilizers and 0.1% $NaN_3$) and incubated at 37° C. for 1 h. Strips were washed again three times with rinse solution and once with substrate buffer (Tris buffer containing NaCl and $MgCl_2$). Colour development was achieved by addition of BCIP and NBT in substrate buffer and incubation for 30 minutes at room temperature. Colour development was stopped by incubation in water and drying of the strips. Reverse hybridization results were interpreted visually.

Results and Discussion

In order to develop a novel HPV typing assay, we selected probes from a small part of the L1 region. This approach would first require detection of HPV sequences in general by PCR using universal primers, such as SGP1/SGP2, generating a fragment of 62 bp or MY11/MY09, generating a fragment of approximately 450 bp. Subsequently, the same PCR product can be analysed using type-specific probes from this L1 region. PCR fragments of 62 bp and 450 bp were generated by primer sets SGP1-bio/SGP2-bio and SGP1-bio/MY09-bio, respectively from different target DNA.

First, plasmids containing complete genomic sequences from the HPV types 6; 11, 16, 18, 31, 33 and 45 were subjected to PCR with primerset SGP 1-bio/SGP2-bio. Subsequently, the amplimers were analysed in the reverse hybridization assay containing type-specific probes for recognition of the HPV types 6, 11, 16, 18, 31, 33 and 45. Representative results of reverse hybridization are shown in FIG. 7. Secondly, amplimers synthesized by the primerset SGP1-bio/MY09-bio from HPV types 6, 16, 31, 33 and 45 were analysed in the reverse hybridization assay (FIG. 8).

The results show that the method has a high sensitivity and allows detection of HPV sequences at very low concentrations or from difficult clinical materials, such as formalin-fixed, paraffin-embedded biopsies. The reverse hybridization method permits positive identification of the main HPV genotypes 6, 11, 16, 18, 31, 33 and 45. This assay can easily be extended by adding probes on the strip for recognition of all other genital HPV genotypes.

Example 5

Sequencing of HPV Isolates

Introduction

In this study, the sequence of HPV isolates in the region between primers SGP1 and SGP2 was analyzed.

Materials and Methods

DNA was isolated from formalin-fixed and paraffin-embedded cervical cancer biopsies and cytologically abnormal scrapes according to standard protocols. PCR was performed as described in example 1 by the use of primers SGP1 and SGP2. The obtained amplimers were analyzed by direct sequencing.

Results

Sequencing of HPV-positive samples revealed that, within the region between primers SGP1 and SGP2, 19 sequences from different patients were aberrant from previously described full-length HPV types. These previously unknown sequences are listed in FIG. 1. Sequences having an identification number starting with 95, were found in cervical cancer biopsies, whereas those starting with 97 were found in cytologically abnormal scrapes.

Discussion

Any of the 19 sequences disclosed in this study may be representative for a new HPV type. Further investigation will be carried out to determine whether indeed any of these sequences is characteristic of a new HPV type that is possibly clinically important. Probes that specifically hybridize to these sequences can be used to detect and/or to identify the corresponding HPV types according to the methods of the present invention.

Example 6

Broad-spectrum Detection of HPV by Amplification of a Short PCR Fragment Using a Mixture of 10 HPV Primers Introduction The examples 1 and 2 describe the selection and optimization of a novel HPV PCR primerset. The selected primers from example 2, SGP1A, SGP1B, SGP2B-bio and SGP2D-bio, could be used for efficient HPV amplification. Additional broad spectrum primers were developed for a more sensitive HPV DNA PCR assay. The current example describes the use of a mixture of 10 primers for highly sensitive detection of human papillomaviruses.

Materials and Methods

From alignments of HPV L1 sequences as shown in FIG. 1, forward and reverse primers were selected for sensitive amplification of HPVs, see table 11. The primers were tested on plasmids containing HPV genotypes 6, 13, 16, 18, 26, 34, 35, 39, 40, 42, 43, 51, 52, 53, 54, 55, 68, 69, 70, 74. These HPV plasmids were provided by Dr. E-M. de Villiers, Heidelberg, Germany (HPV genotypes 6, 13, 16, 18, 40, 51 and 53), Dr. R. Ostrow, Minneapolis, Minn. (HPV genotype 26), Dr. A. Lorincz, Silver Springs, Md. (HPV genotypes 35 and 43), Dr. T. Matsukura, Tokyo, Japan (HPV genotype 69), and Dr. G. Orth, Paris, France (HPV genotypes 34, 39, 42, 52, 54, 55, 68, 70 and 74).

HPV DNA amplification was performed in a final reaction volume of 50 µl, containing 10 µl of small amounts of plasmid DNA, 10 mM Tris-HCl pH 9.0, 50 MM KCl, 2.5 mM $MgCl_2$, 0.1% Triton X-100, 0.01% gelatin, 200 mM of each deoxynucleoside triphosphate, 15 pmol of each forward (SGP1A-1D) and 15 pmol of different reverse primers, and 1.5 U of AmpliTaq gold (Perkin Elmer, Branchburg, N.J., USA). The PCR conditions were as follows: preheating for 9 min 94° C. was followed by 40 cycles of 30 seconds 94° C., 45 seconds at 50° C. or 52° C. or 55° C. and 45 seconds at 72° C., and a final extension of 5 min at 72° C. PCR-products were analyzed on a 3% TBE agarose gel.
Results Developed were 14 broad spectrum primers, 4 sense (SGP1A, SGP1B, SGP1C, SGP1D) and 10 antisense (SGP2B-bio, SGP2D-bio, SGP2H-bio, SGP2I-bio, SGP2J-bio, SGP2K-bio, SGP2L-bio, SGP2M-bio, SGP2N-bio, SGP2P-bio), respectively. See table 11 for sequences and positions. For selection of sensitive PCR primers, plasmid DNA from HPV genotypes 6, 13, 16, 18, 26, 34, 35, 39, 40, 42, 43, 51, 52, 53, 54, 55, 68, 69, 70 and 74 were used as target. PCR experiments were performed with the 4 sense primers (SGP1A, SGP1B, SGP1C, SGP1D) in combination with one or more reverse primers at different annealing temperatures, using low amounts of HPV plasmid DNA. The reverse primers SGP2H-bio, SGP2I-bio, SGP2L-bio and SGP2N-bio appeared to have no added value compared to a mixture of the remaining 6 reverse primers (SGP2B-bio, SGP2D-bio, SGP2J-bio, SGP2K-bio, SGP2M-bio and SGP2P-bio) as listed in table 11. Although the sequences of the 10 primers, 4 sense (SGP1A-1D) and 6 antisense (SGP2B-bio, SGP2D-bio, SGP2J-bio, SGP2K-bio, SGP2M-bio and SGP2P-bio) showed minor mismatches compared to known HPV genotypes (FIG. 1), still low amounts of HPV DNA could efficiently be amplified.
Discussion A mixture of 10 primers was developed for broad-spectrum detection of HPV. Despite minor mismatches between primer and target sequences of known HPVs, the 10 selected primers were succesfull to detect various HPV genotypes at low levels. Therefore, this mixture of 10 primers can be used for sensitive broad-spectrum detection of HPV.

Example 7

A Line Probe Assay for Rapid Detection and Simultaneous Identification of 25 Different HPV Genotypes Introduction Example 4 describes the development of the HPV INNO-LiPA genotyping assay for simple detection and identification of HPV genotypes. This example describes an HPV INNO-LiPA genotyping assay for simultaneous detection and identification of 25 types. After universal HPV amplification, synthesized amplimers can be detected and identified by hybridization to type-specific probes that are applied on a LiPA strip.

Materials and Methods

Based on the inner primer sequence of 22 bp which is located between the regions B and C (FIG. 9), several type-specific probes were proposed and tested for specificity reasons. The selected probes are listed in tables 7 and 12. Plasmids containing HPV sequences of different genotypes were used as target for broad-spectrum amplification (see examples 4 and 6). LiPA experiments were performed as described in example 4 using the Auto-LiPA system.

Results

Amplimers obtained from well defined plasmids containing HPV sequences of various genotypes were used in LiPA experiments in order to determine the specificity of the selected probes (tables 7 and 12). Subsequently, 25 HPV type-specific probes and another 3 probes were selected for simultaneous identification of 25 different HPV genotypes. The outline of the HPV-LiPA is shown in FIG. 10 and typical LiPA patterns are shown in FIG. 1.

In most cases the probe name is directly linked to the HPV type (e.g. a purple color on probe lane 16 means hybridization of an amplimer derived from HPV type 16). The probes c31, c56 and c68 are secundairy probes. These probes are of interest when there is a positive. hybridization with the probe line just above (31/40/58 or 56/74 or 68/45). These 'c' probes were developed for exclusion of type 40, 58, 74, and 45. Those types are also identified by positive hybridization. The 'c' probes c31, c56 and c68 will also react with other types. Amplimers from type 33 and 54 will give a positive reaction with probe c31. Similarly, the amplimer from type 58 hybridizes with c56. Therefore, amplimers of type 58 will give three bands on a LiPA strip (positive on: 31/40/58 and c56 and 58). Probe c68 is also reactive with amplimers from type 18 and 39. HPV type 6 is identified by hybridization to the probes 6. HPV type 74 is identified by the probes 56/74 and 74. A sample contains type 54 when probe c31 is positive while probes 31/40/58, 33,40, and 58 are negative.

Discussion

The described HPV LiPA genotyping assay detects and identifies simultaneously the HPV genotypes 6, 11, 16, 18, 31, 33, 34, 35, 39, 40, 42, 43, 44, 45, 51, 52, 53, 54, 56, 58, 59, 66, 68, 70, and 74. These genotypes can be recognized after universal PCR using the novel developed primerset as described in this patent and the MY11/09 primerset which is discussed in example 4. This typing assay can still be extended with type-specific probes for recognition of other HPV genotypes.

In summary, the novel PCR system for highly sensitive detection of HPV DNA in diverse clinical materials followed by a HPV LiPA typing experiment could be a usefull tool to improve the molecular diagnosis and epidemiology of HPV infections.

REFERENCES

Baay, M. F. D., W. G. V. Quint, J. Koudstaal, H. Hollema, J. M. Duk, M. P. M. Burger, E. Stolz, and P. Herbrink. 1995. Comprehensive study of several general and type-specific primer pairs for detection of human papillomavirus DNA by PCR in paraffin-embedded cervical carcinomas. 34:745–747.

Claas, E. C. J., W. J. G. Melchers, H. C. van der Linden, J. Lindeman, and W. G. V. Quint. 1989. Human papillomavirus detection in parafinn embedded cervical carcinomas and metastases of the carcinomas by the polymerase chain reaction. Am. J. Pathol. 135:703–709.

Cornelissen, M. T. E., J. G. van den Tweel, A. P. H. B. Struyk, M. F. Jebbink, M. Briët, J. van der Noordaa, and J. ter schegget. 1989. Localization of human pappilomavirus type 16 DNA using the polymerase chain reaction in the cervix uteri of women with cervical intraepithelial neoplasia J. Gen. Virol. 70:2555–2562.

Cox, J. Th., A. T. Lorincz, M. H. Schiffman, M. E. Sherman, A. Cullen, and R. J. Kurman. Human papillomavirus testing by hybrid capture appears to be useful in triaging women with a cytological diagnosis of atypical squamous cells of undetermined significance.

de Villiers, E.-M. 1989. Heterogeneity in the human papillomavirus group. J. Virology 63:4898–4903.

de Villiers, E.-M. 1994. Human pathogenic papiliomavirus types: an update. Curr. Top; Microbiol. 186: 1–12.

Evander, M., and G. Wadell. 1991. A general primer pair for amplification and detection of genital human papillomavirus types. J. Virol. Methods 31:239–250.

Falcinelli, C., E. Claas, B. Kleter, and W. G. V. Quint. 1992. Detection of the human papillomavirus type 16 mRNA-transcripts in cytological abnormal scrappings. J. Med. Virol. 37:93–98.

Garson, J. A., C. J. A. Ring, and P. W. Tuke. 1991. Improvement of HCV genome detection with "short" PCR products. Lancet 338:1466–1467.

Manos, M. M., Y. Ting, D. K. Wright, A. J. Lewis, T. R. Broker, and S. M. Wolinsky. 1989. The use of polymerase chain reaction amplification for the detection of genital human papillomaviruses. Cancer Cells 7:209–214.

Newton, C. R., A. Graham, L. E. Heptinstall, S. J. Powell, C. Summers, N. Kalsheker, J. C. Smith, and A. F. Markham. 1989. Analysis of any point mutation in DNA. The amplification refractory mutation system (ARMS). Nucleic Acids Research 17:2503–2516.

Ohara, Y., M. Honma, and Y. Iwasaki. 1992. Sensitivity of the polymerase chain reaction for detecting human T-cell leukemia virus type I sequences in paraffin-embedded tissue: Effect of unbuffered formalin fixation. J. Virol. Methods 37:83–88.

Remmink, A. J., J. M. M. Walboomers, T. J. M. Helmerhorst, F. J. Voorhorst, L. Roozendaal, E. K. J. Risse, C. J. L. M. Meijer, and P. Kenemans. 1995. The presence of persistence high-risk HPV genotypes in dysplastic cervical lesions is associated with progressive disease: Natural history up to 36 months. Int. J. Cancer 61:16.

Saiki, R. K., D. H. Gelfland, S. Stoffel, S. J. Scharf, R. Higuchi, G. T. Horn, K. B. Mullis, and H. A. Erlich. 1988. Primer-directed enzymatic amplification of DNA with a thermostable DNA polymerase. Science 239:487–491.

Saiki, R. K., T. L. Bugawan, G. T. Horn, K. B. Mullis, and H. A. Erlich. 1986. Analysis of enzymatically amplified b-globin and HLA-DQ-alfa DNA with allele-specific oligonucleotide probes. Nature 324:163–166.

Sambrook et al. 1989 Molecular Cloning: A Laboratory Manual, 2nd Edition, Cold Spring Harbour Laboratory Press Sommer, R., and D. Tautz. 1989. Minimal homology requirements for PCR primers. Nucleic Acids Research 17:6749.

Stuyver, L., R. Rossau, A. Wyseur, M. Duhamel, B. Vanderborght, H. Van Heuverswyn, and G. Maertens. 1993. Typing of hepatitis C virus isolates and characterization of new subtypes using a line probe assay. J. Gen. Virol. 74:1093–1102.

Tieben L. M., J. ter Schegget, R. P. Minnaar, J. N. Bouwes Bavinck, R. J. M. Berkhout, B. J. Vermeer, M. f. Jebbink, and H. L. Smits. 1993. Detection of cutaneous and genital HPV types in clinical samples by PCR using consensus primers. J. Virol. Methods 42:265–280.

Van den Brule, A. J. C., P. J. F. Snijders, R. L. J. Gordijn, O. P. Bleker, C. J. L. M. Meijer, and J. M. M. Walboomers. 1990. General primer-mediated polymerase chain reaction permits the detection of sequenced and still unsequenced human papillomavirus genotypes in cervical scrapes and carcinomas. Int. J. Cancer 45:644–649.

Young, L. S., I. S. Bevan, M. A. Johnson, P. I. Blomfield, T. Bromidge, N. J. Maitland, and G. B. J. Woodman. 1989. The polymerase chain reaction: A new epidemiological tool for investigatiing cervical human papillomavirus infection. Brit. Med. J. 298:14–18.

Woodworth, C. D., Waggoner, S., Barnes, W., Stoler, M. H., Di Paolo, J. A. 1990. Human cervical and foreskin eptithelial cells immortalized by human Papillomavirus DNAs exhibit displastic differentiation in vivo. Cancer Res. 50: 3709–3715.

What is claimed is:

1. A method for detection and/or identification of HPV present in a biological sample, comprising:

(i) amplifying a nucleic acid fragment of HPV using:

(a) a 5' primer that specifically hybridizes to the A region or B region of the genome of at least one HPV type, and, (b) a 3' primer that specifically hybridizes to the C region of the genome of at least one HPV type, to obtain amplified fragments;

(ii) hybridizing the amplified fragments from step (i) with at least one probe that specifically hybridizes to the D region of at least one HPV type; and (iii) detecting hybrids formed in step (ii).

2. The method according to claim 1, wherein the A region has a sequence selected from the group consisting of SEQ ID NOS: 321–340 and 341.

3. The method according to claim 1, wherein the B region has a sequence selected from the group consisting of SEQ ID NOS: 342–374, 474–478, and 479.

4. The method according to claim 1, wherein the C region has a sequence selected from the group consisting of SEQ ID NOS: 375–407, 480–484, and 485.

5. The method according to claim 1, wherein said 5' primer that specifically hybridizes to the A region consists essentially of a polynucleotide having a sequence selected from the group consisting of: SEQ ID NO:2, SEQ ID NO:3, SEQ ID NO:4, SEQ ID NO:10, SEQ ID NO:11, SEQ ID NO:12, SEQ ID NO:13, and SEQ ID NO: 14.

6. The method according to claim 1, wherein said 5' primer that specifically hybridizes to the B region consists essentially of a polynucleotide having a sequence selected from the group consisting of: SEQ ID NO:6, SEQ ID NO:15, SEQ ID NO:16, SEQ ID NO:17, and SEQ ID NO:18.

7. The method according to claim 1, wherein said 3' primer that specifically hybridizes to the C region consists essentially of a polynucleotide having a sequence selected from the group consisting of: SEQ ID NO:9, SEQ ID NO:8, SEQ ID NO:19, SEQ ID NO:20, SEQ ID NO:21, SEQ ID NO:22, SEQ ID NO:23, SEQ ID NO:98, SEQ ID NO:154, SEQ ID NO:155, SEQ ID NO:156, SEQ ID NO:157, SEQ ID NO:158, SEQ ID NO:159, and SEQ ID NO:160.

8. The method according to claim 1, wherein said probe consists essentially of a polynucleotide having a sequence selected from the group consisting of: SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO: 48, SEQ ID NO: 49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO: 70, SEQ ID NO:71, SEQ ID NO: 72, SEQ ID NO: 73, SEQ ID NO:74, SEQ ID NO:75, SEQ ID NO: 76, SEQ ID NO:77, SEQ ID NO:78, SEQ ID NO:79, SEQ ID NO: 80, SEQ ID NO: 81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:161, SEQ ID NO:162, SEQ ID NO:163, SEQ ID NO:164, SEQ ID NO:165, SEQ ID NO:166, SEQ ID NO:167$_1$, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO: 181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO: 215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, SEQ ID NO:240, SEQ ID NO:241, SEQ ID NO:242, SEQ ID NO:243, SEQ ID NO:244, SEQ ID NO:245.

9. The method according to claim 1, wherein said A region spans from nucleotide sequence number 6553 to 6572 of HPV16 (SEQ ID NO:321), said B region spans from nucleotide sequence number 6582 to 6601 of HPV16 (SEQ ID NO:342), and said C region spans from nucleotide sequence number 6624 to 6646 of HPV16 (SEQ ID NO:375); or wherein said A region spans from nucleotide sequence number 6553 to 6572 of HPV18 (SEQ ID NO:322), said B region spans from nucleotide sequence number 6582 to 6601 of HPV18 (SEQ ID NO:343), and said C region spans from nucleotide sequence number 6624 to 6646 of HPV18 (SEQ ID NO:376); or wherein said A region spans from nucleotide sequence number 6553 to 6572 of HPV31 (SEQ ID NO:323), said B region spans from nucleotide sequence number 6582 to 6601 of HPV31 (SEQ ID NO:344), and said C region spans from nucleotide sequence number 6624 to 6646 of HPV31 (SEQ ID NO:377); or wherein said A region spans from nucleotide sequence number 6553 to 6572 of HPV33 (SEQ ID NO:324), said B region spans from nucleotide sequence number 6582 to 6601 of HPV33 (SEQ ID NO:345), and said C region spans from nucleotide sequence number 6624 to 6646 of HPV33 (SEQ ID NO:378); or wherein said A region spans from nucleotide sequence number 6553 to 6572 of HPV35 (SEQ ID NO:325), said B region spans from nucleotide sequence number 6582 to 6601 of HPV35 (SEQ ID NO:346), and said C region spans from nucleotide sequence number 6624 to 6646 of HPV35 (SEQ ID NO:379); or wherein said A region spans from nucleotide sequence number 6553 to 6572 of HPV39 (SEQ ID NO:326), said B region spans from nucleotide sequence number 6582 to 6601 of HPV39 (SEQ ID NO:347), and said C region spans from nucleotide sequence number 6624 to 6646 of HPV39 (SEQ ID NO:380); or wherein said A region spans from nucleotide sequence number 6553 to 6572 of HPV45 (SEQ ID NO:327), said B region spans from nucleotide sequence number 6582 to 6601 of HPV45 (SEQ ID NO:348), and said C region spans from nucleotide sequence number 6624 to 6646 of HPV45 (SEQ ID NO:381); or wherein said A region spans from nucleotide sequence number 6653 to 6572 of HPV51 (SEQ ID NO:328), said B region spans from nucleotide sequence number 6582 to 6601 of HPV51 (SEQ ID NO:349), and said C region spans from nucleotide sequence number 6624 to 6646 of HPV51 (SEQ ID NO:382); or wherein said A region spans from nucleotide sequence number 6653 to 6572 of HPV52 (SEQ ID NO:329), said B region spans from nucleotide sequence number 6582 to 6601 of HPV52 (SEQ ID NO:350), and said C region spans from nucleotide sequence number 6624 to 6646 of HPV52 (SEQ ID NO:383); or wherein said A region spans from nucleotide sequence number 6653 to 6572 of HPV56 (SEQ ID NO:330), said B region spans from nucleotide sequence number 6582 to 6601 of HPV56 (SEQ ID NO:351), and said C region spans from nucleotide sequence number 6624 to 6646 of HPV56 (SEQ ID NO:384); or wherein said A region spans from nucleotide sequence number 6653 to 6572 of HPV58 (SEQ ID NO:331), said B region spans from nucleotide sequence number 6582 to 6601 of HPV58 (SEQ ID NO:352), and said C region spans from nucleotide sequence number 6624 to 6646 of HPV58 (SEQ ID NO:385); or wherein said B region spans from nucleotide sequence number 6582 to 6601 of HPV66 (SEQ ID NO:353), and said C region spans from nucleotide sequence number 6624 to 6646 of HPV66 (SEQ ID NO:386); or wherein said B region spans from nucleotide sequence number 6582 to 6601 of HPV69 (SEQ ID NO:354), and said C region spans from nucleotide sequence number 6624 to 6646 of HPV69 (SEQ ID NO:387).

10. The method according to claim 1, wherein the 3'-end of said 5'-primer that specifically hybridizes to the A region corresponds to position 6572 of the genome of HPV 16 (SEQ ID NO: 312), or to the corresponding position of any other HPV genome, and/or, the 3'-end of said 5'-primer that specifically hybridizes to the B region corresponds to position 6601 of the genome of HPV 16 (SEQ ID NO: 312) or to the corresponding position of any other HPV genome, and/or, the 3-end of said 3'-primer that specifically hybridizes to the C region corresponds to position 6624 of the genome of HPV 16 (SEQ ID NO: 312) or to the corresponding position of any other HPV genome.

11. The method according to claim 1, wherein said D region is selected from the group consisting of: SEQ ID NO: 312, SEQ ID NO: 252, SEQ ID NO: 256, SEQ ID NO: 258, SEQ ID NO: 262, SEQ ID NO: 264, SEQ ID NO: 274, SEQ ID NO: 276, SEQ ID NO: 278, SEQ ID NO: 286, SEQ ID NO: 288, SEQ ID NO: 298, SEQ ID NO: 304, SEQ ID NO: 306, SEQ ID NO: 249, SEQ ID NO: 260, SEQ ID NO: 266, SEQ ID NO: 268, SEQ ID NO: 270, SEQ ID NO: 272, SEQ ID NO: 280, SEQ ID NO: 282, SEQ ID NO: 284, SEQ ID NO: 290, SEQ ID NO: 292, SEQ ID NO: 294, SEQ ID NO: 296, SEQ ID NO: 300, SEQ ID NO: 302, SEQ ID NO: 310, SEQ ID NO: 315, SEQ ID NO: 317, and SEQ ID NO: 319.

12. The method according to claim 1, wherein said probe that specifically hybridizes with the D region more particularly hybridizes to the E region, wherein said E region is a subregion of the D region.

13. The method according to claim 1, wherein said probe that specifically hybridizes with the D region hybridizes only to one HPV type.

14. The method according to claim 1, wherein said probe that specifically hybridizes with the D region hybridizes to more than one HPV type.

15. The method according to claim 13, wherein said probe that hybridizes only to one HPV type specifically hybridizes to a 22 bp region situated between the B region and C region.

16. The method according to claim 15, wherein said 22 bp region has a sequence selected from the group consisting of SEQ ID NOS: 135–153, 408–440, 486–490, and 491.

17. The method according to claim 12, wherein the E region has a sequence selected from the group consisting of SEQ ID NOS: 441–473, 492–496, and 497.

18. The method according to claim 12, wherein said probe that specifically hybridizes with the E region hybridizes only to one HPV type.

19. The method according to claim 18, wherein said probe has a sequence selected from the group consisting of: SEQ ID NOS: 24–115, 161–218, and 219.

20. The method according to claim 12, wherein said probe that specifically hybridizes with the E region hybridizes to more than one HPV type.

21. The method according to claim 20, wherein said probe has a sequence selected from the group consisting of: SEQ ID NOS: 116–134, 220–244, and 245.

22. The method according to claim 1, wherein said probe is a polynucleotide having a nucleotide sequence that is the complement of a sequence selected from the group consisting of SEQ ID NOS: 135–153, 408–440, 486–490, and 491.

23. A primer combination comprising a first oligonucleotide that specifically binds to the A region of at least one HPV type, wherein said A region has a sequence selected from the group consisting of SEQ ID NOS: 321–340 and 341, and a second oligonucleotide that specifically binds to the C region of at least one HPV type, wherein said C region has a sequence selected from the group consisting of SEQ ID NOS: 375–407, 480–484, and 485.

24. A primer combination comprising a first oligonucleotide that specifically binds to the B region of at least one HPV type, wherein said B region has a sequence selected from the group consisting of SEQ ID NOS: 342–374, 474–478, and 479, and a second oligonucleotide that specifically binds to the C region of at least one HPV type, wherein said C region has a sequence selected from the group consisting of SEQ ID NOS: 375–407, 480–484, and 485.

25. A diagnostic kit for the detection and/or identification of HPV present in a biological sample, comprising:

(a) a 5' primer that specifically hybridizes to the A region or B region of the genome of at least one HPV type, and, (b) a 3' primer that specifically hybridizes to the C region of the genome of at least one HPV type, and (c) at least one probe that specifically hybridizes to the D region of at least one HPV type.

* * * * *

SEQUENCE LISTING

<160> NUMBER OF SEQ ID NOS: 497

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer derived from the Human
      Papillomavirus (HPV)

<400> SEQUENCE: 1
tattcaataa accttattgg                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer derived from the Human
      Papillomavirus (HPV)

<400> SEQUENCE: 2
tdtttaataa rccwtattgg                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer derived from the Human
      Papillomavirus (HPV)

-continued

```
<400> SEQUENCE: 3
tatttaataa accatattgg                                             20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer derived from the Human
      Papillomavirus (HPV)

<400> SEQUENCE: 4
tatttaataa gccatattgg                                             20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer derived from the Human
      Papillomavirus (HPV)

<400> SEQUENCE: 5
gcacagggcc acaataatgg                                             20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer derived from the Human
      Papillomavirus (HPV)

<400> SEQUENCE: 6
gcmcaggghc ataayaatgg                                             20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer derived from the Human
      Papillomavirus (HPV)

<400> SEQUENCE: 7
gtatcaacaa cagtaacaaa                                             20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer derived from the Human
      Papillomavirus (HPV)

<400> SEQUENCE: 8
gtatctacca cagtaacaaa                                             20

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer derived from the Human
      Papillomavirus (HPV)

<400> SEQUENCE: 9
```
gtatchacha cagtaacaaa                                                     20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer for the Human
      Papillomavirus (HPV)

<400> SEQUENCE: 10
tatttaataa gccttattgg                                                     20

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer for the Human
      Papillomavirus (HPV)

<400> SEQUENCE: 11
tattcaataa accttattgg                                                     20

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer for the Human
      Papillomavirus (HPV)

<400> SEQUENCE: 12
tatttaataa accttactgg                                                     20

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer for the Human
      Papillomavirus (HPV)
<220> FEATURE:
<221> NAME/KEY: modified_base
<222> LOCATION: (11)..(11)
<223> OTHER INFORMATION: i
<220> FEATURE:
<221> NAME/KEY: modified_base
<222> LOCATION: (14)..(14)
<223> OTHER INFORMATION: i

<400> SEQUENCE: 13
tatttaataa nccntattgg                                                     20

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer for the Human
      Papillomavirus (HPV)
<220> FEATURE:
<221> NAME/KEY: modified_base
<222> LOCATION: (11)..(11)
<223> OTHER INFORMATION: i
<220> FEATURE:
<221> NAME/KEY: modified_base
<222> LOCATION: (14)..(14)
<223> OTHER INFORMATION: i

```
<400> SEQUENCE: 14
tatttaataa nccntactgg                                                     20

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer for the Human
      Papillomavirus (HPV)
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (9)..(9)
<223> OTHER INFORMATION: i

<400> SEQUENCE: 15
gcncagggnc acaataatgg                                                     20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer for the Human
      Papillomavirus (HPV)
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (9)..(9)
<223> OTHER INFORMATION: i

<400> SEQUENCE: 16
gcncagggnc ataacaatgg                                                     20

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer for the Human
      Papillomavirus (HPV)
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (9)..(9)
<223> OTHER INFORMATION: i

<400> SEQUENCE: 17
gcncagggnc ataataatgg                                                     20

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer for the Human
      Papillomavirus (HPV)
<220> FEATURE:
<221> NAME/KEY: modified_base
<222> LOCATION: (3)..(3)
```

```
<223> OTHER INFORMATION: i
<220> FEATURE:
<221> NAME/KEY: modified_base
<222> LOCATION: (9)..(9)
<223> OTHER INFORMATION: i

<400> SEQUENCE: 18
gcncaaggnc ataataatgg                                                    20

<210> SEQ ID NO 19
<211> LENGTH: 23
<212> TYPE: DNA
<213> ORGANISM: Artificial Sequence
<220> FEATURE:
<223> OTHER INFORMATION: Synthetic Primer for the Human
      Papillomavirus (HPV)
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (9)..(9)
<223> OTHER INFORMATION: i

<400> SEQUENCE: 19
gtngtatcna caacagtaac aaa                                                23

<210> SEQ ID NO 20
<211> LENGTH: 23
<212> TYPE: DNA
<213> ORGANISM: Artificial Sequence
<220> FEATURE:
<223> OTHER INFORMATION: Synthetic Primer for the Human
      Papillomavirus (HPV)
<220> FEATURE:
<221> NAME/KEY: modified_base
<222> LOCATION: (3)..(3)
<223> OTHER INFORMATION: i

<400> SEQUENCE: 20
gtngtatcta ccacagtaac aaa                                                23

<210> SEQ ID NO 21
<211> LENGTH: 23
<212> TYPE: DNA
<213> ORGANISM: Artificial Sequence
<220> FEATURE:
<223> OTHER INFORMATION: Synthetic Primer for the Human
      Papillomavirus (HPV)
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (9)..(9)
OTHER INFORMATION: i

<400> SEQUENCE: 21
gtngtatcna ctacagtaac aaa                                                23

<210> SEQ ID NO 22
<211> LENGTH: 23
<212> TYPE: DNA
<213> ORGANISM: Artificial Sequence
<220> FEATURE:
<223> OTHER INFORMATION: Synthetic Primer for the Human
      Papillomavirus (HPV)
<220> FEATURE:
<221> NAME/KEY: modified_base
```

```
<222> LOCATION: (3)..(3)
<223> OTHER INFORMATION: i
<220> FEATURE:
<221> NAME/KEY: modified_base
<222> LOCATION: (9)..(9)
<223> OTHER INFORMATION: i
<220> FEATURE:
<221> NAME/KEY: modified_base
<222> LOCATION: (18)..(18)
<223> OTHER INFORMATION: i

<400> SEQUENCE: 22
gtngtatcna cgacagtnac aaa                                              23

<210> SEQ ID NO 23
<211> LENGTH: 23
<212> TYPE: DNA
<213> ORGANISM: Artificial Sequence
<220> FEATURE:
<223> OTHER INFORMATION: Synthetic Primer for the Human
      Papillomavirus (HPV)
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (9)..(9)
<223> OTHER INFORMATION: i
<220> FEATURE:
<221> NAME/KEY: modified_base
<222> LOCATION: (18)..(18)
<223> OTHER INFORMATION: i
<220> FEATURE:
<221> NAME/KEY: modified_base
<222> LOCATION: (20)..(20)
OTHER INFORMATION: i

<400> SEQUENCE: 23
gtngtatcna caacagtnan aaa                                              23

<210> SEQ ID NO 24
<211> LENGTH: 19
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 24
ttggggtaat caactgtgg                                                   19

<210> SEQ ID NO 25
<211> LENGTH: 20
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 25
gttggggtaa tcaactgtgg                                                  20

<210> SEQ ID NO 26
<211> LENGTH: 19
<212> TYPE: DNA
<213> ORGANISM: Artificial Sequence
<220> FEATURE:
<223> OTHER INFORMATION: Type specific probe derived from the Human
      Papillomavirus (HPV)
```

```
<400> SEQUENCE: 26
ttggggtaat caactgttg                                                    19

<210> SEQ ID NO 27
<211> LENGTH: 20
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 27
gttggggtaa tcaactgttg                                                   20

<210> SEQ ID NO 28
<211> LENGTH: 19
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 28
ttggggtaat caactgttt                                                    19

<210> SEQ ID NO 29
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 29
tgctggggaa accactg                                                      17

<210> SEQ ID NO 30
<211> LENGTH: 20
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 30
tgctggggaa accacttagg                                                   20

<210> SEQ ID NO 31
<211> LENGTH: 18
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 31
ttgttgggga aaccactg                                                     18

<210> SEQ ID NO 32
<211> LENGTH: 21
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 32
```

```
ttgctgggga aaccacttag g                                          21
```

<210> SEQ ID NO 33
<211> LENGTH: 20
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 33

```
tgctggggaa accacttggg                                            20
```

<210> SEQ ID NO 34
<211> LENGTH: 19
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 34

```
ttggggtaac caactatgg                                             19
```

<210> SEQ ID NO 35
<211> LENGTH: 20
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 35

```
gttggggtaa ccaactatgg                                            20
```

<210> SEQ ID NO 36
<211> LENGTH: 19
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 36

```
ttggggtaac caactattg                                             19
```

<210> SEQ ID NO 37
<211> LENGTH: 20
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 37

```
gttggggtaa ccaactattg                                            20
```

<210> SEQ ID NO 38
<211> LENGTH: 19
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 38

```
ttggggtaac caactattt                                                     19
```

<210> SEQ ID NO 39
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 39

```
gtgtttgctg gcataat                                                       17
```

<210> SEQ ID NO 40
<211> LENGTH: 18
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 40

```
ggtgtttgct ggcataag                                                      18
```

<210> SEQ ID NO 41
<211> LENGTH: 18
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 41

```
gtgtttgctg gcataatc                                                      18
```

<210> SEQ ID NO 42
<211> LENGTH: 19
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 42

```
tggtgtttgc tggcataag                                                     19
```

<210> SEQ ID NO 43
<211> LENGTH: 18
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 43

```
ggtgtttgct ggcataat                                                      18
```

<210> SEQ ID NO 44
<211> LENGTH: 19
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 44

```
ttggggcaat cagttatgg                                                     19
```

<210> SEQ ID NO 45
<211> LENGTH: 20
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 45
gttggggcaa tcagttatgg                                          20

<210> SEQ ID NO 46
<211> LENGTH: 19
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 46
ttggggcaat cagttattg                                           19

<210> SEQ ID NO 47
<211> LENGTH: 20
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 47
gttggggcaa tcagttattg                                          20

<210> SEQ ID NO 48
<211> LENGTH: 20
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 48
gttggggcaa tcagttattt                                          20

<210> SEQ ID NO 49
<211> LENGTH: 16
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 49
gggcaatcag ttattg                                              16

<210> SEQ ID NO 50
<211> LENGTH: 15
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 50
aataactgat tgccc                                               15

```
<210> SEQ ID NO 51
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 51
ggcaatcagt tatttcc                                                    17

<210> SEQ ID NO 52
<211> LENGTH: 15
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 52
aaataactga ttgcc                                                      15

<210> SEQ ID NO 53
<211> LENGTH: 16
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 53
gcaatcagtt atttgg                                                     16

<210> SEQ ID NO 54
<211> LENGTH: 15
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 54
caaataactg attgc                                                      15

<210> SEQ ID NO 55
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 55
ggcaatcagt tatttgg                                                    17

<210> SEQ ID NO 56
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 56
gcaatcagtt atttgtg                                                    17
```

```
<210> SEQ ID NO 57
<211> LENGTH: 19
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 57
ttggggcaat caggtatgg                                                   19

<210> SEQ ID NO 58
<211> LENGTH: 20
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 58
gttggggcaa tcaggtatgg                                                  20

<210> SEQ ID NO 59
<211> LENGTH: 19
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 59
ttggggcaat caggtattg                                                   19

<210> SEQ ID NO 60
<211> LENGTH: 20
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 60
gttggggcaa tcaggtattg                                                  20

<210> SEQ ID NO 61
<211> LENGTH: 20
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 61
gttggggcaa tcaggtattt                                                  20

<210> SEQ ID NO 62
<211> LENGTH: 16
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 62
gggcaatcag gtattg                                                      16

<210> SEQ ID NO 63
```

<210> SEQ ID NO 63
<211> LENGTH: 15
<212> TYPE: DNA
<213> ORGANISM: Artificial Sequence
<220> FEATURE:
<223> OTHER INFORMATION: Type specific probe derived from the Human Papillomavirus (HPV)

<400> SEQUENCE: 63
aatacctgat tgccc                                          15

<210> SEQ ID NO 64
<211> LENGTH: 17
<212> TYPE: DNA
<213> ORGANISM: Artificial Sequence
<220> FEATURE:
<223> OTHER INFORMATION: Type specific probe derived from the Human Papillomavirus (HPV)

<400> SEQUENCE: 64
ggcaatcagg tatttcc                                        17

<210> SEQ ID NO 65
<211> LENGTH: 15
<212> TYPE: DNA
<213> ORGANISM: Artificial Sequence
<220> FEATURE:
<223> OTHER INFORMATION: Type specific probe derived from the Human Papillomavirus (HPV)

<400> SEQUENCE: 65
aaatacctga ttgcc                                          15

<210> SEQ ID NO 66
<211> LENGTH: 16
<212> TYPE: DNA
<213> ORGANISM: Artificial Sequence
<220> FEATURE:
<223> OTHER INFORMATION: Type specific probe derived from the Human Papillomavirus (HPV)

<400> SEQUENCE: 66
gcaatcaggt atttgg                                         16

<210> SEQ ID NO 67
<211> LENGTH: 15
<212> TYPE: DNA
<213> ORGANISM: Artificial Sequence
<220> FEATURE:
<223> OTHER INFORMATION: Type specific probe derived from the Human Papillomavirus (HPV)

<400> SEQUENCE: 67
caaatacctg attgc                                          15

<210> SEQ ID NO 68
<211> LENGTH: 17
<212> TYPE: DNA
<213> ORGANISM: Artificial Sequence
<220> FEATURE:
<223> OTHER INFORMATION: Type specific probe derived from the Human Papillomavirus (HPV)

<400> SEQUENCE: 68
catatgtttt ggcaatc                                        17

<210> SEQ ID NO 69
<211> LENGTH: 17

```
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 69
gtatttgttg gcataat                                                    17

<210> SEQ ID NO 70
<211> LENGTH: 18
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 70
ggtatttgtt ggcataag                                                   18

<210> SEQ ID NO 71
<211> LENGTH: 18
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 71
gtatttgttg gcataatc                                                   18

<210> SEQ ID NO 72
<211> LENGTH: 19
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 72
tggtatttgt tggcataag                                                  19

<210> SEQ ID NO 73
<211> LENGTH: 18
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 73
ggtatttgtt ggcataat                                                   18

<210> SEQ ID NO 74
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 74
tggcataatc agttggg                                                    17

<210> SEQ ID NO 75
<211> LENGTH: 16
<212> TYPE: DNA
```

```
<213> ORGANISM: Artificial Sequence
<220> FEATURE:
<223> OTHER INFORMATION: Type specific probe derived from the Human
      Papillomavirus (HPV)

<400> SEQUENCE: 75
ggcataatca gttgtg                                                          16

<210> SEQ ID NO 76
<211> LENGTH: 16
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 76
gcataatcag ttgttt                                                          16

<210> SEQ ID NO 77
<211> LENGTH: 16
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 77
gcaatcagtt gtttgc                                                          16

<210> SEQ ID NO 78
<211> LENGTH: 16
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 78
caatcagttg tttgtc                                                          16

<210> SEQ ID NO 79
<211> LENGTH: 15
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 79
atggcatatg ttggg                                                           15

<210> SEQ ID NO 80
<211> LENGTH: 16
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 80
tggcatatgt tggggg                                                          16

<210> SEQ ID NO 81
<211> LENGTH: 15
<212> TYPE: DNA
<213> ORGANISM: Artificial Sequence
```

```
<220> FEATURE:
<223> OTHER INFORMATION: Type specific probe derived from the Human
      Papillomavirus (HPV)

<400> SEQUENCE: 81
ggcatatgtt ggggc                                                          15

<210> SEQ ID NO 82
<211> LENGTH: 15
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 82
gcatatgttg gggca                                                          15

<210> SEQ ID NO 83
<211> LENGTH: 16
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 83
ggggtaatca attatc                                                         16

<210> SEQ ID NO 84
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 84
ggggtaatca attattc                                                        17

<210> SEQ ID NO 85
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 85
ggggtaatca attattt                                                        17

<210> SEQ ID NO 86
<211> LENGTH: 18
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 86
tggggtaatc aattattt                                                       18

<210> SEQ ID NO 87
<211> LENGTH: 19
<212> TYPE: DNA
<213> ORGANISM: Artificial Sequence
<220> FEATURE:
```

```
<223> OTHER INFORMATION: Type specific probe derived from the Human
      Papillomavirus (HPV)

<400> SEQUENCE: 87
ggggtaatca attatttgg                                                    19

<210> SEQ ID NO 88
<211> LENGTH: 16
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 88
catttgctgg ggcaag                                                       16

<210> SEQ ID NO 89
<211> LENGTH: 15
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 89
atttgctggg gcaat                                                        15

<210> SEQ ID NO 90
<211> LENGTH: 15
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 90
tttgctgggg caatc                                                        15

<210> SEQ ID NO 91
<211> LENGTH: 15
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 91
ttgctggggc aatca                                                        15

<210> SEQ ID NO 92
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 92
gttggagtaa ccaattg                                                      17

<210> SEQ ID NO 93
<211> LENGTH: 17
<212> TYPE: DNA
<213> ORGANISM: Artificial Sequence
<220> FEATURE:
<223> OTHER INFORMATION: Type specific probe derived from the Human
```

Papillomavirus (HPV)

<400> SEQUENCE: 93
gtatatgttg gcataat                                                    17

<210> SEQ ID NO 94
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 94
gcatttgctg gaacaat                                                    17

<210> SEQ ID NO 95
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 95
ggggcaatca ggtgttt                                                    17

<210> SEQ ID NO 96
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 96
ggtatatgtt ggcacaa                                                    17

<210> SEQ ID NO 97
<211> LENGTH: 15
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 97
gcatatgctg gggta                                                      15

<210> SEQ ID NO 98
<211> LENGTH: 23
<212> TYPE: DNA
<213> ORGANISM: Artificial Sequence
<220> FEATURE:
<223> OTHER INFORMATION: Type specific probe derived from the Human
      Papillomavirus (HPV)
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (9)..(9)
<223> OTHER INFORMATION: i

<400> SEQUENCE: 98
gtngtatcna caactgtaac aaa                                             23

<210> SEQ ID NO 99
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 99
catttgttgg cataacc                                                   17

<210> SEQ ID NO 100
<211> LENGTH: 15
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 100
tggggcaatc acttg                                                     15

<210> SEQ ID NO 101
<211> LENGTH: 15
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 101
gcatttgctg gcata                                                     15

<210> SEQ ID NO 102
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 102
tggggaaatc agctatt                                                   17

<210> SEQ ID NO 103
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 103
ggcatttgtt ttgggaa                                                   17

<210> SEQ ID NO 104
<211> LENGTH: 18
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 104
ttggggaaat cagttatt                                                  18

```
<210> SEQ ID NO 105
<211> LENGTH: 16
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 105
gcatctgttg gaacaa                                                  16

<210> SEQ ID NO 106
<211> LENGTH: 15
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 106
gttgggggaa tcagt                                                   15

<210> SEQ ID NO 107
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 107
gttggggcaa ccaattg                                                 17

<210> SEQ ID NO 108
<211> LENGTH: 18
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 108
tggtttaatg aattgttt                                                18

<210> SEQ ID NO 109
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 109
ggtttaatga actgttt                                                 17

<210> SEQ ID NO 110
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 110
aatggaattt gttggca                                                 17

<210> SEQ ID NO 111
```

```
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 111
gtatatgctg gggtaat                                                        17

<210> SEQ ID NO 112
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 112
atttgttggg gtaatca                                                        17

<210> SEQ ID NO 113
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 113
tgctggaata atcagct                                                        17

<210> SEQ ID NO 114
<211> LENGTH: 18
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 114
tggtttaatg agttattt                                                       18

<210> SEQ ID NO 115
<211> LENGTH: 17
<212> TYPE: DNA
<213> ORGANISM: Artificial Sequence
<220> FEATURE:
<223> OTHER INFORMATION: Type specific probe derived from the Human
      Papillomavirus (HPV)

<400> SEQUENCE: 115
atatgctggt ttaatca                                                        17

<210> SEQ ID NO 116
<211> LENGTH: 18
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (12)..(12)
<223> OTHER INFORMATION: i

<400> SEQUENCE: 116
aataatggca tntgttgg                                                       18
```

<210> SEQ ID NO 117
<211> LENGTH: 18
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (12)..(12)
<223> OTHER INFORMATION: i

<400> SEQUENCE: 117
aataatggta tntgttgg                                                    18

<210> SEQ ID NO 118
<211> LENGTH: 18
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (12)..(12)
<223> OTHER INFORMATION: i

<400> SEQUENCE: 118
aacaatggta tntgttgg                                                    18

<210> SEQ ID NO 119
<211> LENGTH: 18
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (12)..(12)
<223> OTHER INFORMATION: i

<400> SEQUENCE: 119
aacaatggta tntgctgg                                                    18

<210> SEQ ID NO 120
<211> LENGTH: 18
<212> TYPE: DNA
<213> ORGANISM: Artificial Sequence
<220> FEATURE:
<223> OTHER INFORMATION: General Probe for Human Papillomavirus
      (HPV) detectio

<400> SEQUENCE: 120
aacaatggtg tttgctgg                                                    18

<210> SEQ ID NO 121
<211> LENGTH: 18
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (12)..(12)
<223> OTHER INFORMATION: i

<400> SEQUENCE: 121

```
aataatggca tntgctgg                                              18

<210> SEQ ID NO 122
<211> LENGTH: 18
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (12)..(12)
<223> OTHER INFORMATION: i

<400> SEQUENCE: 122
aacaatggca tntgctgg                                              18

<210> SEQ ID NO 123
<211> LENGTH: 21
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (15)..(15)
OTHER INFORMATION: i

<400> SEQUENCE: 123
canaataatg gtatntgttg g                                          21

<210> SEQ ID NO 124
<211> LENGTH: 20
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (2)..(2)
<223> OTHER INFORMATION: i
<220> FEATURE:
<221> NAME/KEY: modified_base
<222> LOCATION: (14)..(14)
<223> OTHER INFORMATION: i

<400> SEQUENCE: 124
anaataatgg tatntgttgg                                            20

<210> SEQ ID NO 125
<211> LENGTH: 21
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (3)..(3)
<223> OTHER INFORMATION: i

<400> SEQUENCE: 125
canaataatg gtatttgttg g                                          21
```

<210> SEQ ID NO 126
<211> LENGTH: 20
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (2)..(2)
<223> OTHER INFORMATION: i

<400> SEQUENCE: 126
anaataatgg tatttgttgg                                                    20

<210> SEQ ID NO 127
<211> LENGTH: 21
<212> TYPE: DNA
<213> ORGANISM: Artificial Sequence
<220> FEATURE:
<223> OTHER INFORMATION: General probe derived from the Human
      Papillomavirus (HPV)

<400> SEQUENCE: 127
cacaataatg gtatttgttg g                                                  21

<210> SEQ ID NO 128
<211> LENGTH: 20
<212> TYPE: DNA
<213> ORGANISM: Artificial Sequence
<220> FEATURE:
<223> OTHER INFORMATION: General probe derived from the Human
      Papillomavirus (HPV)

<400> SEQUENCE: 128
acaataatgg tatttgttgg                                                    20

<210> SEQ ID NO 129
<211> LENGTH: 21
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (3)..(3)
OTHER INFORMATION: i
<220> FEATURE:
<221> NAME/KEY: modified_base
<222> LOCATION: (15)..(15)
<223> OTHER INFORMATION: i

<400> SEQUENCE: 129
canaacaatg gtatntgttg g                                                  21

<210> SEQ ID NO 130
<211> LENGTH: 20
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (2)..(2)
<223> OTHER INFORMATION: i
<220> FEATURE:
<221> NAME/KEY: modified_base
<222> LOCATION: (14)..(14)

<223> OTHER INFORMATION: i

<400> SEQUENCE: 130
anaacaatgg tatntgttgg                                               20

<210> SEQ ID NO 131
<211> LENGTH: 21
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (3)..(3)
<223> OTHER INFORMATION: i

<400> SEQUENCE: 131
canaacaatg gtatttgttg g                                             21

<210> SEQ ID NO 132
<211> LENGTH: 20
<212> TYPE: DNA
<213> ORGANISM: Artificial Sequence
<220> FEATURE:
<223> OTHER INFORMATION: General probe derived from the Human
      Papillomavirus (HPV)
<220> FEATURE:
<221> NAME/KEY: modified_base
<222> LOCATION: (2)..(2)
<223> OTHER INFORMATION: i

<400> SEQUENCE: 132
anaacaatgg tatttgttgg                                               20

<210> SEQ ID NO 133
<211> LENGTH: 21
<212> TYPE: DNA
<213> ORGANISM: Artificial Sequence
<220> FEATURE:
<223> OTHER INFORMATION: General probe derived from the Human
      Papillomavirus (HPV)

<400> SEQUENCE: 133
cataacaatg gtatttgttg g                                             21

<210> SEQ ID NO 134
<211> LENGTH: 20
<212> TYPE: DNA
<213> ORGANISM: Artificial Sequence
<220> FEATURE:
<223> OTHER INFORMATION: General probe derived from the Human
      Papillomavirus (HPV)

<400> SEQUENCE: 134
ataacaatgg tatttgttgg                                               20

<210> SEQ ID NO 135
<211> LENGTH: 20
<212> TYPE: DNA
<213> ORGANISM: Human Papillomavirus

<400> SEQUENCE: 135
catatgctgg aataatcaac                                               20

<210> SEQ ID NO 136
<211> LENGTH: 20

```
<212> TYPE: DNA
<213> ORGANISM: Human Papillomavirus

<400> SEQUENCE: 136
catatgctgg aataatcttc                                                    20

<210> SEQ ID NO 137
<211> LENGTH: 22
<212> TYPE: DNA
<213> ORGANISM: Human Papillomavirus

<400> SEQUENCE: 137
tatctgctgg ggtaatcagc tt                                                 22

<210> SEQ ID NO 138
<211> LENGTH: 21
<212> TYPE: DNA
<213> ORGANISM: Human Papillomavirus

<400> SEQUENCE: 138
atctgctggc ayaatcaatt a                                                  21

<210> SEQ ID NO 139
<211> LENGTH: 20
<212> TYPE: DNA
<213> ORGANISM: Human Papillomavirus

<400> SEQUENCE: 139
tctgctggca taatcaatta                                                    20

<210> SEQ ID NO 140
<211> LENGTH: 22
<212> TYPE: DNA
<213> ORGANISM: Human Papillomavirus

<400> SEQUENCE: 140
tatatgttgg cataatcaat ta                                                 22

<210> SEQ ID NO 141
<211> LENGTH: 22
<212> TYPE: DNA
<213> ORGANISM: Human Papillomavirus

<400> SEQUENCE: 141
aatttgttgg cataatcaat tg                                                 22

<210> SEQ ID NO 142
<211> LENGTH: 20
<212> TYPE: DNA
<213> ORGANISM: Human Papillomavirus

<400> SEQUENCE: 142
tttgttgggg taatcaattg                                                    20

<210> SEQ ID NO 143
<211> LENGTH: 20
<212> TYPE: DNA
<213> ORGANISM: Human Papillomavirus

<400> SEQUENCE: 143
tttgctggtt taatcaattg                                                    20

<210> SEQ ID NO 144
```

-continued

```
<210> SEQ ID NO 144
<211> LENGTH: 20
<212> TYPE: DNA
<213> ORGANISM: Human Papillomavirus

<400> SEQUENCE: 144
tatgttggtt taatgagctg                                                    20

<210> SEQ ID NO 145
<211> LENGTH: 20
<212> TYPE: DNA
<213> ORGANISM: Human Papillomavirus

<400> SEQUENCE: 145
tttgttggtt taatgagttg                                                    20

<210> SEQ ID NO 146
<211> LENGTH: 20
<212> TYPE: DNA
<213> ORGANISM: Human Papillomavirus

<400> SEQUENCE: 146
tttgttggtt taatgagtta                                                    20

<210> SEQ ID NO 147
<211> LENGTH: 21
<212> TYPE: DNA
<213> ORGANISM: Human Papillomavirus

<400> SEQUENCE: 147
atttgttggt taatgagat g                                                   21

<210> SEQ ID NO 148
<211> LENGTH: 20
<212> TYPE: DNA
<213> ORGANISM: Human Papillomavirus

<400> SEQUENCE: 148
tttgttggtt taatgaaatg                                                    20

<210> SEQ ID NO 149
<211> LENGTH: 20
<212> TYPE: DNA
<213> ORGANISM: Human Papillomavirus

<400> SEQUENCE: 149
tatgttggtt taatgagctg                                                    20

<210> SEQ ID NO 150
<211> LENGTH: 20
<212> TYPE: DNA
<213> ORGANISM: Human Papillomavirus

<400> SEQUENCE: 150
tytgttggtt taatgacctg                                                    20

<210> SEQ ID NO 151
<211> LENGTH: 22
<212> TYPE: DNA
<213> ORGANISM: Human Papillomavirus

<400> SEQUENCE: 151
tatttgttgg tttaatgacc tg                                                 22
```

```
<210> SEQ ID NO 152
<211> LENGTH: 20
<212> TYPE: DNA
<213> ORGANISM: Human Papillomavirus

<400> SEQUENCE: 152
tttgttggtt taatgaaatg                                              20

<210> SEQ ID NO 153
<211> LENGTH: 21
<212> TYPE: DNA
<213> ORGANISM: Human Papillomavirus

<400> SEQUENCE: 153
atctgttttg gyaaccaggt g                                            21

<210> SEQ ID NO 154
<211> LENGTH: 23
<212> TYPE: DNA
<213> ORGANISM: Artificial Sequence
<220> FEATURE:
<223> OTHER INFORMATION: Synthetic Primer derived from the Human
      Papillomavirus (HPV)
<220> FEATURE:
<221> NAME/KEY: modified_base
<222> LOCATION: (3)..(3)
<223> OTHER INFORMATION: i

<400> SEQUENCE: 154
gtngtatcca caacagttac aaa                                          23

<210> SEQ ID NO 155
<211> LENGTH: 23
<212> TYPE: DNA
<213> ORGANISM: Artificial Sequence
<220> FEATURE:
<223> OTHER INFORMATION: Synthetic Primer derived from the Human
      Papillomavirus (HPV)
<220> FEATURE:
<221> NAME/KEY: modified_base
<222> LOCATION: (15)..(15)
<223> OTHER INFORMATION: i

<400> SEQUENCE: 155
gtggtatcca caacngtgac aaa                                          23

<210> SEQ ID NO 156
<211> LENGTH: 23
<212> TYPE: DNA
<213> ORGANISM: Artificial Sequence
<220> FEATURE:
<223> OTHER INFORMATION: Synthetic Primer derived from the Human
      Papillomavirus (HPV)
<220> FEATURE:
<221> NAME/KEY: modified_base
<222> LOCATION: (6)..(6)
<223> OTHER INFORMATION: i

<400> SEQUENCE: 156
gtagtntcca caacagtaag aaa                                          23

<210> SEQ ID NO 157
<211> LENGTH: 23
<212> TYPE: DNA
<213> ORGANISM: Artificial Sequence
<220> FEATURE:
<223> OTHER INFORMATION: Synthetic Primer derived from the Human
      Papillomavirus (HPV)
```

```
<400> SEQUENCE: 157
gtagtatcaa ccacagttaa aaa                                              23

<210> SEQ ID NO 158
<211> LENGTH: 23
<212> TYPE: DNA
<213> ORGANISM: Artificial Sequence
<220> FEATURE:
<223> OTHER INFORMATION: Synthetic Primer derived from the Human
      Papillomavirus (HPV)
<220> FEATURE:
<221> NAME/KEY: modified_base
<222> LOCATION: (3)..(3)
OTHER INFORMATION: i
<220> FEATURE:
<221> NAME/KEY: modified_base
<222> LOCATION: (15)..(15)
<223> OTHER INFORMATION: i

<400> SEQUENCE: 158
gtngtatcta caacngttaa aaa                                              23

<210> SEQ ID NO 159
<211> LENGTH: 23
<212> TYPE: DNA
<213> ORGANISM: Artificial Sequence
<220> FEATURE:
<223> OTHER INFORMATION: Synthetic Primer derived from the Human
      Papillomavirus (HPV)

<400> SEQUENCE: 159
gtagtatcta cacaagtaac aaa                                              23

<210> SEQ ID NO 160
<211> LENGTH: 23
<212> TYPE: DNA
<213> ORGANISM: Artificial Sequence
<220> FEATURE:
<223> OTHER INFORMATION: Synthetic Primer derived from the Human
      Papillomavirus (HPV)

<400> SEQUENCE: 160
gtagtatcaa cacaggtaat aaa                                              23

<210> SEQ ID NO 161
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 161
ggtatctgct ggcataag                                                    18

<210> SEQ ID NO 162
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 162
tggtatctgc tggcata                                                     17

<210> SEQ ID NO 163
```

```
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 163
tatttgttgg ggcaatc                                                    17

<210> SEQ ID NO 164
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 164
atttgttggg gcaatc                                                     16

<210> SEQ ID NO 165
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 165
tatttgttgg ggcaat                                                     16

<210> SEQ ID NO 166
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 166
ggcatttgct ggcata                                                     16

<210> SEQ ID NO 167
<211> LENGTH: 19
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 167
gttggagtaa ccaattggg                                                  19

<210> SEQ ID NO 168
<211> LENGTH: 19
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 168
tgttggagta accaattcc                                                  19

<210> SEQ ID NO 169
<211> LENGTH: 18
```

```
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 169
ttgttggagt aaccaatg                                              18

<210> SEQ ID NO 170
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 170
ggtatatgtt ggcataat                                              18

<210> SEQ ID NO 171
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 171
ggggaaatca gctattg                                               17

<210> SEQ ID NO 172
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 172
gggaaatcag ctattt                                                16

<210> SEQ ID NO 173
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 173
ggcatttgtt ttgggaag                                              18

<210> SEQ ID NO 174
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 174
gcatttgttt tgggaat                                               17

<210> SEQ ID NO 175
<211> LENGTH: 17
<212> TYPE: DNA
```

<213> ORGANISM: Artificial Sequence
<220> FEATURE:
<223> OTHER INFORMATION: Synthetic Probe derived from the Human
      Papillomavirus (HPV)

<400> SEQUENCE: 175
catttgtttt gggaatc                                                17

<210> SEQ ID NO 176
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 176
ggggaaatca gttattg                                                17

<210> SEQ ID NO 177
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 177
ggggaaatca gttattt                                                17

<210> SEQ ID NO 178
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 178
gggaaatcag ttattt                                                 16

<210> SEQ ID NO 179
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 179
tggggaaatc agttatg                                                17

<210> SEQ ID NO 180
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 180
catttgctgg aacaatc                                                17

<210> SEQ ID NO 181
<211> LENGTH: 17
<212> TYPE: DNA
<213> ORGANISM: Artificial Sequence

```
<220> FEATURE:
<223> OTHER INFORMATION: Synthetic Probe derived from the Human
      Papillomavirus (HPV)

<400> SEQUENCE: 181
ggcatctgtt ggaacaa                                                  17

<210> SEQ ID NO 182
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 182
ggcaatcagg tgtttc                                                   16

<210> SEQ ID NO 183
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 183
gggcaatcag gtgtttc                                                  17

<210> SEQ ID NO 184
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 184
aaacacctga ttgccc                                                   16

<210> SEQ ID NO 185
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 185
ggcaatcagg tgttttg                                                  17

<210> SEQ ID NO 186
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 186
gggggaatca gttattg                                                  17

<210> SEQ ID NO 187
<211> LENGTH: 16
<212> TYPE: DNA
<213> ORGANISM: Artificial Sequence
<220> FEATURE:
```

```
<223> OTHER INFORMATION: Synthetic Probe derived from the Human
      Papillomavirus (HPV)

<400> SEQUENCE: 187
gggggaatca gttatg                                                   16

<210> SEQ ID NO 188
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 188
tgggggaatc agttatg                                                  17

<210> SEQ ID NO 189
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 189
tgggggaatc agttag                                                   16

<210> SEQ ID NO 190
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 190
catttgctgg ggtaat                                                   16

<210> SEQ ID NO 191
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 191
tggtatatgt tggcacaa                                                 18

<210> SEQ ID NO 192
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 192
ggtatatgtt ggcacaat                                                 18

<210> SEQ ID NO 193
<211> LENGTH: 18
<212> TYPE: DNA
<213> ORGANISM: Artificial Sequence
<220> FEATURE:
<223> OTHER INFORMATION: Synthetic Probe derived from the Human
```

Papillomavirus (HPV)

<400> SEQUENCE: 193
gtatatgttg gcacaatc                                                    18

<210> SEQ ID NO 194
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 194
tatatgttgg cacaatc                                                     17

<210> SEQ ID NO 195
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 195
ggcatatgct ggggta                                                      16

<210> SEQ ID NO 196
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 196
ggtatatgct ggggtaat                                                    18

<210> SEQ ID NO 197
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 197
ggtatatgct ggggta                                                      16

<210> SEQ ID NO 198
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 198
tggtatatgc tggggt                                                      16

<210> SEQ ID NO 199
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

```
<400> SEQUENCE: 199
atggtatatg ctggggg                                                17

<210> SEQ ID NO 200
<211> LENGTH: 15
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 200
ggtatatgct ggggt                                                  15

<210> SEQ ID NO 201
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 201
tggtatatgc tggggg                                                 16

<210> SEQ ID NO 202
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 202
aatggtatat gctggg                                                 16

<210> SEQ ID NO 203
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 203
tggtatttgt tggcata                                                17

<210> SEQ ID NO 204
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 204
atggtatttg ttggcata                                               18

<210> SEQ ID NO 205
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)
```

<400> SEQUENCE: 205
atggtatttg ttggcat                                                    17

<210> SEQ ID NO 206
<211> LENGTH: 19
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 206
ttggcataat caattattt                                                  19

<210> SEQ ID NO 207
<211> LENGTH: 21
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 207
ttggcataat caattatttc g                                               21

<210> SEQ ID NO 208
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 208
gcatttgttg gcataacc                                                   18

<210> SEQ ID NO 209
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 209
gcatttgttg gcataac                                                    17

<210> SEQ ID NO 210
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 210
catttgttgg cataac                                                     16

<210> SEQ ID NO 211
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 211
tatttgttgg ggtaat                                                   16

<210> SEQ ID NO 212
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 212
atttgttggg gtaatc                                                   16

<210> SEQ ID NO 213
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 213
tttgttgggg taatca                                                   16

<210> SEQ ID NO 214
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 214
gtatttgttg gggtaat                                                  17

<210> SEQ ID NO 215
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 215
tatttgttgg ggtaatc                                                  17

<210> SEQ ID NO 216
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 216
ttgctggaat aatcagct                                                 18

<210> SEQ ID NO 217
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 217

-continued

```
tgctggaata atcagc                                                    16
```

<210> SEQ ID NO 218
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 218

```
tgctggaata atcagctg                                                  18
```

<210> SEQ ID NO 219
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 219

```
tgctggaata atcagcg                                                   17
```

<210> SEQ ID NO 220
<211> LENGTH: 22
<212> TYPE: DNA
<213> ORGANISM: Artificial Sequence
<220> FEATURE:
<223> OTHER INFORMATION: Synthetic Probe derived from the Human
      Papillomavirus (HPV)
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (15)..(15)
<223> OTHER INFORMATION: i

<400> SEQUENCE: 220

```
canaataatg gcatntgttg gc                                             22
```

<210> SEQ ID NO 221
<211> LENGTH: 22
<212> TYPE: DNA
<213> ORGANISM: Artificial Sequence
<220> FEATURE:
<223> OTHER INFORMATION: Synthetic Probe derived from the Human
      Papillomavirus (HPV)
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (15)..(15)
<223> OTHER INFORMATION: i

<400> SEQUENCE: 221

```
canaacaatg gcatntgttg gc                                             22
```

<210> SEQ ID NO 222
<211> LENGTH: 23
<212> TYPE: DNA
<213> ORGANISM: Artificial Sequence
<220> FEATURE:
<223> OTHER INFORMATION: Synthetic Probe derived from the Human
      Papillomavirus (HPV)

```
<400> SEQUENCE: 222
cacaataatg gcatttgttg ggg                                      23

<210> SEQ ID NO 223
<211> LENGTH: 22
<212> TYPE: DNA
<213> ORGANISM: Artificial Sequence
<220> FEATURE:
<223> OTHER INFORMATION: Synthetic Probe derived from the Human
      Papillomavirus (HPV)
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (15)..(15)
<223> OTHER INFORMATION: i

<400> SEQUENCE: 223
canaataatg gtatntgttg gg                                       22

<210> SEQ ID NO 224
<211> LENGTH: 22
<212> TYPE: DNA
<213> ORGANISM: Artificial Sequence
<220> FEATURE:
<223> OTHER INFORMATION: Synthetic Probe derived from the Human
      Papillomavirus (HPV)
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (15)..(15)
<223> OTHER INFORMATION: i

<400> SEQUENCE: 224
canaacaatg gtatntgttg gc                                       22

<210> SEQ ID NO 225
<211> LENGTH: 30
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 225
aatggcattt gttggggtaa ccaactattt                               30

<210> SEQ ID NO 226
<211> LENGTH: 21
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 226
ttgttggggt aaccaactat g                                        21

<210> SEQ ID NO 227
<211> LENGTH: 24
<212> TYPE: DNA
<213> ORGANISM: Artificial Sequence
<220> FEATURE:
<223> OTHER INFORMATION: Synthetic Probe derived from the Human
```

Papillomavirus (HPV)

<400> SEQUENCE: 227
atttgttggg gtaaccaact attg                                   24

<210> SEQ ID NO 228
<211> LENGTH: 23
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 228
gcatttgttg gggtaaccaa cta                                    23

<210> SEQ ID NO 229
<211> LENGTH: 25
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 229
tggcatttgt tggggtaacc aacta                                  25

<210> SEQ ID NO 230
<211> LENGTH: 30
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 230
aatggtattt gttggggcaa tcagttattt                             30

<210> SEQ ID NO 231
<211> LENGTH: 30
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 231
aatggtattt gttggcataa tcagttgttt                             30

<210> SEQ ID NO 232
<211> LENGTH: 30
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 232
aatggtattt gttggtttaa tgaattgttt                             30

<210> SEQ ID NO 233
<211> LENGTH: 30
<212> TYPE: DNA
<213> ORGANISM: Artificial Sequence
<220> FEATURE:
<223> OTHER INFORMATION: Synthetic Probe derived from the Human
      Papillomavirus (HPV)

```
<400> SEQUENCE: 233
aatggcattt gctggaacaa tcagcttttt                                30

<210> SEQ ID NO 234
<211> LENGTH: 30
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 234
aatggtatat gttggggcaa tcacttgttt                                30

<210> SEQ ID NO 235
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 235
aatggcattt gttggggc                                             18

<210> SEQ ID NO 236
<211> LENGTH: 22
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 236
aatggcatat gctggaataa tc                                        22

<210> SEQ ID NO 237
<211> LENGTH: 22
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 237
aatggtatat gttggggcaa tc                                        22

<210> SEQ ID NO 238
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 238 aatggtatttt gttggggc                                            18

<210> SEQ ID NO 239
<211> LENGTH: 22
<212> TYPE: DNA
<213> ORGANISM: Artificial Sequence
<220> FEATURE:
<223> OTHER INFORMATION: Synthetic Probe derived from the Human
      Papillomavirus (HPV)
```

<400> SEQUENCE: 239
aatggaattt gttggcataa tc                                      22

<210> SEQ ID NO 240
<211> LENGTH: 18
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 240
ggtatctgct ggcataat                                           18

<210> SEQ ID NO 241
<211> LENGTH: 22
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 241
aatggcattt gttggtttaa tg                                      22

<210> SEQ ID NO 242
<211> LENGTH: 22
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 242
aatggtattt gttggtttaa tg                                      22

<210> SEQ ID NO 243
<211> LENGTH: 22
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 243
aatggcatct gttggtttaa tg                                      22

<210> SEQ ID NO 244
<211> LENGTH: 20
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 244
tgttggttta atgagctgtg                                         20

<210> SEQ ID NO 245
<211> LENGTH: 21
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 245

```
tgctggttta atcaattgtt g                                              21

<210> SEQ ID NO 246
<211> LENGTH: 16
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 246
cagggacaca acaatg                                                    16

<210> SEQ ID NO 247
<211> LENGTH: 17
<212> TYPE: DNA
<213> ORGANISM: Artificial Sequence
<220> FEATURE:
<223> OTHER INFORMATION: Synthetic Probe derived from the Human
      Papillomavirus (HPV)

<400> SEQUENCE: 247
cagggtcata acaatgg                                                   17

<210> SEQ ID NO 248
<211> LENGTH: 65
<212> TYPE: DNA
<213> ORGANISM: Human Papillomavirus

<400> SEQUENCE: 248
gcccagggac ataacaatgg tatttgttgg ggtaatcaac tgtttgttac tgtggtagat    60
accac                                                                65

<210> SEQ ID NO 249
<211> LENGTH: 94
<212> TYPE: DNA
<213> ORGANISM: Human Papillomavirus

<400> SEQUENCE: 249
tatttaataa accatattgg cttcaaaagg ctcagggaca taacaatggt atttgctggg    60
gaaaccactt gtttgttact gtggtagata ccac                                94

<210> SEQ ID NO 250
<211> LENGTH: 65
<212> TYPE: DNA
<213> ORGANISM: Human Papillomavirus

<400> SEQUENCE: 250
gctcagggac ataacaatgg tatttgctgg ggaaaccact tgtttgttac tgtggtagat    60
accac                                                                65

<210> SEQ ID NO 251
<211> LENGTH: 65
<212> TYPE: DNA
<213> ORGANISM: Human Papillomavirus

<400> SEQUENCE: 251
gcccagggac acaataatgg tatatgttgg ggcaatcact tgtttgttac tgtagttgat    60
actac                                                                65

<210> SEQ ID NO 252
```

-continued

<211> LENGTH: 94
<212> TYPE: DNA
<213> ORGANISM: Human Papillomavirus

<400> SEQUENCE: 252
tgtttaataa accatattgg ttacataagg cacagggtca taacaatggt gtttgctggc    60
ataatcaatt atttgttact gtggtagata ccac    94

<210> SEQ ID NO 253
<211> LENGTH: 65
<212> TYPE: DNA
<213> ORGANISM: Human Papillomavirus

<400> SEQUENCE: 253
gcacagggtc ataacaatgg tgtttgctgg cataatcaat tatttgttac tgtggtagat    60
accac    65

<210> SEQ ID NO 254
<211> LENGTH: 65
<212> TYPE: DNA
<213> ORGANISM: Human Papillomavirus

<400> SEQUENCE: 254
gcacagggtc ataataatgg tatctgttgg ggcaatcaat tgtttgttac ctgtgttgat    60
accac    65

<210> SEQ ID NO 255
<211> LENGTH: 65
<212> TYPE: DNA
<213> ORGANISM: Human Papillomavirus

<400> SEQUENCE: 255
gcacagggac acaataatgg catttgttgg ggcaaccagg tatttgttac tgttgtggac    60
accac    65

<210> SEQ ID NO 256
<211> LENGTH: 94
<212> TYPE: DNA
<213> ORGANISM: Human Papillomavirus

<400> SEQUENCE: 256
tttttaataa accatattgg atgcaacgtg ctcagggaca caataatggt atttgttggg    60
gcaatcagtt atttgttact gtggtagata ccac    94

<210> SEQ ID NO 257
<211> LENGTH: 65
<212> TYPE: DNA
<213> ORGANISM: Human Papillomavirus

<400> SEQUENCE: 257
gctcagggac acaataatgg tatttgttgg ggcaatcagt tatttgttac tgtggtagat    60
accac    65

<210> SEQ ID NO 258
<211> LENGTH: 94
<212> TYPE: DNA
<213> ORGANISM: Human Papillomavirus

<400> SEQUENCE: 258
tatttaataa gccatattgg ctacaacgtg cacaaggtca taataatggt atttgttggg    60

```
gcaatcaggt atttgttact gtggtagata ccac                              94

<210> SEQ ID NO 259
<211> LENGTH: 65
<212> TYPE: DNA
<213> ORGANISM: Human Papillomavirus

<400> SEQUENCE: 259
gcacaaggtc ataataatgg tatttgttgg ggcaatcagg tatttgttac tgtggtagat    60
accac                                                                65

<210> SEQ ID NO 260
<211> LENGTH: 94
<212> TYPE: DNA
<213> ORGANISM: Human Papillomavirus

<400> SEQUENCE: 260
tttttaataa gccttattgg ttgcaaaagg cccagggaca aaacaatggc atttgctggc    60
ataatcaact gttttttaact gttgtagata ctac                              94

<210> SEQ ID NO 261
<211> LENGTH: 65
<212> TYPE: DNA
<213> ORGANISM: Human Papillomavirus

<400> SEQUENCE: 261
gcccagggac aaaacaatgg catttgctgg cataatcaac tgtttttaac tgttgtagat    60
actac                                                                65

<210> SEQ ID NO 262
<211> LENGTH: 94
<212> TYPE: DNA
<213> ORGANISM: Human Papillomavirus

<400> SEQUENCE: 262
tatttaataa accatattgg ttgcaacgtg cacaaggcca taataatggt atttgttgga    60
gtaaccaatt gtttgttact gtagttgata caac                               94

<210> SEQ ID NO 263
<211> LENGTH: 65
<212> TYPE: DNA
<213> ORGANISM: Human Papillomavirus

<400> SEQUENCE: 263
gcacaaggcc ataataatgg tatttgttgg agtaaccaat tgtttgttac tgtagttgat    60
acaac                                                                65

<210> SEQ ID NO 264
<211> LENGTH: 94
<212> TYPE: DNA
<213> ORGANISM: Human Papillomavirus

<400> SEQUENCE: 264
tatttaataa gccttattgg ctacataagg cccagggcca caacaatggt atatgttggc    60
ataatcaatt atttcttact gttgtggaca ctac                               94

<210> SEQ ID NO 265
<211> LENGTH: 65
<212> TYPE: DNA
```

```
<213> ORGANISM: Human Papillomavirus

<400> SEQUENCE: 265
gcccagggcc acaacaatgg tatatgttgg cataatcaat tatttcttac tgttgtggac    60
accac                                                               65

<210> SEQ ID NO 266
<211> LENGTH: 94
<212> TYPE: DNA
<213> ORGANISM: Human Papillomavirus

<400> SEQUENCE: 266
tatttaacaa gccattgtgg atacaaaagg cccagggcca taacaatggc atatgttttg    60
gcaatcagtt atttgttaca gttgtagaca ccac                               94

<210> SEQ ID NO 267
<211> LENGTH: 65
<212> TYPE: DNA
<213> ORGANISM: Human Papillomavirus

<400> SEQUENCE: 267
gcccagggcc ataacaatgg catatgtttt ggcaatcagt tatttgttac agttgtagac    60
accac                                                               65

<210> SEQ ID NO 268
<211> LENGTH: 94
<212> TYPE: DNA
<213> ORGANISM: Human Papillomavirus

<400> SEQUENCE: 268
tatttaataa accatattgg ttacaacaag cacaaggaca caataatggt atatgttggg    60
gaaatcagct attttttaact gtggttgata ctac                              94

<210> SEQ ID NO 269
<211> LENGTH: 65
<212> TYPE: DNA
<213> ORGANISM: Human Papillomavirus

<400> SEQUENCE: 269
gcacaaggac acaataatgg tatatgttgg ggaaatcagc tatttttaac tgtggttgat    60
actac                                                               65

<210> SEQ ID NO 270
<211> LENGTH: 59
<212> TYPE: DNA
<213> ORGANISM: Human Papillomavirus

<400> SEQUENCE: 270
ggacataata atggcatttg ttttgggaat cagttgtttg ttacagtggt agataccac     59

<210> SEQ ID NO 271
<211> LENGTH: 59
<212> TYPE: DNA
<213> ORGANISM: Human Papillomavirus

<400> SEQUENCE: 271
ggacataata atggcatttg ttttgggaat cagttgtttg ttacagtggt agataccac     59

<210> SEQ ID NO 272
<211> LENGTH: 65
```

```
<212> TYPE: DNA
<213> ORGANISM: Human Papillomavirus

<400> SEQUENCE: 272
gcgcagggcc acaataatgg tatttgttgg ggaaatcagt tatttgttac tgttgtagat      60
actac                                                                 65

<210> SEQ ID NO 273
<211> LENGTH: 65
<212> TYPE: DNA
<213> ORGANISM: Human Papillomavirus

<400> SEQUENCE: 273
gcgcagggcc acaataatgg tatttgttgg ggaaatcagt tatttgttac tgttgtagat      60
actac                                                                 65

<210> SEQ ID NO 274
<211> LENGTH: 94
<212> TYPE: DNA
<213> ORGANISM: Human Papillomavirus

<400> SEQUENCE: 274
tatttaataa gccatattgg ttacataagg cccagggcca taacaatggt atttgttggc      60
ataatcagtt gtttgttact gtagtggaca ctac                                 94

<210> SEQ ID NO 275
<211> LENGTH: 65
<212> TYPE: DNA
<213> ORGANISM: Human Papillomavirus

<400> SEQUENCE: 275
gcccagggcc ataacaatgg tatttgttgg cataatcagt tgtttgttac tgtagtggac      60
actac                                                                 65

<210> SEQ ID NO 276
<211> LENGTH: 94
<212> TYPE: DNA
<213> ORGANISM: Human Papillomavirus

<400> SEQUENCE: 276
tttttaataa gccttattgg ctccaccgtg cgcagggtca caataatggc atttgctgga      60
acaatcagct ttttattacc tgtgttgata ctac                                 94

<210> SEQ ID NO 277
<211> LENGTH: 65
<212> TYPE: DNA
<213> ORGANISM: Human Papillomavirus

<400> SEQUENCE: 277
gcgcagggtc acaataatgg catttgctgg aacaatcagc ttttattac ctgtgttgat       60 actac                                                                 65

<210> SEQ ID NO 278
<211> LENGTH: 94
<212> TYPE: DNA
<213> ORGANISM: Human Papillomavirus

<400> SEQUENCE: 278
tatttaataa accgtactgg ttacaacgtg cgcagggcca caataatggc atatgttggg      60
```

-continued gcaatcagtt gtttgtcaca gttgtggata ccac                          94

<210> SEQ ID NO 279
<211> LENGTH: 65
<212> TYPE: DNA
<213> ORGANISM: Human Papillomavirus

<400> SEQUENCE: 279
gcgcagggcc acaataatgg catatgttgg ggcaatcagt tgtttgtcac agttgtggat    60
accac                                                              65

<210> SEQ ID NO 280
<211> LENGTH: 94
<212> TYPE: DNA
<213> ORGANISM: Human Papillomavirus

<400> SEQUENCE: 280
tgtttaataa gccatattgg ctgcaacgtg cccagggaca taataatggc atctgttgga    60
acaatcagtt atttgtaact gttgtggata ccac                              94

<210> SEQ ID NO 281
<211> LENGTH: 65
<212> TYPE: DNA
<213> ORGANISM: Human Papillomavirus

<400> SEQUENCE: 281
gcccagggac ataataatgg catctgttgg aacaatcagt tatttgtaac tgttgtggat    60
accac                                                              65

<210> SEQ ID NO 282
<211> LENGTH: 94
<212> TYPE: DNA
<213> ORGANISM: Human Papillomavirus

<400> SEQUENCE: 282
tatttaataa gccatactgg ttacaacggg cccagggtca aaacaatggt atttgttggg    60
gcaatcaggt gttttttaaca gttgtagata ccac                             94

<210> SEQ ID NO 283
<211> LENGTH: 65
<212> TYPE: DNA
<213> ORGANISM: Human Papillomavirus

<400> SEQUENCE: 283
gcccagggtc aaaacaatgg tatttgttgg ggcaatcagg tgttttttaac agttgtagat    60 accac                                                              65

<210> SEQ ID NO 284
<211> LENGTH: 65
<212> TYPE: DNA
<213> ORGANISM: Human Papillomavirus

<400> SEQUENCE: 284
gcgcagggcc acaataatgg tatttgttgg gggaatcagt tatttgttac tgttgtagat    60
actac                                                              65

<210> SEQ ID NO 285
<211> LENGTH: 65
<212> TYPE: DNA
<213> ORGANISM: Human Papillomavirus

<400> SEQUENCE: 285
gcgcagggcc acaataatgg tatttgttgg gggaatcagt tatttgttac tgttgtagat    60
actac                                                                65

<210> SEQ ID NO 286
<211> LENGTH: 94
<212> TYPE: DNA
<213> ORGANISM: Human Papillomavirus

<400> SEQUENCE: 286
tatttaataa accttattgg ttgcaacgtg cccaaggcca taataatggc atttgctggg    60
gtaatcaatt atttgttact gtagtagata ctac                                94

<210> SEQ ID NO 287
<211> LENGTH: 65
<212> TYPE: DNA
<213> ORGANISM: Human Papillomavirus

<400> SEQUENCE: 287
gcccaaggcc ataataatgg catttgctgg ggtaatcaat tatttgttac tgtagtagat    60
actac                                                                65

<210> SEQ ID NO 288
<211> LENGTH: 94
<212> TYPE: DNA
<213> ORGANISM: Human Papillomavirus

<400> SEQUENCE: 288
tatttaataa gccttattgg ctacagcgtg cacaaggtca taacaatggc atttgctggg    60
gcaatcagtt atttgttacc gtggttgata ccac                                94

<210> SEQ ID NO 289
<211> LENGTH: 65
<212> TYPE: DNA
<213> ORGANISM: Human Papillomavirus

<400> SEQUENCE: 289
gcacaaggtc ataacaatgg catttgctgg ggcaatcagt tatttgttac cgtggttgat    60
accac                                                                65

<210> SEQ ID NO 290
<211> LENGTH: 94
<212> TYPE: DNA
<213> ORGANISM: Human Papillomavirus

<400> SEQUENCE: 290
tatttaataa accatattgg ctgcacaagg ctcagggttt aaacaatggt atatgttggc    60
acaatcaatt gttttttaaca gttgtagata ctac                               94

<210> SEQ ID NO 291
<211> LENGTH: 65
<212> TYPE: DNA
<213> ORGANISM: Human Papillomavirus

<400> SEQUENCE: 291
gctcagggtt taaacaatgg tatatgttgg cacaatcaat tgttttttaac agttgtagat    60 actac                                                                65

<210> SEQ ID NO 292
<211> LENGTH: 65
<212> TYPE: DNA
<213> ORGANISM: Human Papillomavirus

<400> SEQUENCE: 292
gcccagggcc acaacaatgg tatttgttgg tttaatgaat tgtttgtaac cgttgtggat    60
accac                                                                65

<210> SEQ ID NO 293
<211> LENGTH: 65
<212> TYPE: DNA
<213> ORGANISM: Human Papillomavirus

<400> SEQUENCE: 293
gcccagggcc acaacaatgg tatttgttgg tttaatgaat tgtttgtaac cgttgtggat    60
accac                                                                65

<210> SEQ ID NO 294
<211> LENGTH: 65
<212> TYPE: DNA
<213> ORGANISM: Human Papillomavirus

<400> SEQUENCE: 294
gcacagggtc ataataatgg tatttgttgg tttaatgaac tgtttgttac tgtggtggat    60
actac                                                                65

<210> SEQ ID NO 295
<211> LENGTH: 65
<212> TYPE: DNA
<213> ORGANISM: Human Papillomavirus

<400> SEQUENCE: 295
gcacagggtc ataataatgg tatttgttgg tttaatgaac tgtttgttac tgtggtggat    60
actac                                                                65

<210> SEQ ID NO 296
<211> LENGTH: 65
<212> TYPE: DNA
<213> ORGANISM: Human Papillomavirus

<400> SEQUENCE: 296
gcacagggac ataacaatgg aatttgttgg cataatcaac tgtttctaac tgttgtatat    60
actac                                                                65

<210> SEQ ID NO 297
<211> LENGTH: 65
<212> TYPE: DNA
<213> ORGANISM: Human Papillomavirus

<400> SEQUENCE: 297
gcacagggac ataacaatgg aatttgttgg cataatcaac tgtttctaac tgttgtatat    60
actac                                                                65

<210> SEQ ID NO 298
<211> LENGTH: 65
<212> TYPE: DNA
<213> ORGANISM: Human Papillomavirus

<400> SEQUENCE: 298

```
gcacagggtc ataataatgg catatgctgg ggtaatcagg tatttgttac tgttgtggat    60
actac                                                               65

<210> SEQ ID NO 299
<211> LENGTH: 65
<212> TYPE: DNA
<213> ORGANISM: Human Papillomavirus

<400> SEQUENCE: 299
gcacagggtc ataataatgg catatgctgg ggtaatcagg tatttgttac tgttgtggat    60
actac                                                               65

<210> SEQ ID NO 300
<211> LENGTH: 65
<212> TYPE: DNA
<213> ORGANISM: Human Papillomavirus

<400> SEQUENCE: 300
gcccagggac ataacaatgg tatatgctgg ggtaatcaaa tatttgttac tgttgtagac    60
actac                                                               65

<210> SEQ ID NO 301
<211> LENGTH: 65
<212> TYPE: DNA
<213> ORGANISM: Human Papillomavirus

<400> SEQUENCE: 301
gcccagggac ataacaatgg tatatgctgg ggtaatcaaa tatttgttac tgttgtagac    60
actac                                                               65

<210> SEQ ID NO 302
<211> LENGTH: 94
<212> TYPE: DNA
<213> ORGANISM: Human Papillomavirus

<400> SEQUENCE: 302
tatttaacaa gccctattgg ctgcacaagg cacagggaca caacaatggt atttgttggc    60
ataatcaatt atttcttact gttgtggata ccac                                94

<210> SEQ ID NO 303
<211> LENGTH: 65
<212> TYPE: DNA
<213> ORGANISM: Human Papillomavirus

<400> SEQUENCE: 303
gcacagggac acaacaatgg tatttgttgg cataatcaat tatttcttac tgttgtggat    60
accac                                                               65

<210> SEQ ID NO 304
<211> LENGTH: 65
<212> TYPE: DNA
<213> ORGANISM: Human Papillomavirus

<400> SEQUENCE: 304
gcacagggac ataacaatgg catttgttgg ggcaaccaat tgtttgttac ttgtgtagat    60
actac                                                               65

<210> SEQ ID NO 305
```

<210> SEQ ID NO 305
<211> LENGTH: 65
<212> TYPE: DNA
<213> ORGANISM: Human Papillomavirus

<400> SEQUENCE: 305

```
gcacagggac ataacaatgg catttgttgg ggcaaccaat tgtttgttac ttgtgtagat    60
actac                                                                65
```

<210> SEQ ID NO 306
<211> LENGTH: 94
<212> TYPE: DNA
<213> ORGANISM: Human Papillomavirus

<400> SEQUENCE: 306

```
tgtttaataa gccatattgg ctacaaaaag cccagggaca taacaatggt atttgttggg    60
gtaatcaact gtttgttact gtggtagata ccac                                94
```

<210> SEQ ID NO 307
<211> LENGTH: 65
<212> TYPE: DNA
<213> ORGANISM: Human Papillomavirus

<400> SEQUENCE: 307

```
gcccagggaa ctaataatgg catttgttgg cataaccagt tgtttattac tgtggtggac    60
actac                                                                65
```

<210> SEQ ID NO 308
<211> LENGTH: 65
<212> TYPE: DNA
<213> ORGANISM: Human Papillomavirus

<400> SEQUENCE: 308

```
gcccagggtc ataataatgg catctgttgg tttaatgagc ttttgtgac agttgtagat     60
actac                                                                65
```

<210> SEQ ID NO 309
<211> LENGTH: 65
<212> TYPE: DNA
<213> ORGANISM: Human Papillomavirus

<400> SEQUENCE: 309

```
gcacagggtc ataataatgg tatttgttgg cataatcaat tattttttaac tgttgtagat   60
actac                                                                65
```

<210> SEQ ID NO 310
<211> LENGTH: 94
<212> TYPE: DNA
<213> ORGANISM: Human Papillomavirus

<400> SEQUENCE: 310

```
tgtttaataa gccgttttgg ctgcaaaggg cgcaaggcca caataatggt atttgttggg    60
gtaatcaatt atttgttaca gttgtggata ccac                                94
```

<210> SEQ ID NO 311
<211> LENGTH: 65
<212> TYPE: DNA
<213> ORGANISM: Human Papillomavirus

<400> SEQUENCE: 311

```
gcgcaaggcc acaataatgg tatttgttgg ggtaatcaat tatttgttac agttgtggat    60
``` accac 65

<210> SEQ ID NO 312
<211> LENGTH: 94
<212> TYPE: DNA
<213> ORGANISM: Human Papillomavirus

<400> SEQUENCE: 312
tattcaataa accttattgg ttacaacgag cacagggcca caataatggc atttgttggg    60
gtaaccaact atttgttact gttgttgata ctac                                94

<210> SEQ ID NO 313
<211> LENGTH: 65
<212> TYPE: DNA
<213> ORGANISM: Human Papillomavirus

<400> SEQUENCE: 313
gcacagggcc acaataatgg catttgttgg ggtaaccaac tatttgttac tgttgttgat    60
actac                                                                65

<210> SEQ ID NO 314
<211> LENGTH: 20
<212> TYPE: DNA
<213> ORGANISM: Human Papillomavirus

<400> SEQUENCE: 314
gcmcagggwc ataayaatgg                                                20

<210> SEQ ID NO 315
<211> LENGTH: 65
<212> TYPE: DNA
<213> ORGANISM: Human Papillomavirus

<400> SEQUENCE: 315
gcacagggac ataataatgg catttgctgg aataatcagc tttttattac ttgtgttgac    60
actac                                                                65

<210> SEQ ID NO 316
<211> LENGTH: 65
<212> TYPE: DNA
<213> ORGANISM: Human Papillomavirus

<400> SEQUENCE: 316
gcacagggac ataataatgg catttgctgg aataatcagc tttttattac ttgtgttgac    60
actac                                                                65

<210> SEQ ID NO 317
<211> LENGTH: 65
<212> TYPE: DNA
<213> ORGANISM: Human Papillomavirus

<400> SEQUENCE: 317
gcccagggac ataataatgg catttgttgg tttaatgagt tatttgttac agttgtagat    60
actac                                                                65

<210> SEQ ID NO 318
<211> LENGTH: 65
<212> TYPE: DNA
<213> ORGANISM: Human Papillomavirus -continued

```
<400> SEQUENCE: 318
gcccagggac ataataatgg catttgttgg tttaatgagt tatttgttac agttgtagat    60
actac                                                              65

<210> SEQ ID NO 319
<211> LENGTH: 65
<212> TYPE: DNA
<213> ORGANISM: Human Papillomavirus

<400> SEQUENCE: 319
gcgcggggtc ataacaatgg tatatgctgg tttaatcaat tgtttgtcac ggtggtggat    60
accac                                                              65

<210> SEQ ID NO 320
<211> LENGTH: 65
<212> TYPE: DNA
<213> ORGANISM: Human Papillomavirus

<400> SEQUENCE: 320
gcgcggggtc ataacaatgg tatatgctgg tttaatcaat tgtttgtcac ggtggtggat    60
accac                                                              65

<210> SEQ ID NO 321
<211> LENGTH: 20
<212> TYPE: DNA
<213> ORGANISM: Human Papillomavirus

<400> SEQUENCE: 321
tattcaataa accttattgg                                              20

<210> SEQ ID NO 322
<211> LENGTH: 20
<212> TYPE: DNA
<213> ORGANISM: Human Papillomavirus

<400> SEQUENCE: 322
tgtttaataa accatattgg                                              20

<210> SEQ ID NO 323
<211> LENGTH: 20
<212> TYPE: DNA
<213> ORGANISM: Human Papillomavirus

<400> SEQUENCE: 323
tttttaataa accatattgg                                              20

<210> SEQ ID NO 324
<211> LENGTH: 20
<212> TYPE: DNA
<213> ORGANISM: Human Papillomavirus

<400> SEQUENCE: 324
tatttaataa gccatattgg                                              20

<210> SEQ ID NO 325
<211> LENGTH: 20
<212> TYPE: DNA
<213> ORGANISM: Human Papillomavirus

<400> SEQUENCE: 325
tatttaataa accatattgg                                              20
```

<210> SEQ ID NO 326
<211> LENGTH: 20
<212> TYPE: DNA
<213> ORGANISM: Human Papillomavirus

<400> SEQUENCE: 326
tatttaataa gccttattgg                                              20

<210> SEQ ID NO 327
<211> LENGTH: 20
<212> TYPE: DNA
<213> ORGANISM: Human Papillomavirus

<400> SEQUENCE: 327
tatttaataa gccatattgg                                              20

<210> SEQ ID NO 328
<211> LENGTH: 20
<212> TYPE: DNA
<213> ORGANISM: Human Papillomavirus

<400> SEQUENCE: 328
tttttaataa gccttattgg                                              20

<210> SEQ ID NO 329
<211> LENGTH: 20
<212> TYPE: DNA
<213> ORGANISM: Human Papillomavirus

<400> SEQUENCE: 329
tatttaataa accgtactgg                                              20

<210> SEQ ID NO 330
<211> LENGTH: 20
<212> TYPE: DNA
<213> ORGANISM: Human Papillomavirus

<400> SEQUENCE: 330
tatttaataa accttattgg                                              20

<210> SEQ ID NO 331
<211> LENGTH: 20
<212> TYPE: DNA
<213> ORGANISM: Human Papillomavirus

<400> SEQUENCE: 331
tatttaataa gccttattgg                                              20

<210> SEQ ID NO 332
<211> LENGTH: 20
<212> TYPE: DNA
<213> ORGANISM: Human Papillomavirus

<400> SEQUENCE: 332
tgtttaataa gccatattgg                                              20

<210> SEQ ID NO 333
<211> LENGTH: 20
<212> TYPE: DNA
<213> ORGANISM: Human Papillomavirus

<400> SEQUENCE: 333

-continued tatttaataa accatattgg 20

<210> SEQ ID NO 334
<211> LENGTH: 20
<212> TYPE: DNA
<213> ORGANISM: Human Papillomavirus

<400> SEQUENCE: 334
tttttaataa gccttattgg 20

<210> SEQ ID NO 335
<211> LENGTH: 20
<212> TYPE: DNA
<213> ORGANISM: Human Papillomavirus

<400> SEQUENCE: 335
tatttaacaa gccattgtgg 20

<210> SEQ ID NO 336
<211> LENGTH: 20
<212> TYPE: DNA
<213> ORGANISM: Human Papillomavirus

<400> SEQUENCE: 336
tatttaataa accatattgg 20

<210> SEQ ID NO 337
<211> LENGTH: 20
<212> TYPE: DNA
<213> ORGANISM: Human Papillomavirus

<400> SEQUENCE: 337
tgtttaataa gccatattgg 20

<210> SEQ ID NO 338
<211> LENGTH: 20
<212> TYPE: DNA
<213> ORGANISM: Human Papillomavirus

<400> SEQUENCE: 338
tatttaataa gccatactgg 20

<210> SEQ ID NO 339
<211> LENGTH: 20
<212> TYPE: DNA
<213> ORGANISM: Human Papillomavirus

<400> SEQUENCE: 339
tatttaataa accatattgg 20

<210> SEQ ID NO 340
<211> LENGTH: 20
<212> TYPE: DNA
<213> ORGANISM: Human Papillomavirus

<400> SEQUENCE: 340
tatttaacaa gccctattgg 20

<210> SEQ ID NO 341
<211> LENGTH: 20
<212> TYPE: DNA
<213> ORGANISM: Human Papillomavirus

<400> SEQUENCE: 341
tgtttaataa gccgttttgg                                                    20

<210> SEQ ID NO 342
<211> LENGTH: 20
<212> TYPE: DNA
<213> ORGANISM: Human Papillomavirus

<400> SEQUENCE: 342
gcacagggcc acaataatgg                                                    20

<210> SEQ ID NO 343
<211> LENGTH: 20
<212> TYPE: DNA
<213> ORGANISM: Human Papillomavirus

<400> SEQUENCE: 343
gcacagggtc ataacaatgg                                                    20

<210> SEQ ID NO 344
<211> LENGTH: 20
<212> TYPE: DNA
<213> ORGANISM: Human Papillomavirus

<400> SEQUENCE: 344
gctcagggac acaataatgg                                                    20

<210> SEQ ID NO 345
<211> LENGTH: 20
<212> TYPE: DNA
<213> ORGANISM: Human Papillomavirus

<400> SEQUENCE: 345
gcacaaggtc ataataatgg                                                    20

<210> SEQ ID NO 346
<211> LENGTH: 20
<212> TYPE: DNA
<213> ORGANISM: Human Papillomavirus

<400> SEQUENCE: 346
gcacaaggcc ataataatgg                                                    20

<210> SEQ ID NO 347
<211> LENGTH: 20
<212> TYPE: DNA
<213> ORGANISM: Human Papillomavirus

<400> SEQUENCE: 347
gcccagggcc acaacaatgg                                                    20

<210> SEQ ID NO 348
<211> LENGTH: 20
<212> TYPE: DNA
<213> ORGANISM: Human Papillomavirus

<400> SEQUENCE: 348
gcccagggcc ataacaatgg                                                    20

<210> SEQ ID NO 349
<211> LENGTH: 20
<212> TYPE: DNA
<213> ORGANISM: Human Papillomavirus -continued

<400> SEQUENCE: 349
gcgcagggtc acaataatgg                    20

<210> SEQ ID NO 350
<211> LENGTH: 20
<212> TYPE: DNA
<213> ORGANISM: Human Papillomavirus

<400> SEQUENCE: 350
gcgcagggcc acaataatgg                    20

<210> SEQ ID NO 351
<211> LENGTH: 20
<212> TYPE: DNA
<213> ORGANISM: Human Papillomavirus

<400> SEQUENCE: 351
gcccaaggcc ataataatgg                    20

<210> SEQ ID NO 352
<211> LENGTH: 20
<212> TYPE: DNA
<213> ORGANISM: Human Papillomavirus

<400> SEQUENCE: 352
gcacaaggtc ataacaatgg                    20

<210> SEQ ID NO 353
<211> LENGTH: 20
<212> TYPE: DNA
<213> ORGANISM: Human Papillomavirus

<400> SEQUENCE: 353
gcacagggtc ataataatgg                    20

<210> SEQ ID NO 354
<211> LENGTH: 20
<212> TYPE: DNA
<213> ORGANISM: Human Papillomavirus

<400> SEQUENCE: 354
gcacagggac ataacaatgg                    20

<210> SEQ ID NO 355
<211> LENGTH: 20
<212> TYPE: DNA
<213> ORGANISM: Human Papillomavirus

<400> SEQUENCE: 355
gcccagggac ataacaatgg                    20

<210> SEQ ID NO 356
<211> LENGTH: 20
<212> TYPE: DNA
<213> ORGANISM: Human Papillomavirus

<400> SEQUENCE: 356
gctcagggac ataacaatgg                    20

<210> SEQ ID NO 357
<211> LENGTH: 20
<212> TYPE: DNA
<213> ORGANISM: Human Papillomavirus

<400> SEQUENCE: 357
gcccagggac aaaacaatgg                                               20

<210> SEQ ID NO 358
<211> LENGTH: 20
<212> TYPE: DNA
<213> ORGANISM: Human Papillomavirus

<400> SEQUENCE: 358
gcccagggcc ataacaatgg                                               20

<210> SEQ ID NO 359
<211> LENGTH: 20
<212> TYPE: DNA
<213> ORGANISM: Human Papillomavirus

<400> SEQUENCE: 359
gcacaaggac acaataatgg                                               20

<210> SEQ ID NO 360
<211> LENGTH: 14
<212> TYPE: DNA
<213> ORGANISM: Human Papillomavirus

<400> SEQUENCE: 360
ggacataata atgg                                                     14

<210> SEQ ID NO 361
<211> LENGTH: 20
<212> TYPE: DNA
<213> ORGANISM: Human Papillomavirus

<400> SEQUENCE: 361
gcgcagggcc acaataatgg                                               20

<210> SEQ ID NO 362
<211> LENGTH: 20
<212> TYPE: DNA
<213> ORGANISM: Human Papillomavirus

<400> SEQUENCE: 362
gcccagggac ataataatgg                                               20

<210> SEQ ID NO 363
<211> LENGTH: 20
<212> TYPE: DNA
<213> ORGANISM: Human Papillomavirus

<400> SEQUENCE: 363
gcccagggtc aaaacaatgg                                               20

<210> SEQ ID NO 364
<211> LENGTH: 20
<212> TYPE: DNA
<213> ORGANISM: Human Papillomavirus

<400> SEQUENCE: 364
gcgcagggcc acaataatgg                                               20

<210> SEQ ID NO 365
<211> LENGTH: 20
<212> TYPE: DNA

<213> ORGANISM: Human Papillomavirus

<400> SEQUENCE: 365
gctcagggtt taaacaatgg                                            20

<210> SEQ ID NO 366
<211> LENGTH: 20
<212> TYPE: DNA
<213> ORGANISM: Human Papillomavirus

<400> SEQUENCE: 366
gcccagggcc acaacaatgg                                            20

<210> SEQ ID NO 367
<211> LENGTH: 20
<212> TYPE: DNA
<213> ORGANISM: Human Papillomavirus

<400> SEQUENCE: 367
gcacagggtc ataataatgg                                            20

<210> SEQ ID NO 368
<211> LENGTH: 20
<212> TYPE: DNA
<213> ORGANISM: Human Papillomavirus

<400> SEQUENCE: 368
gcacagggac ataacaatgg                                            20

<210> SEQ ID NO 369
<211> LENGTH: 20
<212> TYPE: DNA
<213> ORGANISM: Human Papillomavirus

<400> SEQUENCE: 369
gcccagggac ataacaatgg                                            20

<210> SEQ ID NO 370
<211> LENGTH: 20
<212> TYPE: DNA
<213> ORGANISM: Human Papillomavirus

<400> SEQUENCE: 370
gcacagggac acaacaatgg                                            20

<210> SEQ ID NO 371
<211> LENGTH: 20
<212> TYPE: DNA
<213> ORGANISM: Human Papillomavirus

<400> SEQUENCE: 371
gcgcaaggcc acaataatgg                                            20

<210> SEQ ID NO 372
<211> LENGTH: 20
<212> TYPE: DNA
<213> ORGANISM: Human Papillomavirus

<400> SEQUENCE: 372
gcacagggac ataataatgg                                            20

<210> SEQ ID NO 373
<211> LENGTH: 20

-continued

```
<212> TYPE: DNA
<213> ORGANISM: Human Papillomavirus

<400> SEQUENCE: 373
gcccagggac ataataatgg                                          20

<210> SEQ ID NO 374
<211> LENGTH: 20
<212> TYPE: DNA
<213> ORGANISM: Human Papillomavirus

<400> SEQUENCE: 374
gcgcggggtc ataacaatgg                                          20

<210> SEQ ID NO 375
<211> LENGTH: 23
<212> TYPE: DNA
<213> ORGANISM: Human Papillomavirus

<400> SEQUENCE: 375
tttgttactg ttgttgatac tac                                      23

<210> SEQ ID NO 376
<211> LENGTH: 23
<212> TYPE: DNA
<213> ORGANISM: Human Papillomavirus

<400> SEQUENCE: 376
tttgttactg tggtagatac cac                                      23

<210> SEQ ID NO 377
<211> LENGTH: 23
<212> TYPE: DNA
<213> ORGANISM: Human Papillomavirus

<400> SEQUENCE: 377
tttgttactg tggtagatac cac                                      23

<210> SEQ ID NO 378
<211> LENGTH: 23
<212> TYPE: DNA
<213> ORGANISM: Human Papillomavirus

<400> SEQUENCE: 378
tttgttactg tggtagatac cac                                      23

<210> SEQ ID NO 379
<211> LENGTH: 23
<212> TYPE: DNA
<213> ORGANISM: Human Papillomavirus

<400> SEQUENCE: 379
tttgttactg tagttgatac aac                                      23

<210> SEQ ID NO 380
<211> LENGTH: 23
<212> TYPE: DNA
<213> ORGANISM: Human Papillomavirus

<400> SEQUENCE: 380
tttcttactg ttgtggacac tac                                      23

<210> SEQ ID NO 381
```

```
<211> LENGTH: 23
<212> TYPE: DNA
<213> ORGANISM: Human Papillomavirus

<400> SEQUENCE: 381
tttgttactg tagtggacac tac                                    23

<210> SEQ ID NO 382
<211> LENGTH: 23
<212> TYPE: DNA
<213> ORGANISM: Human Papillomavirus

<400> SEQUENCE: 382
tttattacct gtgttgatac tac                                    23

<210> SEQ ID NO 383
<211> LENGTH: 23
<212> TYPE: DNA
<213> ORGANISM: Human Papillomavirus

<400> SEQUENCE: 383
tttgtcacag ttgtggatac cac                                    23

<210> SEQ ID NO 384
<211> LENGTH: 23
<212> TYPE: DNA
<213> ORGANISM: Human Papillomavirus

<400> SEQUENCE: 384
tttgttactg tagtagatac tac                                    23

<210> SEQ ID NO 385
<211> LENGTH: 23
<212> TYPE: DNA
<213> ORGANISM: Human Papillomavirus

<400> SEQUENCE: 385
tttgttaccg tggttgatac cac                                    23

<210> SEQ ID NO 386
<211> LENGTH: 23
<212> TYPE: DNA
<213> ORGANISM: Human Papillomavirus

<400> SEQUENCE: 386
tttgttactg ttgtggatac tac                                    23

<210> SEQ ID NO 387
<211> LENGTH: 23
<212> TYPE: DNA
<213> ORGANISM: Human Papillomavirus

<400> SEQUENCE: 387
tttgttactt gtgtagatac tac                                    23

<210> SEQ ID NO 388
<211> LENGTH: 23
<212> TYPE: DNA
<213> ORGANISM: Human Papillomavirus

<400> SEQUENCE: 388
tttgttactg tggtagatac cac                                    23
```

```
<210> SEQ ID NO 389
<211> LENGTH: 23
<212> TYPE: DNA
<213> ORGANISM: Human Papillomavirus

<400> SEQUENCE: 389
tttgttactg tggtagatac cac                                          23

<210> SEQ ID NO 390
<211> LENGTH: 23
<212> TYPE: DNA
<213> ORGANISM: Human Papillomavirus

<400> SEQUENCE: 390
tttttaactg ttgtagatac tac                                          23

<210> SEQ ID NO 391
<211> LENGTH: 23
<212> TYPE: DNA
<213> ORGANISM: Human Papillomavirus

<400> SEQUENCE: 391
tttgttacag ttgtagacac cac                                          23

<210> SEQ ID NO 392
<211> LENGTH: 23
<212> TYPE: DNA
<213> ORGANISM: Human Papillomavirus

<400> SEQUENCE: 392
tttttaactg tggttgatac tac                                          23

<210> SEQ ID NO 393
<211> LENGTH: 23
<212> TYPE: DNA
<213> ORGANISM: Human Papillomavirus

<400> SEQUENCE: 393
tttgttacag tggtagatac cac                                          23

<210> SEQ ID NO 394
<211> LENGTH: 23
<212> TYPE: DNA
<213> ORGANISM: Human Papillomavirus

<400> SEQUENCE: 394
tttgttactg ttgtagatac tac                                          23

<210> SEQ ID NO 395
<211> LENGTH: 23
<212> TYPE: DNA
<213> ORGANISM: Human Papillomavirus

<400> SEQUENCE: 395
tttgtaactg ttgtggatac cac                                          23

<210> SEQ ID NO 396
<211> LENGTH: 23
<212> TYPE: DNA
<213> ORGANISM: Human Papillomavirus

<400> SEQUENCE: 396
tttttaacag ttgtagatac cac                                          23
```

<210> SEQ ID NO 397
<211> LENGTH: 23
<212> TYPE: DNA
<213> ORGANISM: Human Papillomavirus

<400> SEQUENCE: 397
tttgttactg ttgtagatac tac                                    23

<210> SEQ ID NO 398
<211> LENGTH: 23
<212> TYPE: DNA
<213> ORGANISM: Human Papillomavirus

<400> SEQUENCE: 398
tttttaacag ttgtagatac tac                                    23

<210> SEQ ID NO 399
<211> LENGTH: 23
<212> TYPE: DNA
<213> ORGANISM: Human Papillomavirus

<400> SEQUENCE: 399
tttgtaaccg ttgtggatac cac                                    23

<210> SEQ ID NO 400
<211> LENGTH: 23
<212> TYPE: DNA
<213> ORGANISM: Human Papillomavirus

<400> SEQUENCE: 400
tttgttactg tggtggatac tac                                    23

<210> SEQ ID NO 401
<211> LENGTH: 23
<212> TYPE: DNA
<213> ORGANISM: Human Papillomavirus

<400> SEQUENCE: 401
tttctaactg ttgtatatac tac                                    23

<210> SEQ ID NO 402
<211> LENGTH: 23
<212> TYPE: DNA
<213> ORGANISM: Human Papillomavirus

<400> SEQUENCE: 402
tttgttactg ttgtagacac tac                                    23

<210> SEQ ID NO 403
<211> LENGTH: 23
<212> TYPE: DNA
<213> ORGANISM: Human Papillomavirus

<400> SEQUENCE: 403
tttcttactg ttgtggatac cac                                    23

<210> SEQ ID NO 404
<211> LENGTH: 23
<212> TYPE: DNA
<213> ORGANISM: Human Papillomavirus

<400> SEQUENCE: 404
tttgttacag ttgtggatac cac                                    23

<210> SEQ ID NO 405
<211> LENGTH: 23
<212> TYPE: DNA
<213> ORGANISM: Human Papillomavirus

<400> SEQUENCE: 405
tttattactt gtgttgacac tac                                    23

<210> SEQ ID NO 406
<211> LENGTH: 23
<212> TYPE: DNA
<213> ORGANISM: Human Papillomavirus

<400> SEQUENCE: 406
tttgttacag ttgtagatac tac                                    23

<210> SEQ ID NO 407
<211> LENGTH: 23
<212> TYPE: DNA
<213> ORGANISM: Human Papillomavirus

<400> SEQUENCE: 407
tttgtcacgg tggtggatac cac                                    23

<210> SEQ ID NO 408
<211> LENGTH: 22
<212> TYPE: DNA
<213> ORGANISM: Human Papillomavirus

<400> SEQUENCE: 408
catttgttgg ggtaaccaac ta                                     22

<210> SEQ ID NO 409
<211> LENGTH: 22
<212> TYPE: DNA
<213> ORGANISM: Human Papillomavirus

<400> SEQUENCE: 409
tgtttgctgg cataatcaat ta                                     22

<210> SEQ ID NO 410
<211> LENGTH: 22
<212> TYPE: DNA
<213> ORGANISM: Human Papillomavirus

<400> SEQUENCE: 410
tatttgttgg ggcaatcagt ta                                     22

<210> SEQ ID NO 411
<211> LENGTH: 22
<212> TYPE: DNA
<213> ORGANISM: Human Papillomavirus

<400> SEQUENCE: 411
tatttgttgg ggcaatcagg ta                                     22

<210> SEQ ID NO 412
<211> LENGTH: 22
<212> TYPE: DNA
<213> ORGANISM: Human Papillomavirus

<400> SEQUENCE: 412

-continued tatttgttgg agtaaccaat tg 22

<210> SEQ ID NO 413
<211> LENGTH: 22
<212> TYPE: DNA
<213> ORGANISM: Human Papillomavirus

<400> SEQUENCE: 413
tatatgttgg cataatcaat ta 22

<210> SEQ ID NO 414
<211> LENGTH: 22
<212> TYPE: DNA
<213> ORGANISM: Human Papillomavirus

<400> SEQUENCE: 414
tatttgttgg cataatcagt tg 22

<210> SEQ ID NO 415
<211> LENGTH: 22
<212> TYPE: DNA
<213> ORGANISM: Human Papillomavirus

<400> SEQUENCE: 415
catttgctgg aacaatcagc tt 22

<210> SEQ ID NO 416
<211> LENGTH: 22
<212> TYPE: DNA
<213> ORGANISM: Human Papillomavirus

<400> SEQUENCE: 416
catatgttgg ggcaatcagt tg 22

<210> SEQ ID NO 417
<211> LENGTH: 22
<212> TYPE: DNA
<213> ORGANISM: Human Papillomavirus

<400> SEQUENCE: 417
catttgctgg ggtaatcaat ta 22

<210> SEQ ID NO 418
<211> LENGTH: 22
<212> TYPE: DNA
<213> ORGANISM: Human Papillomavirus

<400> SEQUENCE: 418
catttgctgg ggcaatcagt ta 22

<210> SEQ ID NO 419
<211> LENGTH: 22
<212> TYPE: DNA
<213> ORGANISM: Human Papillomavirus

<400> SEQUENCE: 419
catatgctgg ggtaatcagg ta 22

<210> SEQ ID NO 420
<211> LENGTH: 22
<212> TYPE: DNA
<213> ORGANISM: Human Papillomavirus

<400> SEQUENCE: 420

-continued catttgttgg ggcaaccaat tg          22

<210> SEQ ID NO 421
<211> LENGTH: 22
<212> TYPE: DNA
<213> ORGANISM: Human Papillomavirus

<400> SEQUENCE: 421
tatttgttgg ggtaatcaac tg          22

<210> SEQ ID NO 422
<211> LENGTH: 22
<212> TYPE: DNA
<213> ORGANISM: Human Papillomavirus

<400> SEQUENCE: 422
tatttgctgg ggaaaccact tg          22

<210> SEQ ID NO 423
<211> LENGTH: 22
<212> TYPE: DNA
<213> ORGANISM: Human Papillomavirus

<400> SEQUENCE: 423
catttgctgg cataatcaac tg          22

<210> SEQ ID NO 424
<211> LENGTH: 22
<212> TYPE: DNA
<213> ORGANISM: Human Papillomavirus

<400> SEQUENCE: 424
catatgtttt ggcaatcagt ta          22

<210> SEQ ID NO 425
<211> LENGTH: 22
<212> TYPE: DNA
<213> ORGANISM: Human Papillomavirus

<400> SEQUENCE: 425
tatatgttgg ggaaatcagc ta          22

<210> SEQ ID NO 426
<211> LENGTH: 22
<212> TYPE: DNA
<213> ORGANISM: Human Papillomavirus

<400> SEQUENCE: 426
catttgtttt gggaatcagt tg          22

<210> SEQ ID NO 427
<211> LENGTH: 22
<212> TYPE: DNA
<213> ORGANISM: Human Papillomavirus

<400> SEQUENCE: 427
tatttgttgg ggaaatcagt ta          22

<210> SEQ ID NO 428
<211> LENGTH: 22
<212> TYPE: DNA
<213> ORGANISM: Human Papillomavirus -continued

```
<400> SEQUENCE: 428
catctgttgg aacaatcagt ta                                           22

<210> SEQ ID NO 429
<211> LENGTH: 22
<212> TYPE: DNA
<213> ORGANISM: Human Papillomavirus

<400> SEQUENCE: 429
tatttgttgg ggcaatcagg tg                                           22

<210> SEQ ID NO 430
<211> LENGTH: 22
<212> TYPE: DNA
<213> ORGANISM: Human Papillomavirus

<400> SEQUENCE: 430
tatttgttgg gggaatcagt ta                                           22

<210> SEQ ID NO 431
<211> LENGTH: 22
<212> TYPE: DNA
<213> ORGANISM: Human Papillomavirus

<400> SEQUENCE: 431
tatatgttgg cacaatcaat tg                                           22

<210> SEQ ID NO 432
<211> LENGTH: 22
<212> TYPE: DNA
<213> ORGANISM: Human Papillomavirus

<400> SEQUENCE: 432
tatttgttgg tttaatgaat tg                                           22

<210> SEQ ID NO 433
<211> LENGTH: 22
<212> TYPE: DNA
<213> ORGANISM: Human Papillomavirus

<400> SEQUENCE: 433
tatttgttgg tttaatgaac tg                                           22

<210> SEQ ID NO 434
<211> LENGTH: 22
<212> TYPE: DNA
<213> ORGANISM: Human Papillomavirus

<400> SEQUENCE: 434
aatttgttgg cataatcaac tg                                           22

<210> SEQ ID NO 435
<211> LENGTH: 22
<212> TYPE: DNA
<213> ORGANISM: Human Papillomavirus

<400> SEQUENCE: 435
tatatgctgg ggtaatcaaa ta                                           22

<210> SEQ ID NO 436
<211> LENGTH: 22
<212> TYPE: DNA
<213> ORGANISM: Human Papillomavirus
```

<400> SEQUENCE: 436
tatttgttgg cataatcaat ta                                              22

<210> SEQ ID NO 437
<211> LENGTH: 22
<212> TYPE: DNA
<213> ORGANISM: Human Papillomavirus

<400> SEQUENCE: 437
tatttgttgg ggtaatcaat ta                                              22

<210> SEQ ID NO 438
<211> LENGTH: 22
<212> TYPE: DNA
<213> ORGANISM: Human Papillomavirus

<400> SEQUENCE: 438
catttgctgg aataatcagc tt                                              22

<210> SEQ ID NO 439
<211> LENGTH: 22
<212> TYPE: DNA
<213> ORGANISM: Human Papillomavirus

<400> SEQUENCE: 439
catttgttgg tttaatgagt ta                                              22

<210> SEQ ID NO 440
<211> LENGTH: 22
<212> TYPE: DNA
<213> ORGANISM: Human Papillomavirus

<400> SEQUENCE: 440
tatatgctgg tttaatcaat tg                                              22

<210> SEQ ID NO 441
<211> LENGTH: 65
<212> TYPE: DNA
<213> ORGANISM: Human Papillomavirus

<400> SEQUENCE: 441
gcacagggcc acaataatgg catttgttgg ggtaaccaac tatttgttac tgttgttgat     60
actac                                                                 65

<210> SEQ ID NO 442
<211> LENGTH: 65
<212> TYPE: DNA
<213> ORGANISM: Human Papillomavirus

<400> SEQUENCE: 442
gcacagggtc ataacaatgg tgtttgctgg cataatcaat tatttgttac tgtggtagat     60
accac                                                                 65

<210> SEQ ID NO 443
<211> LENGTH: 65
<212> TYPE: DNA
<213> ORGANISM: Human Papillomavirus

<400> SEQUENCE: 443
gctcagggac acaataatgg tatttgttgg ggcaatcagt tatttgttac tgtggtagat     60

-continued

```
accac                                                             65

<210> SEQ ID NO 444
<211> LENGTH: 65
<212> TYPE: DNA
<213> ORGANISM: Human Papillomavirus

<400> SEQUENCE: 444
gcacaaggtc ataataatgg tatttgttgg ggcaatcagg tatttgttac tgtggtagat     60
accac                                                             65

<210> SEQ ID NO 445
<211> LENGTH: 65
<212> TYPE: DNA
<213> ORGANISM: Human Papillomavirus

<400> SEQUENCE: 445
gcacaaggcc ataataatgg tatttgttgg agtaaccaat tgtttgttac tgtagttgat     60
acaac                                                             65

<210> SEQ ID NO 446
<211> LENGTH: 65
<212> TYPE: DNA
<213> ORGANISM: Human Papillomavirus

<400> SEQUENCE: 446
gcccagggcc acaacaatgg tatatgttgg cataatcaat tatttcttac tgttgtggac     60
actac                                                             65

<210> SEQ ID NO 447
<211> LENGTH: 65
<212> TYPE: DNA
<213> ORGANISM: Human Papillomavirus

<400> SEQUENCE: 447
gcccagggcc ataacaatgg tatttgttgg cataatcagt tgtttgttac tgtagtggac     60
actac                                                             65

<210> SEQ ID NO 448
<211> LENGTH: 65
<212> TYPE: DNA
<213> ORGANISM: Human Papillomavirus

<400> SEQUENCE: 448
gcgcagggtc acaataatgg catttgctgg aacaatcagc tttttattac ctgtgttgat     60
actac                                                             65

<210> SEQ ID NO 449
<211> LENGTH: 65
<212> TYPE: DNA
<213> ORGANISM: Human Papillomavirus

<400> SEQUENCE: 449
gcgcagggcc acaataatgg catatgttgg ggcaatcagt tgtttgtcac agttgtggat     60
accac                                                             65

<210> SEQ ID NO 450
<211> LENGTH: 65
<212> TYPE: DNA
<213> ORGANISM: Human Papillomavirus
```

<400> SEQUENCE: 450
gcccaaggcc ataataatgg catttgctgg ggtaatcaat tatttgttac tgtagtagat    60
actac                                                                65

<210> SEQ ID NO 451
<211> LENGTH: 65
<212> TYPE: DNA
<213> ORGANISM: Human Papillomavirus

<400> SEQUENCE: 451
gcacaaggtc ataacaatgg catttgctgg gcaatcagt tatttgttac cgtggttgat     60
accac                                                                65

<210> SEQ ID NO 452
<211> LENGTH: 65
<212> TYPE: DNA
<213> ORGANISM: Human Papillomavirus

<400> SEQUENCE: 452
gcacagggtc ataataatgg catatgctgg ggtaatcagg tatttgttac tgttgtggat    60
actac                                                                65

<210> SEQ ID NO 453
<211> LENGTH: 65
<212> TYPE: DNA
<213> ORGANISM: Human Papillomavirus

<400> SEQUENCE: 453
gcacagggac ataacaatgg catttgttgg ggcaaccaat tgtttgttac ttgtgtagat    60
actac                                                                65

<210> SEQ ID NO 454
<211> LENGTH: 65
<212> TYPE: DNA
<213> ORGANISM: Human Papillomavirus

<400> SEQUENCE: 454
gcccagggac ataacaatgg tatttgttgg ggtaatcaac tgtttgttac tgtggtagat    60
accac                                                                65

<210> SEQ ID NO 455
<211> LENGTH: 65
<212> TYPE: DNA
<213> ORGANISM: Human Papillomavirus

<400> SEQUENCE: 455
gctcagggac ataacaatgg tatttgctgg ggaaaccact tgtttgttac tgtggtagat    60
accac                                                                65

<210> SEQ ID NO 456
<211> LENGTH: 65
<212> TYPE: DNA
<213> ORGANISM: Human Papillomavirus

<400> SEQUENCE: 456
gcccagggac aaaacaatgg catttgctgg cataatcaac tgttttaac tgttgtagat    60 actac                                                                65

```
<210> SEQ ID NO 457
<211> LENGTH: 65
<212> TYPE: DNA
<213> ORGANISM: Human Papillomavirus

<400> SEQUENCE: 457
gcccagggcc ataacaatgg catatgtttt ggcaatcagt tatttgttac agttgtagac    60
accac                                                                65

<210> SEQ ID NO 458
<211> LENGTH: 65
<212> TYPE: DNA
<213> ORGANISM: Human Papillomavirus

<400> SEQUENCE: 458
gcacaaggac acaataatgg tatatgttgg ggaaatcagc tatttttaac tgtggttgat    60
actac                                                                65

<210> SEQ ID NO 459
<211> LENGTH: 59
<212> TYPE: DNA
<213> ORGANISM: Human Papillomavirus

<400> SEQUENCE: 459
ggacataata atggcatttg ttttgggaat cagttgtttg ttacagtggt agataccac    59

<210> SEQ ID NO 460
<211> LENGTH: 65
<212> TYPE: DNA
<213> ORGANISM: Human Papillomavirus

<400> SEQUENCE: 460
gcgcagggcc acaataatgg tatttgttgg ggaaatcagt tatttgttac tgttgtagat    60
actac                                                                65

<210> SEQ ID NO 461
<211> LENGTH: 65
<212> TYPE: DNA
<213> ORGANISM: Human Papillomavirus

<400> SEQUENCE: 461
gcccagggac ataataatgg catctgttgg aacaatcagt tatttgtaac tgttgtggat    60
accac                                                                65

<210> SEQ ID NO 462
<211> LENGTH: 65
<212> TYPE: DNA
<213> ORGANISM: Human Papillomavirus

<400> SEQUENCE: 462
gcccagggtc aaaacaatgg tatttgttgg ggcaatcagg tgtttttaac agttgtagat    60
accac                                                                65

<210> SEQ ID NO 463
<211> LENGTH: 65
<212> TYPE: DNA
<213> ORGANISM: Human Papillomavirus

<400> SEQUENCE: 463
gcgcagggcc acaataatgg tatttgttgg gggaatcagt tatttgttac tgttgtagat    60
```

```
actac                                                                65

<210> SEQ ID NO 464
<211> LENGTH: 65
<212> TYPE: DNA
<213> ORGANISM: Human Papillomavirus

<400> SEQUENCE: 464
gctcagggtt taaacaatgg tatatgttgg cacaatcaat tgtttttaac agttgtagat    60
actac                                                                65

<210> SEQ ID NO 465
<211> LENGTH: 65
<212> TYPE: DNA
<213> ORGANISM: Human Papillomavirus

<400> SEQUENCE: 465
gcccagggcc acaacaatgg tatttgttgg tttaatgaat tgtttgtaac cgttgtggat    60
accac                                                                65

<210> SEQ ID NO 466
<211> LENGTH: 65
<212> TYPE: DNA
<213> ORGANISM: Human Papillomavirus

<400> SEQUENCE: 466
gcacagggtc ataataatgg tatttgttgg tttaatgaac tgtttgttac tgtggtggat    60
actac                                                                65

<210> SEQ ID NO 467
<211> LENGTH: 65
<212> TYPE: DNA
<213> ORGANISM: Human Papillomavirus

<400> SEQUENCE: 467
gcacagggac ataacaatgg aatttgttgg cataatcaac tgtttctaac tgttgtatat    60
actac                                                                65

<210> SEQ ID NO 468
<211> LENGTH: 65
<212> TYPE: DNA
<213> ORGANISM: Human Papillomavirus

<400> SEQUENCE: 468
gcccagggac ataacaatgg tatatgctgg ggtaatcaaa tatttgttac tgttgtagac    60
actac                                                                65

<210> SEQ ID NO 469
<211> LENGTH: 65
<212> TYPE: DNA
<213> ORGANISM: Human Papillomavirus

<400> SEQUENCE: 469
gcacagggac acaacaatgg tatttgttgg cataatcaat tatttcttac tgttgtggat    60
accac                                                                65

<210> SEQ ID NO 470
<211> LENGTH: 65
<212> TYPE: DNA
```

<213> ORGANISM: Human Papillomavirus

<400> SEQUENCE: 470
gcgcaaggcc acaataatgg tatttgttgg ggtaatcaat tatttgttac agttgtggat    60
accac                                                              65

<210> SEQ ID NO 471
<211> LENGTH: 65
<212> TYPE: DNA
<213> ORGANISM: Human Papillomavirus

<400> SEQUENCE: 471
gcacagggac ataataatgg catttgctgg aataatcagc tttttattac ttgtgttgac    60
actac                                                              65

<210> SEQ ID NO 472
<211> LENGTH: 65
<212> TYPE: DNA
<213> ORGANISM: Human Papillomavirus

<400> SEQUENCE: 472
gcccagggac ataataatgg catttgttgg tttaatgagt tatttgttac agttgtagat    60
actac                                                              65

<210> SEQ ID NO 473
<211> LENGTH: 65
<212> TYPE: DNA
<213> ORGANISM: Human Papillomavirus

<400> SEQUENCE: 473
gcgcggggtc ataacaatgg tatatgctgg tttaatcaat tgtttgtcac ggtggtggat    60
accac                                                              65

<210> SEQ ID NO 474
<211> LENGTH: 20
<212> TYPE: DNA
<213> ORGANISM: Human Papillomavirus

<400> SEQUENCE: 474
gcccagggac acaataatgg                                              20

<210> SEQ ID NO 475
<211> LENGTH: 20
<212> TYPE: DNA
<213> ORGANISM: Human Papillomavirus

<400> SEQUENCE: 475
gcacagggtc ataataatgg                                              20

<210> SEQ ID NO 476
<211> LENGTH: 20
<212> TYPE: DNA
<213> ORGANISM: Human Papillomavirus

<400> SEQUENCE: 476
gcacagggac acaataatgg                                              20

<210> SEQ ID NO 477
<211> LENGTH: 20
<212> TYPE: DNA
<213> ORGANISM: Human Papillomavirus

<400> SEQUENCE: 477
gcccagggaa ctaataatgg    20

<210> SEQ ID NO 478
<211> LENGTH: 20
<212> TYPE: DNA
<213> ORGANISM: Human Papillomavirus

<400> SEQUENCE: 478
gcccagggtc ataataatgg    20

<210> SEQ ID NO 479
<211> LENGTH: 20
<212> TYPE: DNA
<213> ORGANISM: Human Papillomavirus

<400> SEQUENCE: 479
gcacagggtc ataataatgg    20

<210> SEQ ID NO 480
<211> LENGTH: 23
<212> TYPE: DNA
<213> ORGANISM: Human Papillomavirus

<400> SEQUENCE: 480
tttgttactg tagttgatac tac    23

<210> SEQ ID NO 481
<211> LENGTH: 23
<212> TYPE: DNA
<213> ORGANISM: Human Papillomavirus

<400> SEQUENCE: 481
tttgttacct gtgttgatac cac    23

<210> SEQ ID NO 482
<211> LENGTH: 23
<212> TYPE: DNA
<213> ORGANISM: Human Papillomavirus

<400> SEQUENCE: 482
tttgttactg ttgtggacac cac    23

<210> SEQ ID NO 483
<211> LENGTH: 23
<212> TYPE: DNA
<213> ORGANISM: Human Papillomavirus

<400> SEQUENCE: 483
tttattactg tggtggacac tac    23

<210> SEQ ID NO 484
<211> LENGTH: 23
<212> TYPE: DNA
<213> ORGANISM: Human Papillomavirus

<400> SEQUENCE: 484
tttgtgacag ttgtagatac tac    23

<210> SEQ ID NO 485
<211> LENGTH: 23
<212> TYPE: DNA

```
<213> ORGANISM: Human Papillomavirus

<400> SEQUENCE: 485
tttttaactg ttgtagatac tac                                    23

<210> SEQ ID NO 486
<211> LENGTH: 22
<212> TYPE: DNA
<213> ORGANISM: Human Papillomavirus

<400> SEQUENCE: 486
tatatgttgg ggcaatcact tg                                     22

<210> SEQ ID NO 487
<211> LENGTH: 22
<212> TYPE: DNA
<213> ORGANISM: Human Papillomavirus

<400> SEQUENCE: 487
tatctgttgg ggcaatcaat tg                                     22

<210> SEQ ID NO 488
<211> LENGTH: 22
<212> TYPE: DNA
<213> ORGANISM: Human Papillomavirus

<400> SEQUENCE: 488
catttgttgg ggcaaccagg ta                                     22

<210> SEQ ID NO 489
<211> LENGTH: 22
<212> TYPE: DNA
<213> ORGANISM: Human Papillomavirus

<400> SEQUENCE: 489
catttgttgg cataaccagt tg                                     22

<210> SEQ ID NO 490
<211> LENGTH: 22
<212> TYPE: DNA
<213> ORGANISM: Human Papillomavirus

<400> SEQUENCE: 490
catctgttgg tttaatgagc tt                                     22

<210> SEQ ID NO 491
<211> LENGTH: 22
<212> TYPE: DNA
<213> ORGANISM: Human Papillomavirus

<400> SEQUENCE: 491
tatttgttgg cataatcaat ta                                     22

<210> SEQ ID NO 492
<211> LENGTH: 65
<212> TYPE: DNA
<213> ORGANISM: Human Papillomavirus

<400> SEQUENCE: 492
gcccagggac acaataatgg tatatgttgg ggcaatcact tgtttgttac tgtagttgat    60
actac                                                        65
```

-continued

```
<210> SEQ ID NO 493
<211> LENGTH: 65
<212> TYPE: DNA
<213> ORGANISM: Human Papillomavirus

<400> SEQUENCE: 493
gcacagggtc ataataatgg tatctgttgg ggcaatcaat tgtttgttac ctgtgttgat    60
accac                                                               65

<210> SEQ ID NO 494
<211> LENGTH: 65
<212> TYPE: DNA
<213> ORGANISM: Human Papillomavirus

<400> SEQUENCE: 494
gcacagggac acaataatgg catttgttgg ggcaaccagg tatttgttac tgttgtggac    60
accac                                                               65

<210> SEQ ID NO 495
<211> LENGTH: 65
<212> TYPE: DNA
<213> ORGANISM: Human Papillomavirus

<400> SEQUENCE: 495
gcccagggaa ctaataatgg catttgttgg cataaccagt tgtttattac tgtggtggac    60
actac                                                               65

<210> SEQ ID NO 496
<211> LENGTH: 65
<212> TYPE: DNA
<213> ORGANISM: Human Papillomavirus

<400> SEQUENCE: 496
gcccagggtc ataataatgg catctgttgg tttaatgagc tttttgtgac agttgtagat    60
actac                                                               65

<210> SEQ ID NO 497
<211> LENGTH: 65
<212> TYPE: DNA
<213> ORGANISM: Human Papillomavirus

<400> SEQUENCE: 497
gcacagggtc ataataatgg tatttgttgg cataatcaat tatttttaac tgttgtagat    60
actac                                                               65
```